(12) United States Patent
Munson et al.

(10) Patent No.: US 7,135,575 B2
(45) Date of Patent: Nov. 14, 2006

(54) P38 INHIBITORS AND METHODS OF USE THEREOF

(75) Inventors: Mark Munson, Louisville, CO (US); James Rizzi, Longmont, CO (US); Martha Rodriguez, Longmont, CO (US); Ganghyeok Kim, Superior, CO (US)

(73) Assignee: Array BioPharma, Inc., Boulder, CO (US)

( * ) Notice: Subject to any disclaimer, the term of this patent is extended or adjusted under 35 U.S.C. 154(b) by 162 days.

(21) Appl. No.: 10/378,164

(22) Filed: Mar. 3, 2003

(65) Prior Publication Data
US 2004/0176325 A1 Sep. 9, 2004

(51) Int. Cl.
*C07D 231/56* (2006.01)
(52) U.S. Cl. .................................................. 548/361.1
(58) Field of Classification Search .............. 548/361.1
See application file for complete search history.

(56) References Cited

U.S. PATENT DOCUMENTS

| | | | |
|---|---|---|---|
| 5,945,418 A | 8/1999 | Bemis et al. | |
| 6,080,763 A | 6/2000 | Regan et al. | |
| 6,093,742 A | 7/2000 | Salituro et al. | |
| 6,214,830 B1 | 4/2001 | Beers et al. | |
| 6,228,881 B1 | 5/2001 | Regan et al. | |
| 6,242,453 B1 | 6/2001 | Cirillo et al. | |
| 6,297,381 B1 | 10/2001 | Cirillo et al. | |
| 6,358,945 B1 | 3/2002 | Breitfelder et al. | |
| 6,432,995 B1 | 8/2002 | Hickey et al. | |
| 6,479,507 B1 | 11/2002 | Cheng et al. | |
| 6,503,930 B1 | 1/2003 | Hanson et al. | |
| 2004/0192653 A1* | 9/2004 | Munson et al. ............... 514/81 |

FOREIGN PATENT DOCUMENTS

| | | |
|---|---|---|
| WO | WO 97/12876 | 4/1997 |
| WO | WO 00/71535 A1 | 11/2000 |
| WO | WO 01/02369 A2 | 1/2001 |
| WO | WO 02/42292 A2 | 5/2002 |
| WO | WO 02/072579 A1 | 9/2002 |
| WO | WO 2002100833 | * 12/2002 |
| WO | WO 03/032989 A1 | 4/2003 |
| WO | WO 03/051847 A1 | 6/2003 |

OTHER PUBLICATIONS

* WO 2002100833 is not provided as it is not used in a rejection against applicants' claims and only cited as closest prior art.*
Jeffrey C Boehm & Jerry L Adams, "New inhibitors of p38 kinase, Monthly Focus: Pulmonary-Allergy, Dermatological, Gastrointestional & Arthritis," 2000, pp. 25-37.
Raymond J. Owens and Simon Lumb, "Therapeutic regulation of cytokine signalling by inhibitors of p38 mitogen-activated protein kinase," Novel Cytokine Inhibitors, Ed. Gerry A. Higgs. and Brian Henderson, 2000, pp. 201-211.
Salituro, E.G., et al. "Inhibitors of p38 MAP Kinas: Therapeutic Intervention in Cytokine-Mediated Diseases," Current Medicinal Chemistry, 1999, 607-823.
Foster, M.L., et al., "Potential of p38 Inhibitors in the Treatment of Rheumatoid Arthritis," Drug News Perspect 13 (8), Oct. 2000. pp. 488-496.
Boehm, J.D. and Adams, J.L. "Expert Opinion on Therapeutic Patents," 10:25-37 (2000).
Natarajan, Swaminathan R., et al. "P38 MAP Kinase Inhibitors. Part 1: Design and Development of a New Class of Potent and Highly Selective Inhibitors Based on 3,4-Dihydropyrido, [3,2-d 1 Pyrimidone Scaffold," Bioganic & Medicinal Chemistry Letters 13:273-276 (2003).
Judith Branger, et al., "Anti-Imfammatory Effects of a p38 Mitogen-Activiated Protein Kinas Inhibitor During Human Endotoxemia,"[1] Journal of Immunology 168: 4070-4077 (2002).
PCT Search Report mailed Sep. 1, 2004 in PCT/US04/05693.
Database CAS ONLINE on STN, Chem. Abstr. Accession No. 2002:964330, "Preparation of heterocyclic compounds as Rho-kinase inhibitors". WO 2002100844 A1 (Sumitomo Pharmaceuticals Company, Limited, Japan) Dec. 19, 2002, abstract.

* cited by examiner

*Primary Examiner*—Kamal A. Saeed
*Assistant Examiner*—Rebecca Anderson
(74) *Attorney, Agent, or Firm*—Viksnins Harris & Padys PLLP

(57) ABSTRACT

This invention relates to inhibitors of p38, and methods for producing these inhibitors. The invention also provides pharmaceutical compositions comprising the inhibitors of the invention and methods of utilizing the inhibitors and pharmaceutical compositions in the treatment and prevention of various disorders mediated by p38.

16 Claims, 42 Drawing Sheets

15a

OsO₄
CH₃NO
CH₂Cl₂

14a

16a

NaIO₄ on silica gel

CH₂Cl₂

15a

16a

8b

TFA
CH₂Cl₂

7b-3

P38 INHIBITORS AND METHODS OF USE THEREOF

BACKGROUND OF THE INVENTION

1. Field of the Invention

This invention relates to novel inhibitors of p38 MAP kinase and related kinases, pharmaceutical compositions containing the inhibitors, and methods for preparing these inhibitors. They are useful for the treatment of inflammation, osteoarthritis, rheumatoid arthritis, psoriasis, Crohn's disease, inflammatory bowel disease, cancer, autoimmune diseases, and for the treatment of other cytokine-mediated diseases.

2. Description of the State of the Art

A number of chronic and acute inflammatory conditions have been associated with the overproduction of pro-inflammatory cytokines. Such cytokines include but are not limited to tumor necrosis factor alpha (TNF-α), interleukin 1 beta (IL-1β), interleukin 8 (IL-8) and interleukin 6 (IL-6). Rheumatoid Arthritis (RA) is a chronic disease where TNF-α and IL-1β are implicated in the onset of the diseases and in the progression of the bone and joint destruction seen with this debilitating condition. Recently approved therapeutic treatments for RA have included soluble TNF-α receptor (etanercept) and IL-1 receptor antagonist (anakinra). These treatments work by blocking the ability of their respective cytokines to bind to their natural receptors. Alternative methods to treat cytokine-mediated diseases are currently under investigation. One such method involves inhibition of the signaling pathway that regulates the synthesis and production of pro-inflammatory cytokines like p38.

P38 (also CSBP or RK) is a serine/threonine mitogen-activated protein kinase (MAPK) that has been shown to regulate pro-inflammatory cytokines. P38 was first identified as a kinase which became tyrosine phosphorylated in mouse monocytes following treatment with lipopolysaccharide (LPS). A link between p38 and the response of cells to cytokines was first established by Saklatvala J., et al., Cell, 78: 1039–1049 (1994), who showed that IL-1 activates a protein kinase cascade that results in the phosphorylation of the small heat shock protein, Hsp27, probably by mitogen-activated protein activated protein kinase 2 (MAPKAP kinase-2). Analysis of peptide sequences derived from the purified kinase indicated that it was related to the p38 MAPK activated by LPS in mouse monocytes, Han, J., et al., Science, 265: 808–811 (1994). At the same time it was shown that p38 MAPK was itself activated by an upstream kinase in response to a variety of cellular stresses, including exposure to UV radiation and osmotic shock, and the identity of the kinase that directly phosphorylates Hsp27 was confirmed as MAPKAP kinase-2, Rouse, J., et al., Cell, 78: 1027–1037 (1994). Subsequently, workers at Smith-Kline Beecham showed that p38 MAPK was the molecular target of a series of pyridinylimidazole compounds that inhibited the production of TNF from LPS-challenged human monocytes, Lee, J., et al., Nature, 372: 739–746. This was a key discovery and has led to the development of a number of selective inhibitors of p38 MAPK and the elucidation of its role in cytokine signaling.

It is now known that multiple forms of p38 MAPK (α, β, γ, δ), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNF-α. P38 functions by phosphorylating downstream substrates that include other kinases and transcription factors. Agents that inhibit p38 kinase have been shown to block the production of cytokines including but not limited to TNF-α, IL-6, IL-8 and IL-1β in vitro and in vivo models Adams, J. L., et al., Progress in Medicinal Chemistry, 38: 1–60 (2001).

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. Lee, J. C., et al., Int. J. Immunopharmacol., 10: 835–843 (1988). The efficacy of p38 inhibitors in animal models of inflammatory disease has prompted an investigation of the underlying mechanism(s) which could account for the effect of these inhibitors. The role of p38 in the response of cells to IL-1 and TNF has been investigated in a number of cells systems relevant to the inflammatory response using a pyridinyl imidazole inhibitor: endothelial cells and IL-8, Hashimoto, S., et al., J. Pharmacol. Exp. Ther., 293: 370–375 (2001), fibroblasts and IL-6/GM-CSF/PGE2 Beyaert, R., et al., EMBO J., 15: 1914–1923 (1996), neutrophils and IL-8 Albanyan, E. A., et al., Infect. Immun., 68: 2053–2060 (2000) macrophages and IL-1 Caivano, M. and Cohen, P., J. Immunol., 164: 3018–3025 (2000), and smooth muscle cells and RANTES Maruoka, S., et al., Am. J. Respir. Crit. Care Med., 161: 659–668 (1999). The destructive effects of many disease states are caused by the over production of pro-inflammatory cytokines. The ability of p38 inhibitors to regulate this overproduction makes them excellent candidates for disease modifying agents.

Inhibitors of p38 are active in a variety of widely recognized disease models. Inhibitors of p38 show positive effects in a number of standard animal models of inflammation including rat collagen-induced arthritis, Jackson, J. R., et al., J. Pharmacol. Exp. Ther., 284: 687–692 (1998); rat adjuvant-induced arthritis, Badger, A. M., et al., Arthritis Rheum., 43: 175–183 (2000); Badger, A. M., et al., J. Pharmacol. Exp. Ther., 279: 1453–1461 (1996); and carrageenan-induced paw edema in the mouse, Nishikori, T., et al., Eur. J. Pharm., 451: 327–333 (2002). Molecules that block p38's function have been shown to be effective in inhibiting bone resorption, inflammation, and other immune and inflammation-based pathologies in these animal models. Thus, a safe and effective p38 inhibitor would provide a means to treat debilitating diseases that can be regulated by modulation of p38 signaling like, but not limited to, RA.

P38 inhibitors are well known to those skilled in the art. Reviews of early inhibitors have helped establish the structure activity relationships important for enhanced activity both in vitro and in vivo. See, Salituro, E. G., et al., Current Medicinal Chemistry, 6: 807–823 (1999) and Foster, M. L., et al., Drug News Perspect., 13: 488–497 (2000). More contemporary reviews have focused on the structural diversity of new inhibitors being explored as p38 inhibitors Boehm, J. D. and Adams, J. L., Exp. Opin. Ther. Patents, 10: 25–37 (2000). This invention describes a novel series of substituted 2-aza-[4.3.0]-bicyclic hereroaromatic compounds as p38 inhibitors that are useful for the treatment of inflammation, osteoarthritis, rheumatoid arthritis, cancer, autoimmune diseases, and for the treatment of other cytokine mediated diseases.

SUMMARY OF THE INVENTION

This invention provides compounds, methods to produce these compounds, and pharmaceutical compositions containing them that inhibit p38 alpha and the associated p38 mediated events such as the inhibition of cytokine production. Such compounds, generally referred to as 2-aza-[4.3.0] bicyclic heteroaromatic rings, have utility as therapeutic agents for diseases that can be treated by the inhibition of the p38 signaling pathway. In general, the invention relates to p38 inhibitors of the general Formula I:

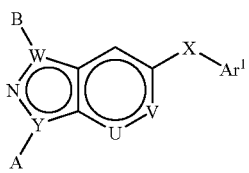

I wherein Y is C, N;

W is C, N, S, or O, provided that W is N, S, or O when Y is C, and W is C or N when Y is N;

U is CH or N;

V is C-E or N;

X is O, S, SO, $SO_2$, $NR^7$, C=O, $CHR^7$, —C=$NOR^1$, —C=$CHR^1$, or $CHOR^1$;

$R^1$ is H, $PO_3H_2$, $SO_3H_2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

Z is alkylene having from 1 to 4 carbons, or alkenylene or alkynylene each having from 2 to 4 carbons, wherein said alkylene, alkenylene, or alkynylene may be substituted or unsubstituted;

$R^7$ is H or substituted or unsubstituted methyl;

$Ar^1$ is substituted or unsubstituted aryl or heteroaryl;

A is H, OH, an amine protecting group, $Z_n$-$NR^2R^3$, $Z_n$-$NR^2$(C=O)$R^2$, $Z_n$-$SO_2R^2$, $Z_n$-$SOR^2$, $Z_n$-$SR^2$, $Z_n$-$OR^2$, $Z_n$-(C=O)$R^2$, $Z_n$-(C=O)$OR^2$, $Z_n$-O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;

B is H, $NH_2$, or substituted or unsubstituted methyl;

E is H, $Z_n$-$NR^2R^3$, $Z_n$-(C=O)$R^4$, $Z_n$-(C=O)$R^5$, $Z_n$-$NR^5$(C=O)$R^5$, $Z_n$-O(C=O)$R^5$, $Z_n$-$OR^5$, $Z_n$-$SO_2R^5$, $Z_n$-$SOR^5$, $Z_n$-$SR^5$, $Z_n$-NH(C=O)$NHR^5$, or $R^5$;

$R^4$ is a substituted or unsubstituted natural or unnatural amino acid, a protected natural or unnatural amino acid, NH(CHR$^6$)(CH$_2$)$_m$OR$^5$ where m is an integer from 1 to 4, or $NR^2R^3$;

$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

$R^6$ is a natural amino acid side chain, $Z_n$-$NR^2R^3$, $Z_n$-$OR^5$, $Z_n$-$SO_2R^5$, $Z_n$-$SOR^5$, or $Z_n$-$SR^5$; and n is 0 or 1, provided that when B is H and A is CH=CH—$R^8$ where $R^8$ is a substituted or unsubstituted alkyl, alkenyl, cycloalkyl, heterocycloalkyl, aryl, or heteroaryl, then X—$Ar^1$ is a substituent where $Ar^1$ is other than substituted or unsubstituted aryl, heteroaryl, NH-alkyl, NH-cycloalkyl, NH-heterocycloalkyl, NH-aryl, NH-heteroaryl, NH-alkoxy, or NH-dialkylamide when X is O, S, C=O, S=O, C=$CH_2$, $CO_2$, NH, or N($C_1$–$C_8$-alkyl).

The invention is also directed to pharmaceutically acceptable prodrugs, pharmaceutically active metabolites, and pharmaceutically acceptable salts of the compound of Formula I. Methods of making the compounds of Formula I are also described.

In another embodiment, this invention relates to compounds of the general Formula II:

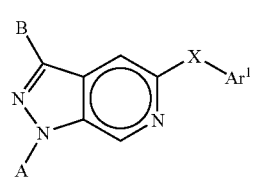

II where A, B, X and $Ar^1$ are as defined above.

In another embodiment, this invention relates to compounds of the general Formula III:

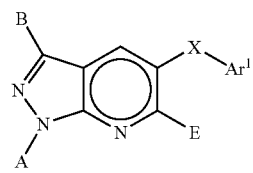

III where A, B, X, E and $Ar^1$ are as defined above.

In another embodiment, this invention relates to compounds of the general Formula IV:

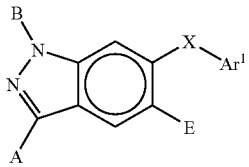

where A, B, X, E and Ar¹ are as defined above, provided that when B is H and A is CH=CH—R⁸ where R⁸ is a substituted or unsubstituted alkyl, alkenyl, cycloalkyl, heterocycloalkyl, aryl, or heteroaryl, then X—Ar¹ is a substituent where Ar¹ is other than substituted or unsubstituted aryl, heteroaryl, NH-alkyl, NH-cycloalkyl, NH-heterocycloalkyl, NH-aryl, NH-heteroaryl, NH-alkoxy, or NH-dialkylamide when X is O, S, C=O, S=O, C=CH₂, CO₂, NH, or N(C₁–C₈-alkyl).

In another embodiment, this invention relates to compounds of the general Formula V:

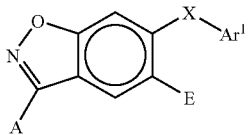

where A, X, E and Ar¹ are as defined above.

In another embodiment, this invention relates to compounds of the general Formula VI:

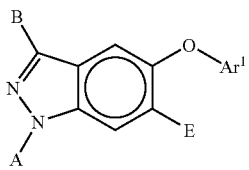

where A, B, E and Ar¹ are as defined above.

In another embodiment, this invention relates to compounds of the general Formula VII:

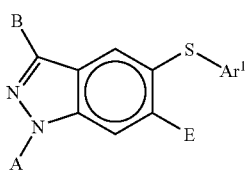

where A, B, E and Ar¹ are as defined above.

In another embodiment, this invention relates to compounds of the general Formula VIII:

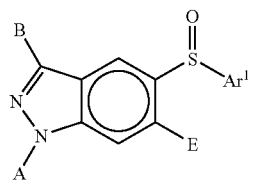

where A, B, E and Ar¹ are as defined above.

In another embodiment, this invention relates to compounds of the general Formula IX:

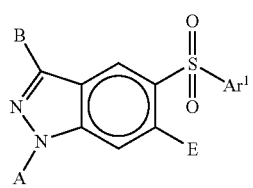

where A, B, E and Ar¹ are defined as above.

In another embodiment, this invention relates to compounds of the general Formula X:

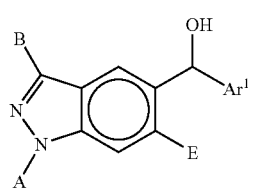

where A, B, E and Ar¹ are defined as above.

In another embodiment, this invention relates to compounds of the general Formula XI:

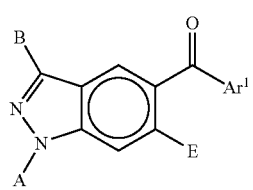

where A, B, E and Ar¹ are defined as above.

In another embodiment, this invention relates to compounds of the general Formula XII:

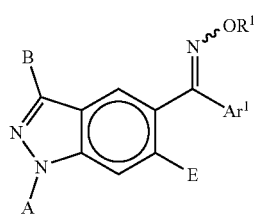

where A, B, E, R¹ and Ar¹ are defined as above.

In another embodiment, this invention relates to compounds of the general Formula XIII:

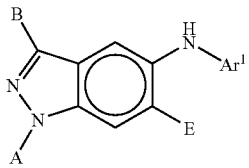

XIII where A, B, E and $Ar^1$ are defined as above.

In another embodiment, this invention relates to ether compounds of the general Formula XIV:

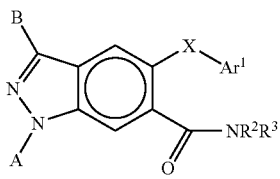

where A, B, X, $Ar^1$, $R^2$ and $R^3$ are defined as above.

In another embodiment, this invention relates to compounds of the general Formula XV:

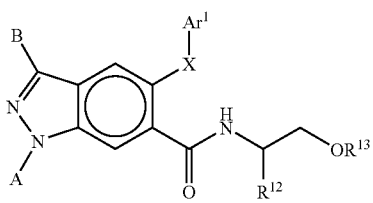

XV where A, B, X, and $Ar^1$ are defined as above, and $R^{12}$ and $R^{13}$ are independently alkyl, allyl, alkenyl, alkynyl, cycloalkyl, heterocycloalkyl, aryl, or heteroaryl, wherein said alkyl, allyl, alkenyl, alkynyl, cycloalkyl, heterocycloalkyl, aryl, or heteroaryl may be substituted or unsubstituted.

In another embodiment, this invention relates to compounds of the general Formula XVI:

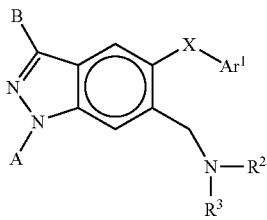

XVI where A, B, X, $R^2$, $R^3$, and $Ar^1$ are defined as above.

In a further aspect the present invention provides compounds that inhibit the production of cytokines such as TNF-α, IL-1, IL-6 and IL-8 comprising compounds of Formulas I–XVI.

In a further aspect the present invention provides a method of treating diseases or medical conditions mediated by cytokines which comprises administering to a warm-blooded animal an effective amount of a compound of Formula I–XVI, or a pharmaceutically acceptable salt or in vivo cleavable prodrug thereof.

In a further aspect the present invention provides a method of inhibiting the production of cytokines such as TNF-α, IL-1, IL-6 and IL-8 which comprises administering to a warm-blooded animal an effective amount of a compound of Formula I–XVI, or a pharmaceutically acceptable salt or in vivo cleavable prodrug thereof.

In a further aspect the present invention provides a method of providing a p38 kinase inhibitory effect comprising administering to a warm-blooded animal an effective amount of a compound of Formula I–XVI, or a pharmaceutically-acceptable salt or in vivo cleavable prodrug thereof.

In a further aspect the present invention provides treating or preventing a p38-mediated condition, comprising administering an amount of a compound effective to treat or prevent said p38-mediated condition or a pharmaceutical composition comprising said compound, to a human or animal in need thereof, wherein said compound is a compound of Formula I–XVI, or a pharmaceutically-acceptable salt or in vivo cleavable prodrug thereof. The p38-mediated condition that can be treated according to the methods of this invention includes inflammatory disease, autoimmune disease, destructive bone disorder, proliferative disorder, infectious disease, viral disease, or neurodegenerative disease The compounds of this invention are also useful in methods for preventing cell death and hyperplasia and therefore may be used to treat or prevent reperfusion/ischemia in stroke, heart attacks, and organ hypoxia. The compounds of this invention are also useful in methods for preventing thrombin-induced platelet aggregation.

The inventive compounds may be used advantageously in combination with other known therapeutic agents.

The invention also relates to pharmaceutical compositions comprising an effective amount of an agent selected from compounds of Formulas I–XVI or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures:

FIG. 1 shows a reaction scheme for the synthesis of compounds having the generic structure 7a.

FIG. 2 shows a reaction scheme for the synthesis of compound 14a.

FIG. 3 shows a reaction scheme for the synthesis of compound 15a.

FIG. 4 shows a reaction scheme for the synthesis of compound 16a.

FIG. 5 shows a reaction scheme for the synthesis of compound 17a.

FIG. 6 shows a reaction scheme for the synthesis of compound 18a.

DETAILED DESCRIPTION OF THE INVENTION

Figure 1:
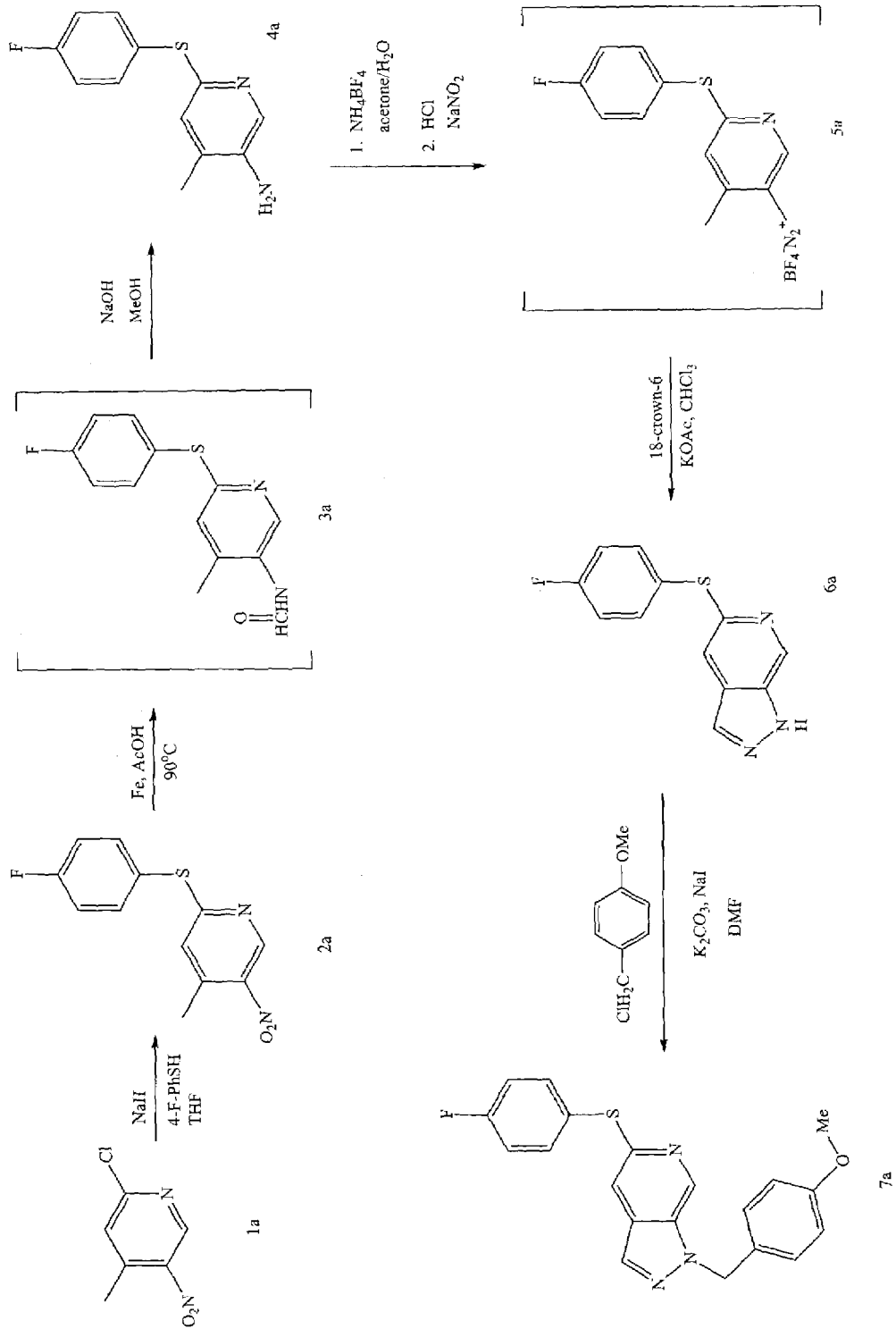

The inventive compounds of the Formulas I–XVI are useful for inhibiting p38 alpha and associated p38 mediated events such as cytokine production. Such compounds have utility as therapeutic agents for diseases that can be treated by the inhibition of the p38 signaling pathway. In general, the invention relates to compounds of the general Formula I:

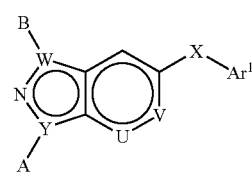

wherein Y is C, N;

W is C, N, S, or O, provided that W is N, S, or O when Y is C, and W is C or N when Y is N;

U is CH or N;

V is C-E or N;

X is O, S, SO, $SO_2$, $NR^7$, C=O, $CHR^7$, —C=$NOR^1$, —C=$CHR^1$, or $CHOR^1$;

$R^1$ is H, $PO_3H_2$, $SO_3H_2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

Z is alkylene having from 1 to 4 carbons, or alkenylene or alkynylene each having from 2 to 4 carbons, wherein said alkylene, alkenylene, or alkynylene may be substituted or unsubstituted;

$R^7$ is H or substituted or unsubstituted methyl;

$Ar^1$ is substituted or unsubstituted aryl or heteroaryl;

A is H, OH, an amine protecting group, $Z_n$-$NR^2R^3$, $Z_n$-$NR^2$(C=O)$R^2$, $Z_n$-$SO_2R^2$, $Z_n$-$SOR^2$, $Z_n$-$SR^2$, $Z_n$-$OR^2$, $Z_n$-(C=O)$R^2$, $Z_n$-(C=O)O$R^2$, $Z_n$-O—(C=O)$R^2$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

$R^2$ and $R^3$ are independently H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted, or $R^2$ together with $R^3$ and N forms a saturated or partially unsaturated heterocycle having 1 or more heteroatoms, wherein said heterocycle may be substituted or unsubstituted and wherein said heterocycle may be fused to an aromatic ring;

B is H, $NH_2$, or substituted or unsubstituted methyl;

E is H, $Z_n$-$NR^2R^3$, $Z_n$-(C=O)$R^4$, $Z_n$-(C=O)$R^5$, $Z_n$-$NR^5$(C=O)$R^5$, $Z_n$-O(C=O)$R^5$, $Z_n$-$OR^5$, $Z_n$-$SO_2R^5$, $Z_n$-$SOR^5$, $Z_n$-$SR^5$, $Z_n$-NH(C=O)$NHR^5$, or $R^5$;

$R^4$ is a substituted or unsubstituted natural or unnatural amino acid, a protected natural or unnatural amino acid, $NH(CHR^6)(CH_2)_mOR^5$ where m is an integer from 1 to 4, or $NR^2R^3$;

$R^5$ is H, OH, an amine protecting group, an alcohol protecting group, an acid protecting group, a thio protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, or $Z_n$-$Ar^1$ may be substituted or unsubstituted;

$R^6$ is a natural amino acid side chain, $Z_n$-$NR^2R^3$, $Z_n$-$OR^5$, $Z_n$-$SO_2R^3$, $Z_nSOR^5$, or $Z_n$-$SR^5$; and n is 0 or 1, provided that when B is H and A is CH=CH—$R^8$ where $R^8$ is a substituted or unsubstituted alkyl, alkenyl, cycloalkyl, heterocycloalkyl, aryl, or heteroaryl, then X—$Ar^1$ is a substituent where $Ar^1$ is other than substituted or unsubstituted aryl, heteroaryl, NH-alkyl, NH-cycloalkyl, NH-heterocycloalkyl, NH-aryl, NH-heteroaryl, NH-alkoxy, or NH-dialkylamide when X is O, S, C=O, S=O, C=$CH_2$, $CO_2$, NH, or N($C_1$–$C_8$-alkyl).

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

"Alkylene" means a linear or branched saturated divalent hydrocarbon radical of one to twelve carbon atoms, e.g., methylene, ethylene, propylene, 2-methylpropylene, pentylene, and the like.

The term "alkenyl" refers to linear or branched-chain monovalent hydrocarbon radical of two to twelve carbon atoms, containing at least one double bond, e.g., ethenyl, propenyl, and the like, wherein the alkenyl radical may be optionally substituted independently with one or more substituents described herein, and includes radicals having "cis" and "trans" orientations, or alternatively, "E" and "Z" orientations.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynyl" refers to a linear or branched monovalent hydrocarbon radical of two to twelve carbon atoms containing at least one triple bond. Examples include, but are not limited to, ethynyl, propynyl, and the like, wherein the alkynyl radical may be optionally substituted independently with one or more substituents described herein.

The term "alkynylene" to a linear or branched divalent hydrocarbon radical of two to twelve carbons containing at least one triple bond, wherein the alkynylene radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heterocycloalkyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below. The radical may be a carbon radical or heteroatom radical. "Heterocycloalkyl" also includes radicals where heterocycle radicals are fused with aromatic or heteroaromatic rings. Examples of heterocycloalkyl rings include, but are not limited to, pyrrolidine, piperidine, piperazine, tetrahydropyranyl, morpholine, thiomorpholine, homopiperazine, phthalimide, and derivatives thereof.

The term "heteroalkenyl" refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The term "heteroallyl" refers to radicals having the formula RC=CHCHR, wherein R is alkyl, alkenyl, alkynyl, cycloalkyl, heterocycloalkyl, aryl, heteroaryl, or any substituent as defined herein, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroallyl may be optionally substituted independently with one or more substituents described herein.

"Aryl" means a monovalent aromatic hydrocarbon monocyclic radical of 6 to 10 ring atoms or a polycyclic aromatic hydrocarbon, optionally substituted independently with one or more substituents described herein. More specifically the term aryl includes, but is not limited to, phenyl, 1-naphthyl, 2-naphthyl, and derivatives thereof.

"Heteroaryl" means a monovalent monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof.

The term "halo" represents fluoro, chloro, bromo or iodo.

"Amino protecting groups" refers to those organic groups intended to protect nitrogen atoms against undesirable reactions during synthetic procedures and include, but are not limited to, benzyl, benzyloxycarbonyl (CBZ), tert-butoxycarbonyl (Boc), trifluoroacetyl, and the like.

"Alcohol protecting groups" refers to those organic groups intended to protect alcohol groups or substituents against undesirable reactions during synthetic procedures and include, but are not limited to, (trimethylsilyl)ethoxymethyl (SEM), tert-butyl, methoxymethyl (MOM), and the like.

"Sulfur protecting groups" refers to those organic groups intended to protect sulfur groups or substituents against undesirable reactions during synthetic procedures and include, but are not limited to, benzyl, (trimethylsilyl)ethoxymethyl (SEM), tert-butyl, trityl and the like.

"Acid protecting groups" refers to those organic groups intended to protect acid groups or substituents against undesirable reactions during synthetic procedures and include, but are not limited to, benzyl, (trimethylsilyl)ethoxymethyl (SEM), methylethyl and tert-butyl esters, and the like.

In general, the various moieties or functional groups of the compounds of Formulas I–XVI may be optionally substituted by one or more substituents. Examples of substituents suitable for purposes of this invention include, but are not limited to, halo, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$ heterocycloalkyl, $Z_n$-OR, $Z_n$-NO2, $Z_n$-CN, $Z_n$-CO2R, $Z_n$-(C=O)R, $Z_n$-O(C=O)R, $Z_n$-O-alkyl, $Z_n$-OAr, $Z_n$-SH, $Z_n$-SR, $Z_n$-SOR, $Z_n$-SOsR, $Z_n$-S—Ar $Z_n$-SOAr, $Z_n$-SO$_2$Ar, aryl, heteroaryl, $Z_n$-Ar, $Z_n$-(C=O)NR$^2$R$^3$, $Z_n$-NR$^2$R$^3$, $Z_n$-NR(C=O)R $Z_n$-SO$_2$ NR$^2$R$^3$, PO$_3$H$_2$, SO$_3$H$_2$, amine protecting groups, alcohol protecting groups, sulfur protecting groups, or acid protecting groups, where:

Z is alkylene having from 1 to 4 carbons, or alkenylene or alkynylene each having from 2 to 4 carbons, wherein said alkylene, alkenylene, or alkynylene may be substituted or unsubstituted;

n is zero or 1,

R$^1$, R$^2$, and R$^3$ are alkyl, allyl, alkenyl, alkynyl, heteroalkyl, heteroallyl, heteroalkenyl, heteroalkynyl, alkoxy, heteroalkoxy, $Z_n$-cycloalkyl, or $Z_n$-heterocycloalkyl, and Ar is aryl or heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, Ar, R$^1$, R$^2$, and R$^3$ may be further substituted or unsubstituted.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formulas I–XVI. The methods for the determination of stereochemistry and the separation of stereoisomers are well known in the art (see discussion in Chapter 4 of "Advanced Organic Chemistry", 4th edition J. March, John Wiley and Sons, New York, 1992).

In addition to compounds of the Formulas I–XVI, the invention also includes solvates, pharmaceutically acceptable prodrugs, pharmaceutically active metabolites, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309–396, edited by K. Widder, et al. (Academic Press, 1985); b) *A Textbook of Drug Design and Development*, edited by Krogsgaard-Larsen and H. Bundgaard, Chapter 5 "Design and Application of Prodrugs", by H. Bundgaard p. 113–191 (1991); c) H. Bundgaard, *Advanced Drug Delivery Reviews*, 8, 1–38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may be prepared using the reaction routes and synthesis schemes as described below, employing the techniques available in the art using starting materials that are readily available.

In addition to compounds of the general Formula I, this invention further includes compounds of the general Formula II:

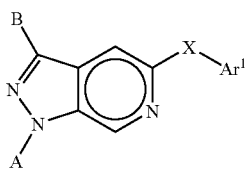

where A, B, X and Ar$^1$ are as defined above.

FIGS. 1–6 show examples of the synthesis of specific compounds having the general Formula II. In one general synthetic process, pyrazole compounds of Formula II are prepared as follows. 2-Chloro-4-methyl-5-nitropyridine is treated with an aryl or heteroaryl phenol or thiophenol and a base such as NaH in a suitable anhydrous solvent. After an appropriate period of time, the reaction mixture is partitioned between an organic solvent and water, and the 2-O-aryl or S-aryl substituted-4-methyl-5-nitro pyridine intermediate compound is isolated from the organic layer. The NO$_2$ substituent is then reduced, for example, by treating with iron powder in acetic acid heating for a period of time, followed by treatment with a suitable base such as NaOH. The resulting aniline intermediate is isolated by extraction of the reaction mixture with an organic solvent. The intermediate aniline compound is then combined with ammonium tetrafluoroborate, followed by the addition of a base such as KOAc and a phase transfer catalyst (e.g., 18-crown-6) to form the bicyclic pyrazole compound of Formula II, where A is hydrogen. To prepare the 1-N-substituted pyrazole compounds of Formula II where A is other than hydrogen, the pyrazole compound is reacted with a suitable base and a compound of the formula RX, where X is halogen and R is alkyl, allyl, alkenyl, alkynyl, allyl, cycloalkyl, heterocycloalkyl, benzyl, or CH$_2$-heteroaryl as defined above.

In another embodiment, this invention relates to compounds of the general Formula III:

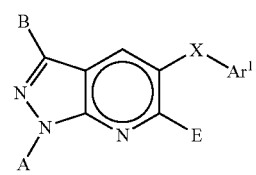

where A, B, X, E and Ar$^1$ are as defined above.

Figure 7:
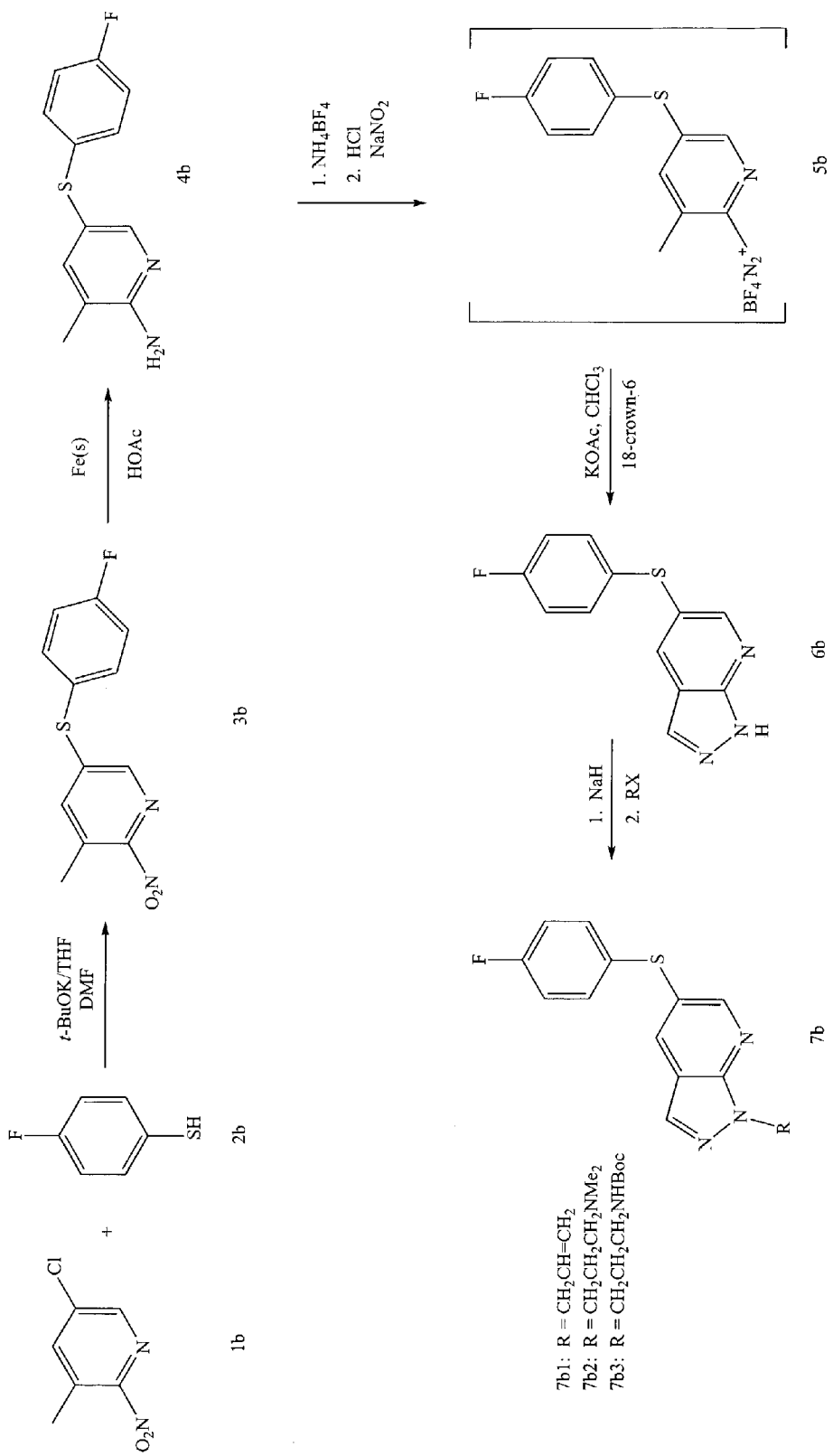
FIG. 7 shows a reaction scheme for the synthesis of compounds having the generic structure 7b.
Figure 8:
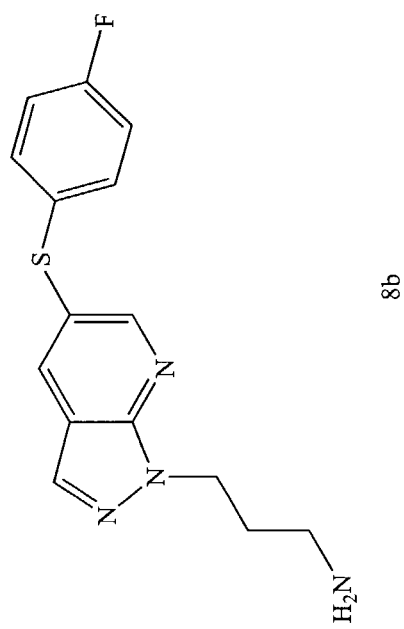
FIG. 8 shows a reaction scheme for the synthesis of compound 8b.
Figure 8:
Figure 8:
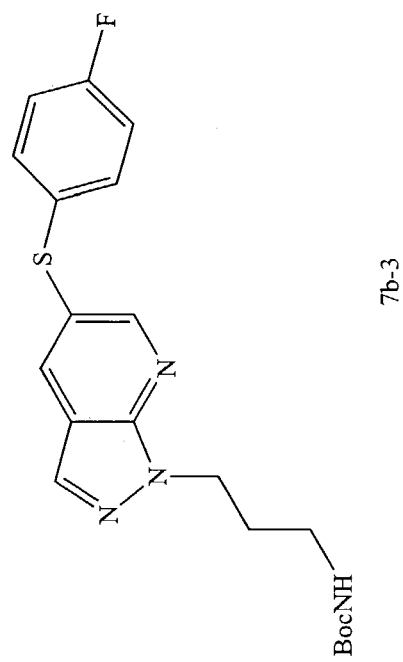

FIGS. 7–8 show examples of the synthesis of specific compounds having the general Formula III. In one general synthetic process, compounds of Formula III are prepared as follows. An aryl thiphenol or aryl phenol is added to a strong base in an anhydrous solvent, and then reacted with 5-chloro-3-methyl-2-nitropyridine to provide a 6-S-aryl- or 6-O-aryl-substituted 2-methyl-3-nitropyridine intermediate compound. The NO$_2$ substituent is reduced, for example, by treating with iron powder in acetic acid heating for a period of time, followed by treatment with a suitable base such as NaOH. The resulting aniline intermediate is isolated by extraction of the reaction mixture with an organic solvent. The intermediate aniline compound is then treated with ammonium tetrafluoroborate followed by the addition of a base such as KOAc and a phase transfer catalyst (e.g., 18-crown-6) to form the bicyclic azaindazole compound of Formula III, where A is hydrogen. To prepare the 1-N-substituted azaindazole compounds of Formula III where A is other than hydrogen, the azaindazole compound is reacted with a suitable base and a compound of the formula RX, where X is halogen and R is alkyl, allyl, alkenyl, alkynyl, cycloalkyl, heterocycloalkyl, benzyl, or CH$_2$-heteroaryl as defined above.

In another embodiment, this invention relates to compounds of the general Formula IV:

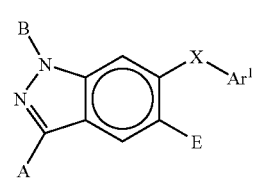

where A, B, X, E and Ar$^1$ are as defined above, provided that when B is H and A is CH=CH—R$^8$ where R$^8$ is a substituted or unsubstituted alkyl, alkenyl, cycloalkyl, heterocycloalkyl, aryl, or heteroaryl, then X—Ar$^1$ is a substituent where Ar$^1$ is other than substituted or unsubstituted aryl, heteroaryl, NH-alkyl, NH-cycloalkyl, NH-heterocycloalkyl, NH-aryl, NH-heteroaryl, NH-alkoxy, or NH-dialkylamide when X is O, S, C=O, S=O, C=CH$_2$, CO$_2$, NH, or N(C$_1$–C$_8$-alkyl)).

FIGS. 9–13 show examples of the synthesis of specific compounds having the general Formula IV. In one general synthetic process, compounds of Formula IV are prepared as follows. 6-Nitroindole is treated with a base and iodine, and the resulting 3-iodo-6-nitroindole is treated with a base and an amine protecting group agent such as trimethylsilylethoxymethyl chloride (SEM-Cl). Treatment of the protected 6-nitroindole compound with trans-2-phenylvinylboronic acid and a suitable catalyst such as Pd(PPh$_3$)$_4$ provides a 1-N-phenylvinyl-6-nitroindole intermediate compound. Reduction of the 6-NO$_2$ substituent with a reducing agent such as hydrazine and a suitable catalyst (e.g., palladium on carbon) provides the 1-N-substituted-6-aminoindole derivative. Treatment of this derivative with sodium nitrite followed by addition of sodium iodide and iodine provides the 1-N-protected-3-phenylvinyl-6-iodoindazole derivative. Treatment of this derivative with oxidizing agent(s) such as osmium tetroxide and sodium periodate provides the 1-N-protected 3-carbaldehyde-6-iodoindazole derivative. This derivative can then be used in a number of synthetic processes to provide various indazole compounds of this invention such as described in the Examples.

In an alternative synthetic process, 6-OAr-substituted compounds of Formula IV are prepared as follows. Treatment of 2-fluoro-4-hydroxyacetophenone with a suitable phenol protecting group reagent, followed by the addition of hydrazine with heating to induce cyclization provides an indazole compound. The indazole compound is 1-N-protected with a suitable amine protecting group reagent. Removal of the phenol protecting group and treatment with an aryl boronic acid, followed by removal of the amine protecting group affords an 6-OAr-substituted compound of Formula IV.

In an alternative synthetic process, 6-SAr-substituted compounds of Formula IV are prepared as follows. 4-Fluorothiophenol is treated with a strong base such as potassium tert-butoxide, and to the resulting phenoxide is added 2,4-difluoropropiophenone. Addition of hydrazine to the resulting intermediate followed by heating to induce cyclization provides a 6-SAr-substituted compound of Formula IV.

In an alternative synthetic process, 5-OAr- and 5-SAr-substituted compounds of Formula IV are prepared as follows. Esterification of 5-fluoro-2-nitrobenzoic acid, followed by treatment of the resulting ester with a mixture of either ArOH or ArSH and a strong base provides 5-XAr-substituted 2-nitrobenzoic acid methyl ester, where X is O or S. Saponification of this ester, followed by the addition of ammonium hydroxide provides the 2-nitrobenzamide intermediate. The 2-nitrobenzamide is converted to the 2-nitrobenzonitrile intermediate by treatment with oxalyl chloride. Reduction of the nitro substituent, followed by the addition of sodium nitrite provides a 3-amino-5-XAr-substituted indazole compound of Formula IV, where X is O or S.

In an alternative synthetic process, 6-OAr-substituted compounds of Formula IV are prepared as follows. 2-Fluoro-4-hydroxybenzonitrile is combined with an aryl boronic acid, copper acetate and a base to provide the 2-fluoro-4-aryloxybenzonitrile intermediate. A stirred solution of this derivative with hydrazine is refluxed to provide a 3-amino-6-aryloxy indazole compound. This compound can be used as the starting material for the synthesis of 3-amideindazole derivatives using standard amide synthesis chemistry known to those skilled in the art.

In another embodiment, this invention relates to compounds of the general Formula V:

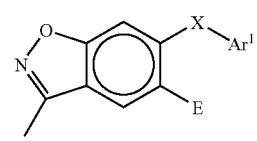

V where A, X, E and Ar$^1$ are as defined above.

Figure 24A:
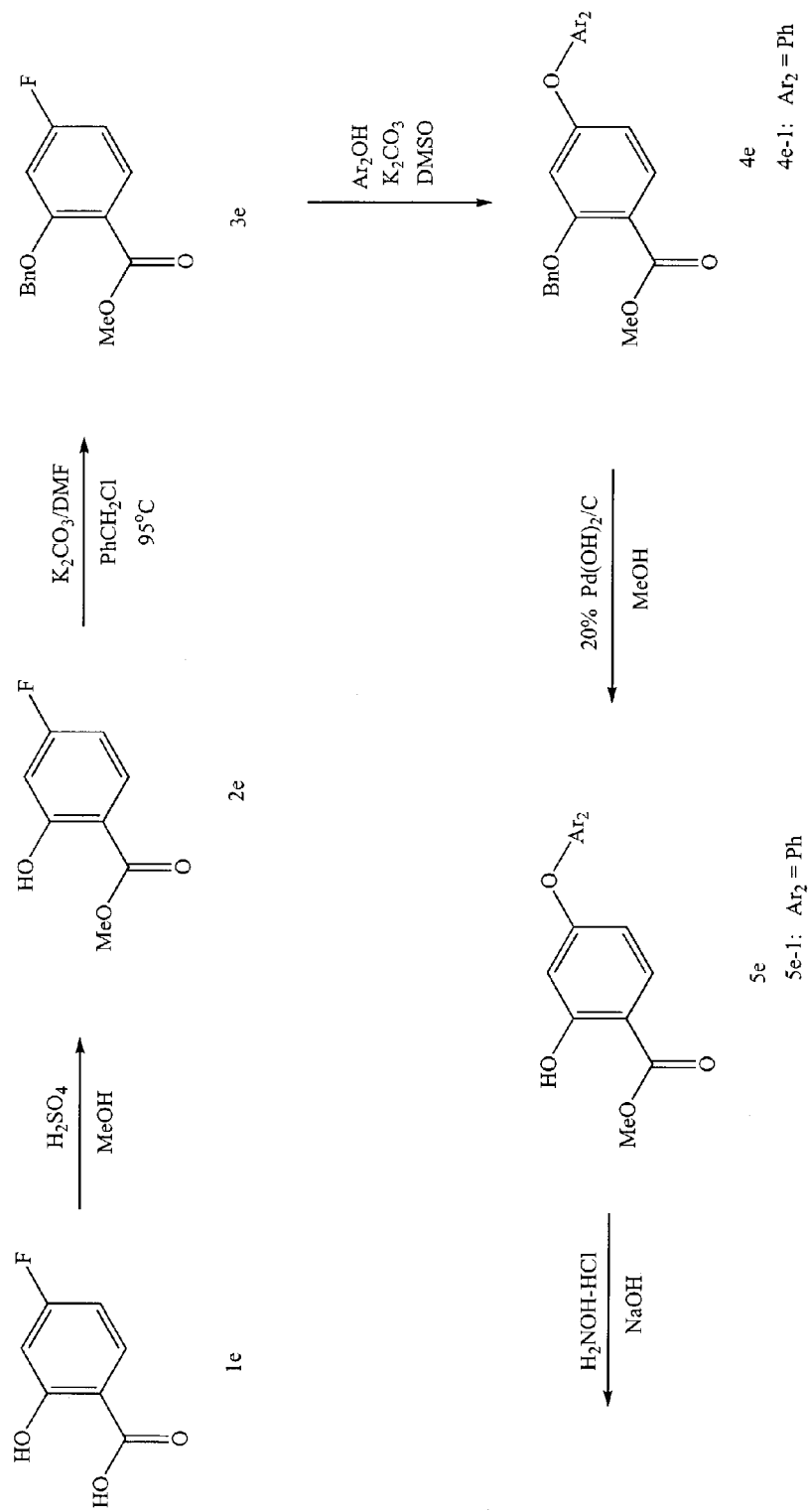
FIGS. 24A–24B show a reaction scheme for the synthesis of compound 8e-1.
Figure 24B:
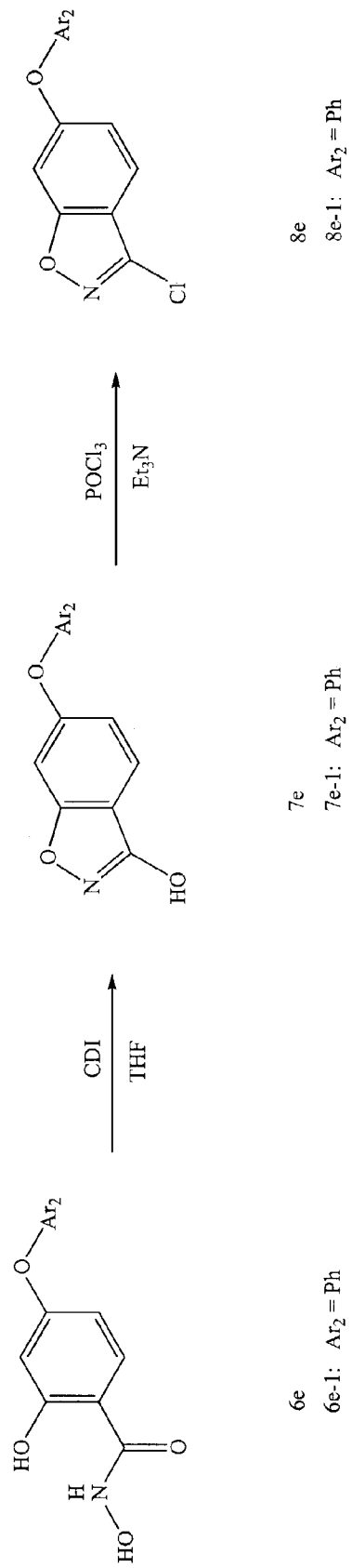
Figure 25:
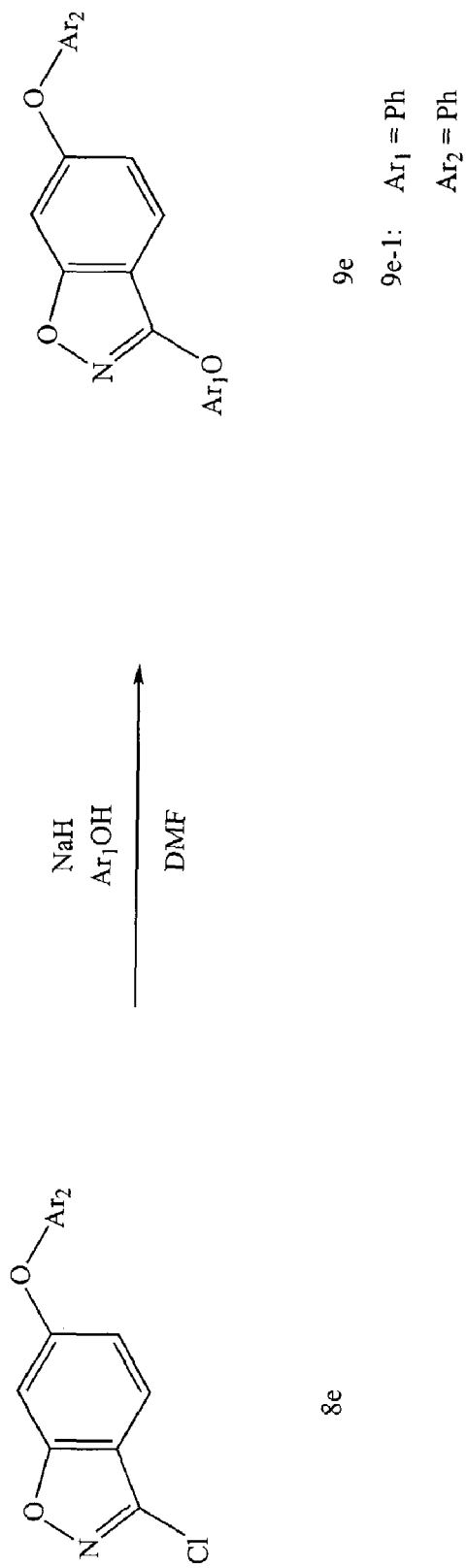
FIG. 25 shows a reaction scheme for the synthesis of compound 9e.
Figure 26:
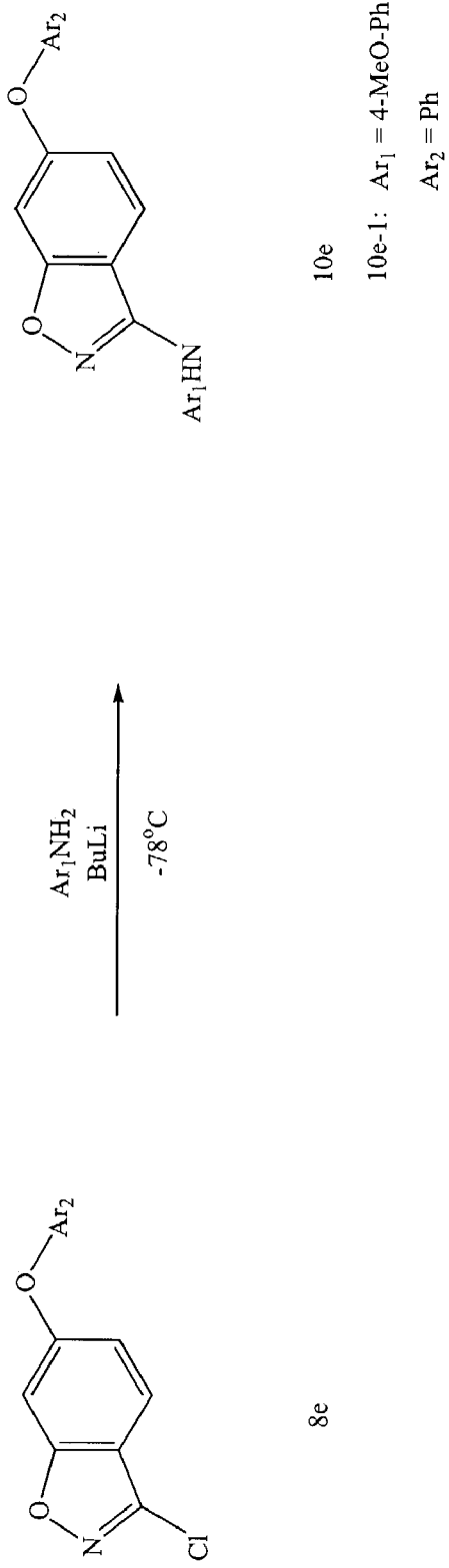
FIG. 26 shows a reaction scheme for the synthesis of compound 10e-1.

FIGS. 24–26 show examples of the synthesis of specific compounds having the general Formula V. In one general synthetic process, compounds of Formula V are prepared as follows. 4-Fluoro-2-hydroxybenzoic acid is esterified and the 2-hydroxy group is protected with a suitable alcohol protecting group. Substitution of the fluoro group with an O—Ar or S—Ar group is effected by treatment with a base and ArOH or ArSH, where Ar is aryl or heteroaryl as defined above. Removal of the alcohol protecting group and saponification of the ester, followed by treatment with carbonyldiimidazole to effect cyclization affords a 6-OAr- or 6-SAr-3-hydroxybenzisoxazole compound. The 3-hydroxybenzisoxazole compound is converted to the 3-chlorobenzisoxazole derivative by treatment with POCl$_3$ and a base. The product can then be used to prepare 3-O—Ar- or 3-NH—Ar-substituted benzisoxazole compounds of this invention. For example, a 6-substituted-3-chlorobenzisoxazole compound can be added to a mixture of ArOH and a strong base (e.g., NaH) to provide a 6-substituted-3-O—Ar-benzisoxazole derivative. In an alternative synthetic process, a 6-substituted-3-chlorobenzisoxazole compound can be added to a mixture of ArNH$_2$ and a strong base to provide a 6-substituted-3-NHAr-benzisoxazole derivative.

In another embodiment, this invention relates to compounds of the general Formulas VI and VII:

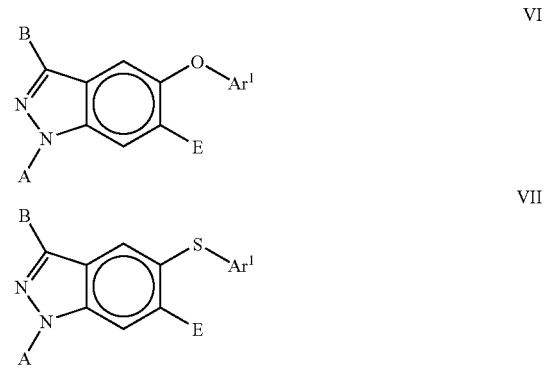

where A, B, E and Ar$^1$ are as defined above.

Figure 14A:
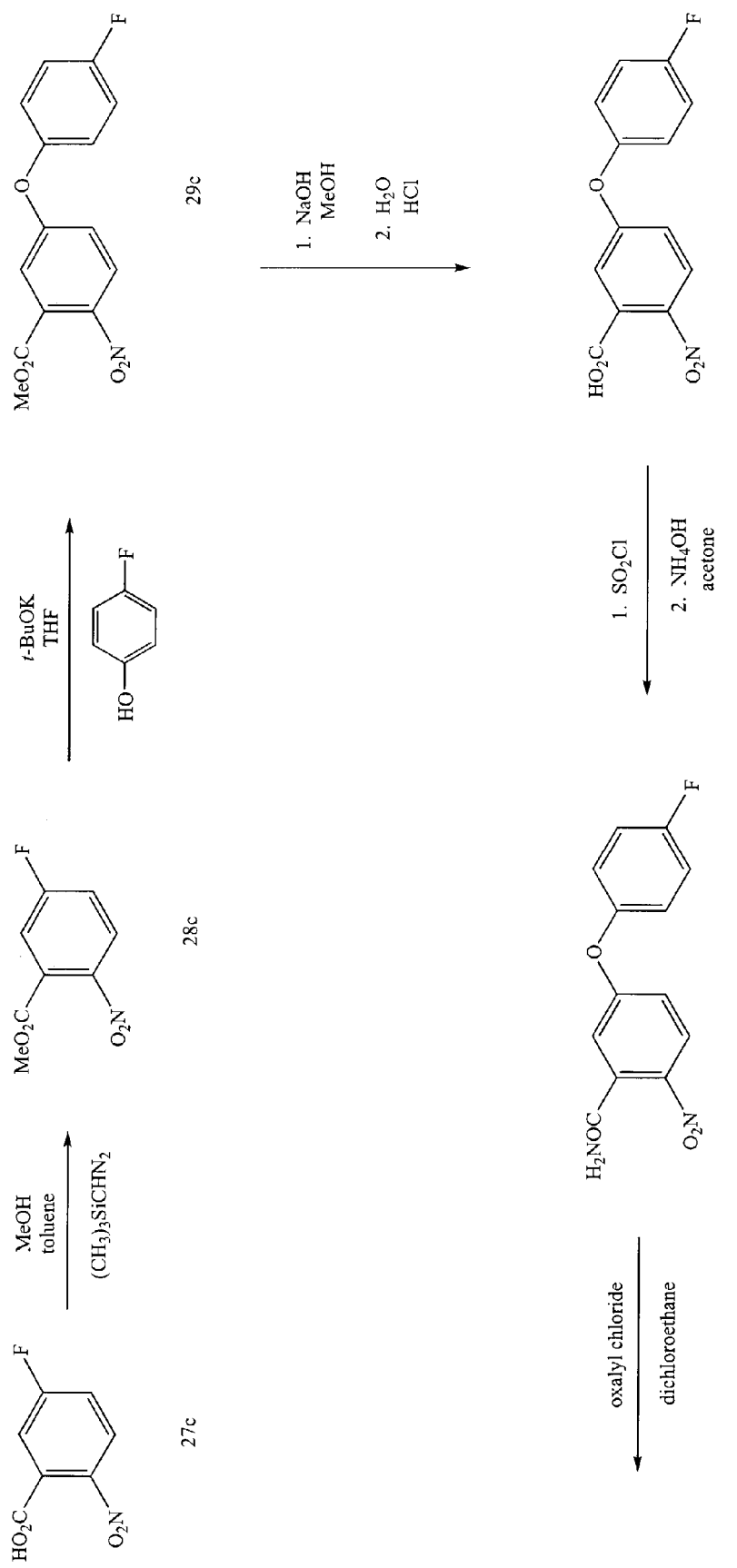
FIGS. 14A–14B show a reaction scheme for the synthesis of compound 34c.
Figure 14B:
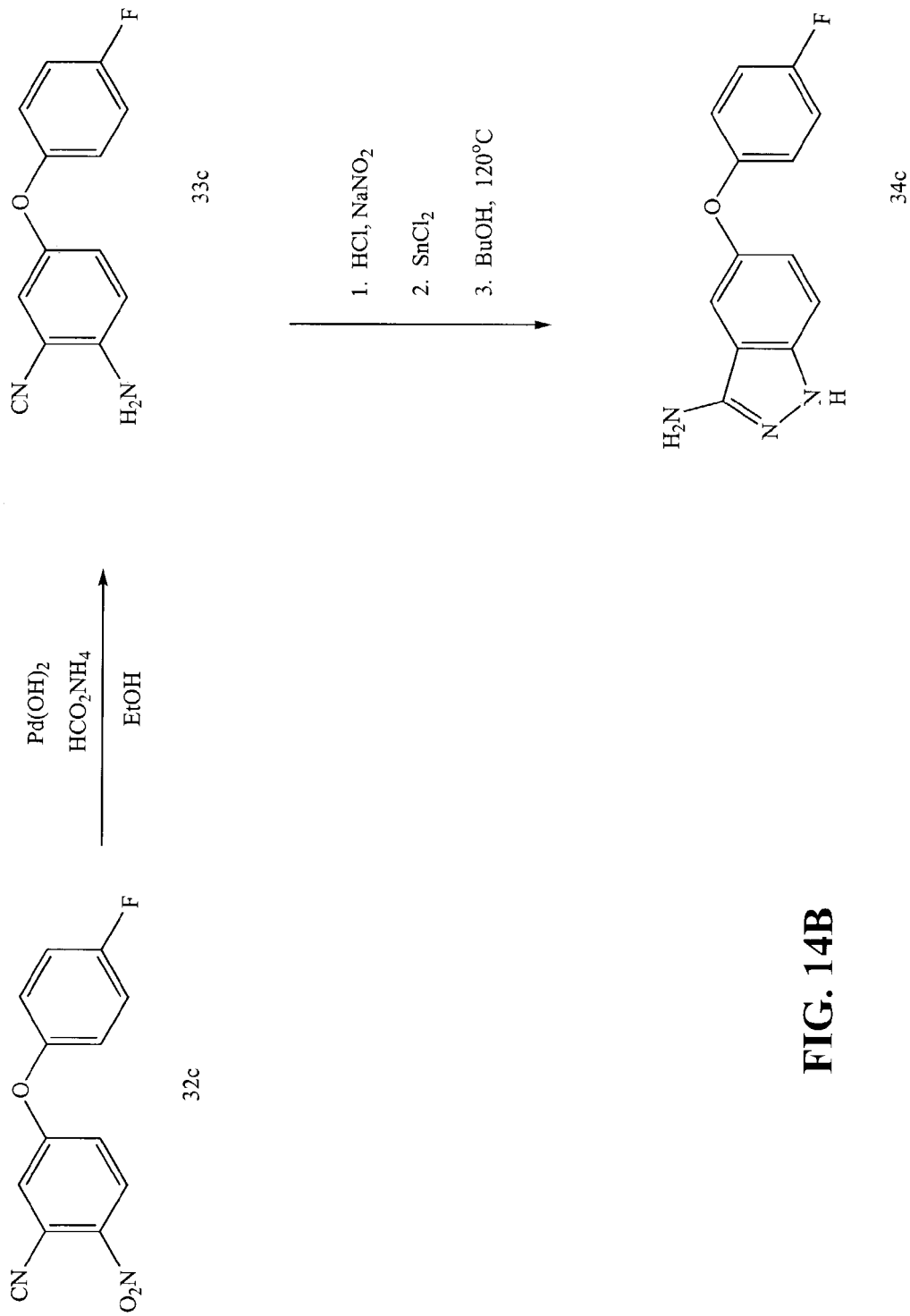
Figure 15:
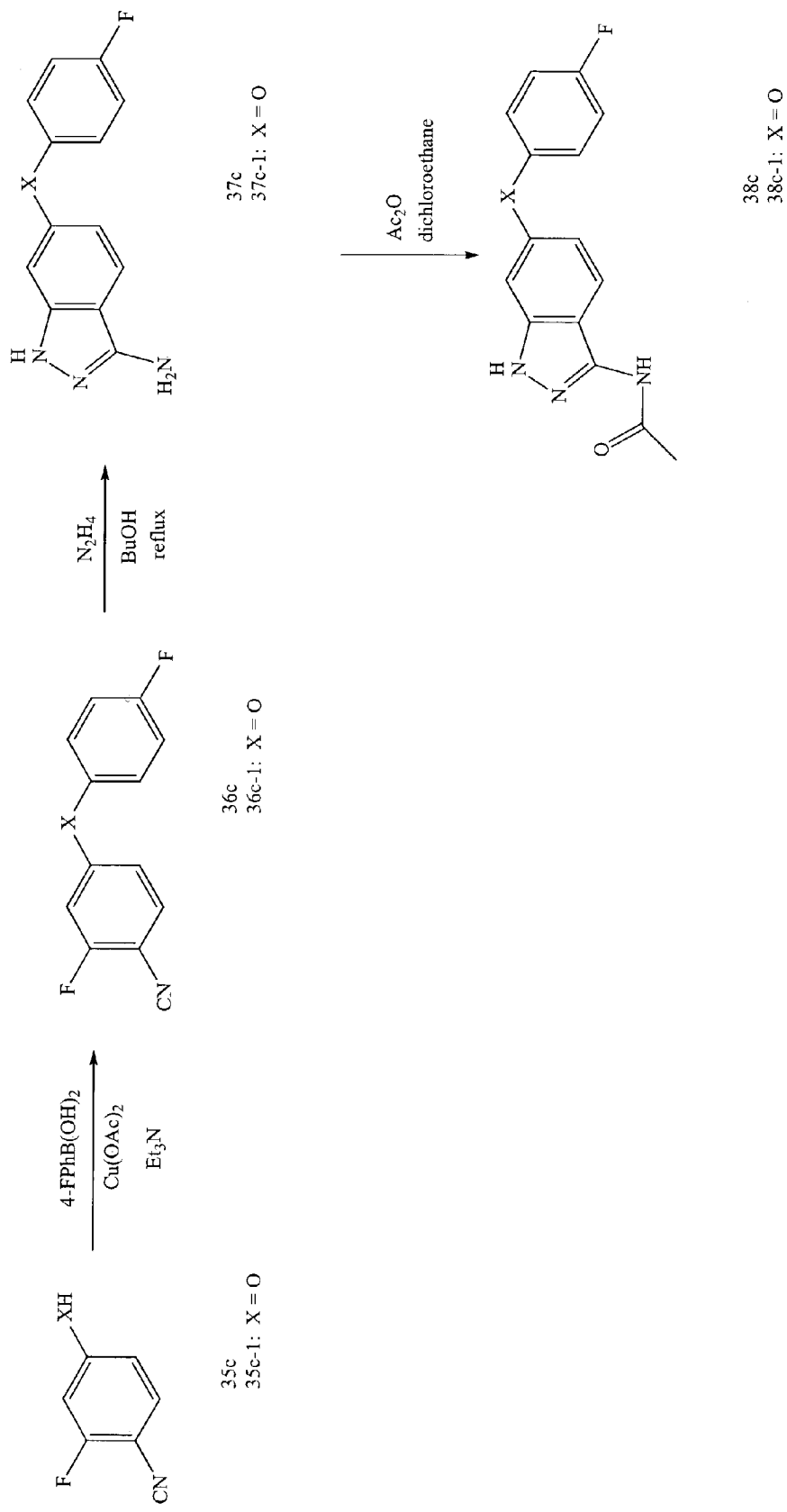
FIG. 15 shows a reaction scheme for the synthesis of compound 38c-1.
Figure 18:
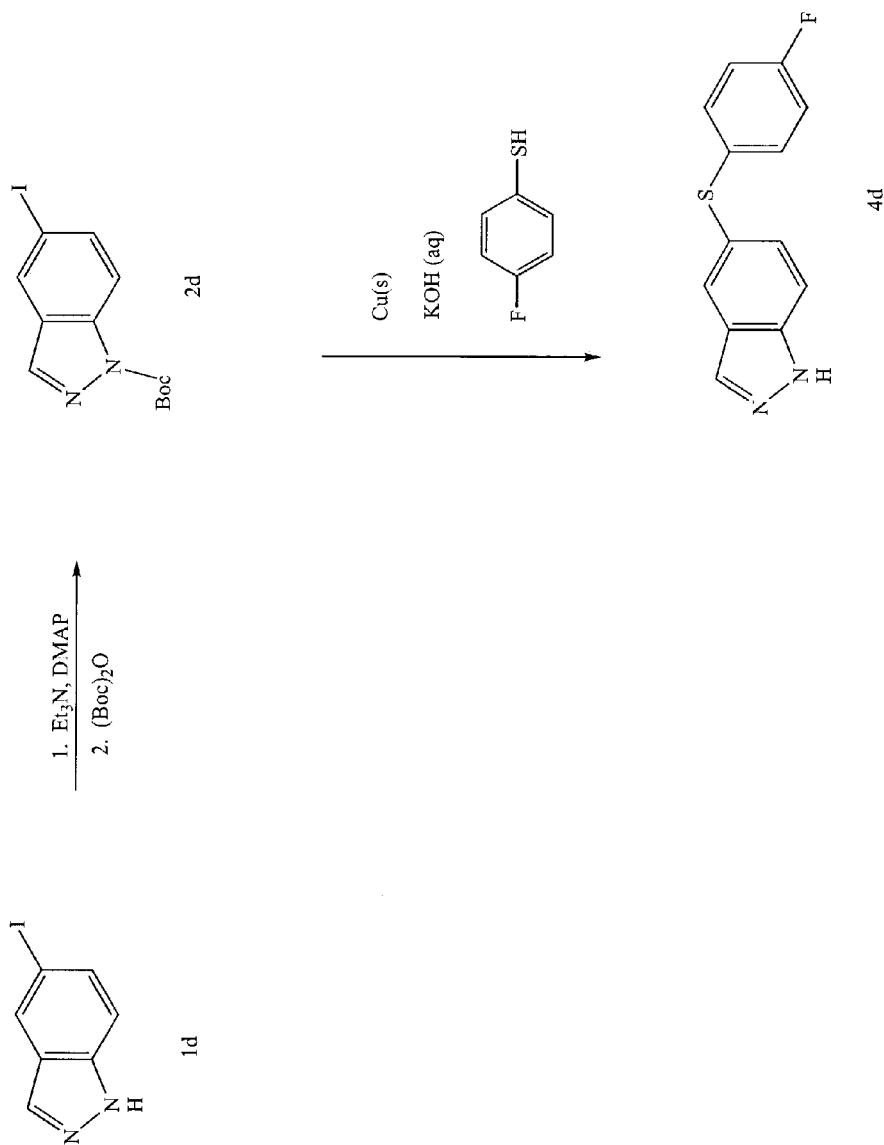
FIG. 18 shows a reaction scheme for the synthesis of compound 4d.
Figure 19:
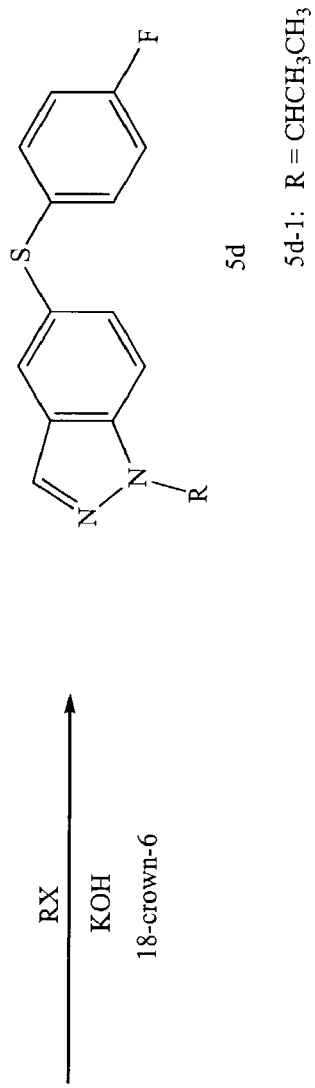
FIG. 19 shows a reaction scheme for the synthesis of compounds having the generic structure 5d.
Figure 19:
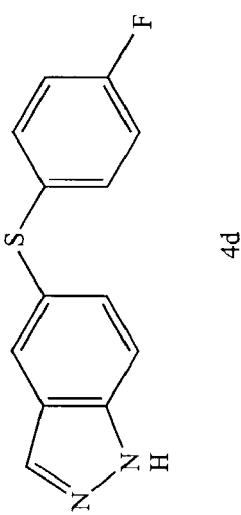
Figure 23:
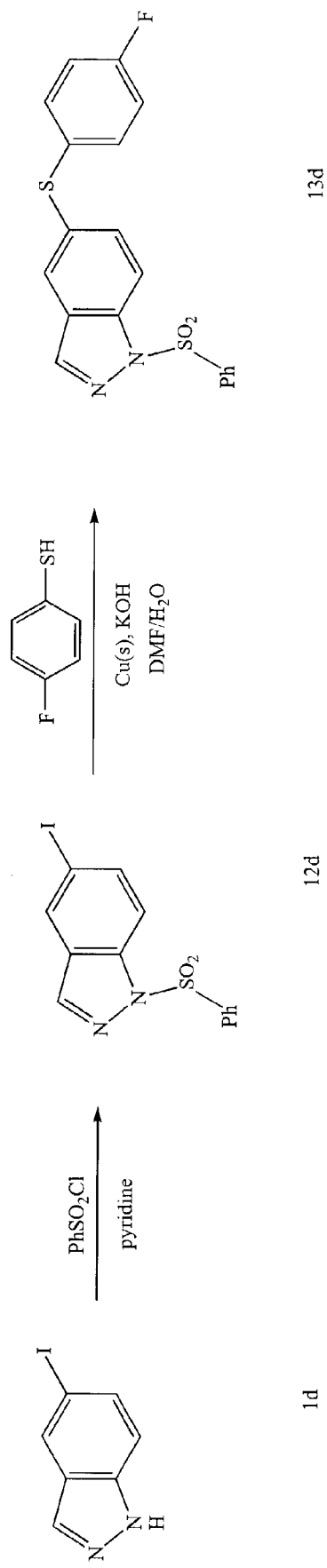
FIG. 23 shows a reaction scheme for the synthesis of compound 13d.

FIGS. 14–15 show examples of the synthesis of specific compounds having the general Formula VI, and FIGS. 18, 19 and 23 show examples of the synthesis of specific compounds having the general Formula VII. In one general synthetic process, compounds of Formulas VI and VII are prepared as follows. 5-Iodo-1H-indazole is prepared by treating 5-amino-1H-indazole with a solution of NaNO$_2$ in water, followed by addition of KI. Following isolation of the product by extraction of the reaction mixture with an organic solvent, the product can be further utilized in various synthetic processes to provide the indazole compounds of this invention. In one process, the 1-amino group of 5-iodo-1H-indazole is protected with a suitable amine protecting group, and the protected 5-iodoindazole is treated with a base, copper powder, and an aryl phenol or aryl thiophenol to provide an 5-O-aryl substituted indazole (Formula VI) or 5-S-aryl substituted indazole (Formula VII). Removal of the amine protecting group provides a compound of this invention having the Formula VI or VII.

In an alternative route, the 5-iodo-1H-indazole is treated with a base and RX or $Ar^1CH_2X$, where R is an alkyl or allyl and Ar1 is an aryl or heteroaryl group as defined above, and X is a halogen or other suitable leaving group. The 1-N-substituted 5-iodoindazole is then treated with a base, copper powder, and an aryl thiophenol or aryl phenol to provide a 5-O-aryl substituted indazole (Formula VI) or 5-S-aryl 1-N-substituted indazole (Formula VII) compound of this invention.

In another embodiment, this invention relates to compounds of the general Formula VIII:

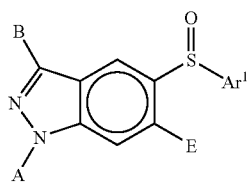

VIII where A, B, E and $Ar^1$ are as defined above.

Figure 22:
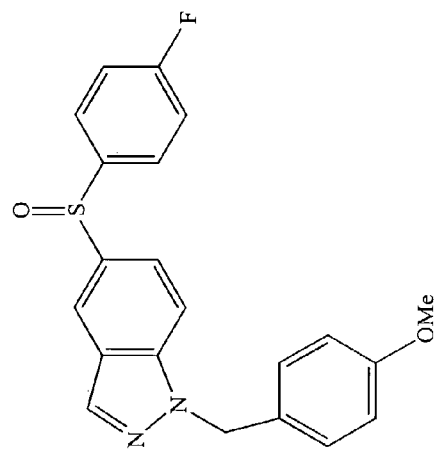
FIG. 22 shows a reaction scheme for the synthesis of compound 11d-1.
Figure 22:
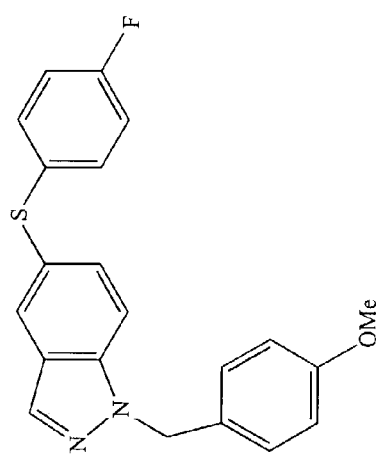

FIG. 22 shows an example of the synthesis of a specific compound having the general Formula VIII. In one general synthetic process, compounds of Formula VIII are prepared by oxidizing a compound of Formula VII with an oxidizing agent that will oxidize the aryl sulfide to the corresponding aryl sulfinyl derivative In another embodiment, this invention relates to compounds of the general Formula IX:

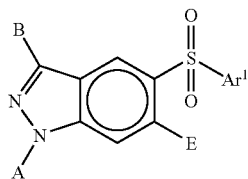

IX where A, B, E and $Ar^1$ are defined as above.

Figure 21:
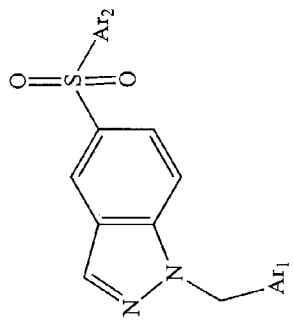
FIG. 21 shows a reaction scheme for the synthesis of compound 10d-1.
Figure 21:
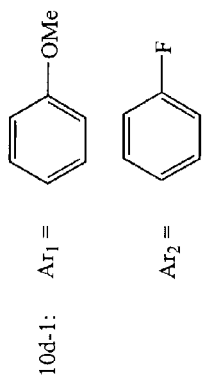
Figure 21:
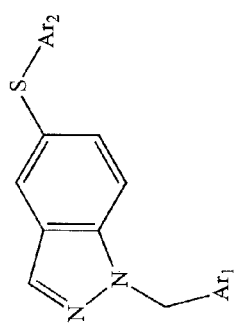
Figure 21:
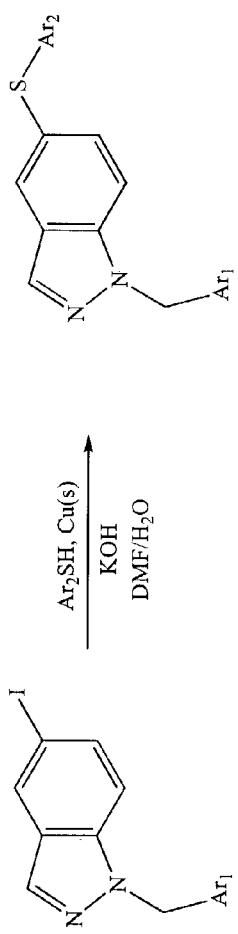

FIG. 21 shows an example of the synthesis of a specific compound having the general Formula IX. In one general synthetic process, compounds of Formula IX are prepared by oxidizing a compound of Formula VII with an oxidizing agent that will oxidize the aryl sulfide to the corresponding aryl sulfonyl derivative In another embodiment, this invention relates to compounds of the general Formula X:

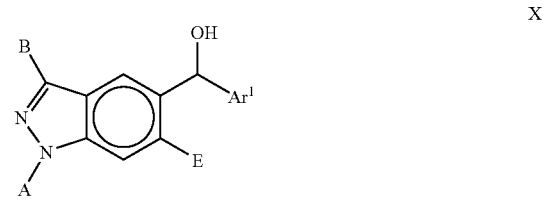

X where A, B, E and $Ar^1$ are defined as above.

Figure 31:
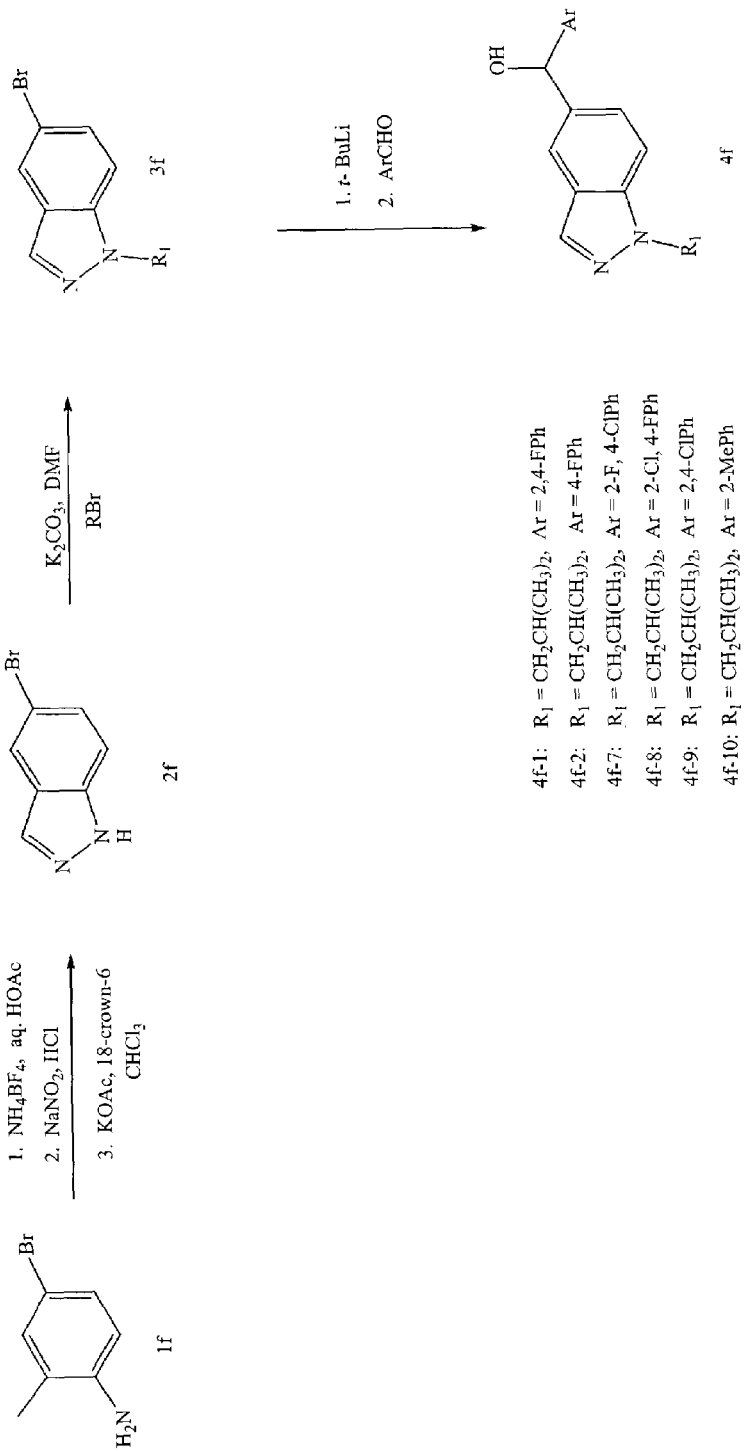
FIG. 31 shows a reaction scheme for the synthesis of compounds having the generic structure 4f.

FIG. 31 shows an example of the synthesis of a specific compound having the general Formula X. In one general synthetic process, compounds of Formula X are prepared as follows. 4-Bromo-2-methyl aniline is added to a mixture of ammonium tetrafluoroborate and acetic acid. After a period of time, sodium nitrite is added to the mixture, followed by the addition of a base such as potassium acetate and a phase-transfer catalyst such as 18-crown-6 to provide 5-bromoindazole. The bromoindazole is treated with RBr in the presence of a base to provide a 1-N-substituted 5-bromoindazole derivative, where R is "A" as defined above for Formula X as defined above with the exception of hydrogen. Treatment of the 1-N-substituted derivative with $Ar^1CHO$ in the presence of a strong base such as butyl lithium, where $Ar^1$ is as defined above, provides an alcohol compound of Formula X.

In another embodiment, this invention relates to compounds of the general Formula XI:

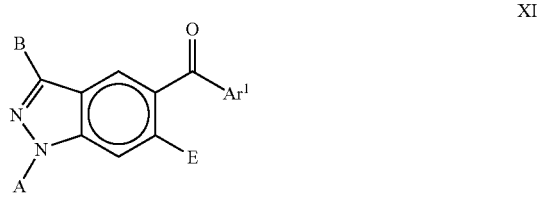

XI where A, B, E and $Ar^1$ are defined as above.

Figure 32:
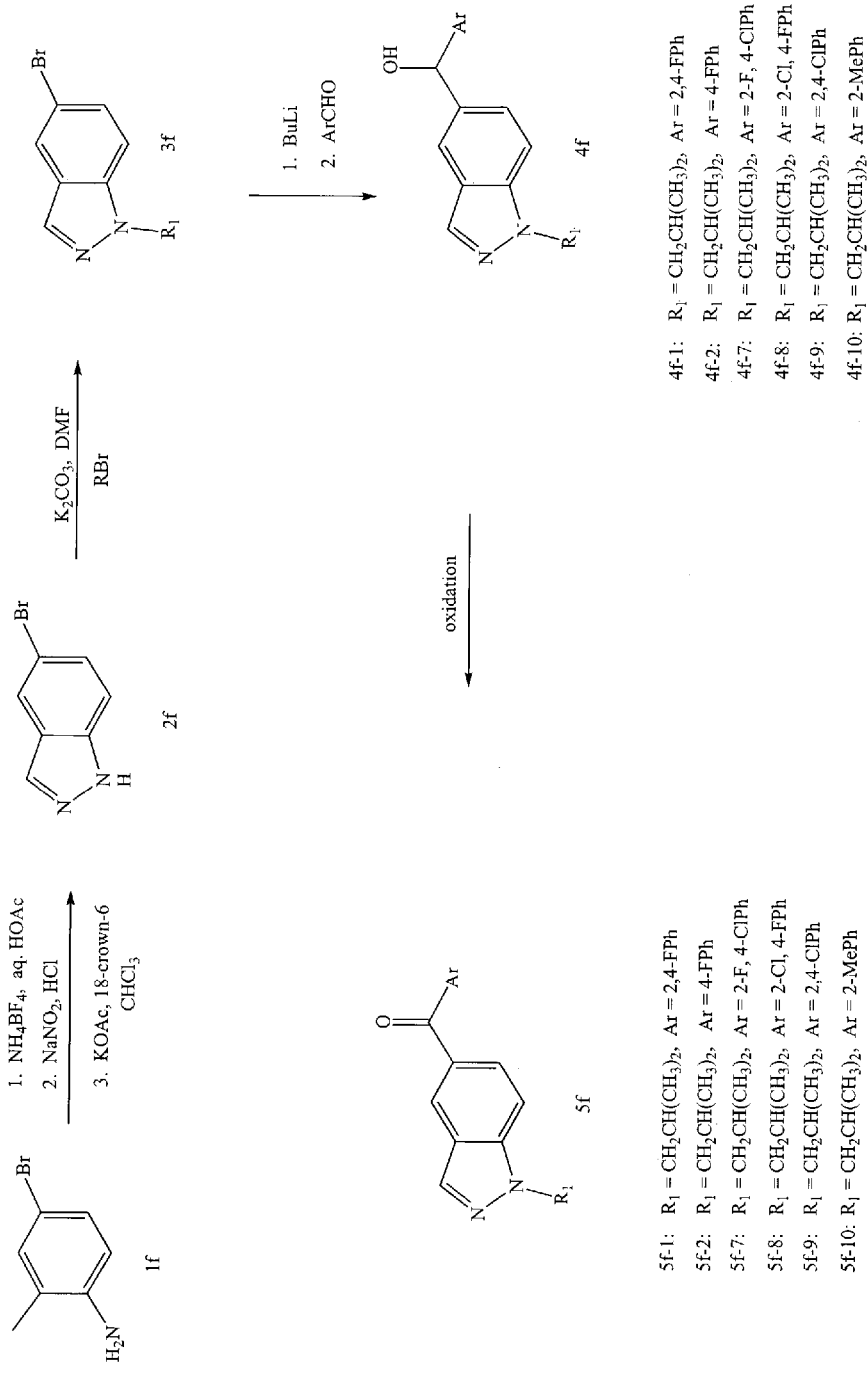
FIG. 32 shows a reaction scheme for the synthesis of compounds having the generic structure 5f.
Figure 33:
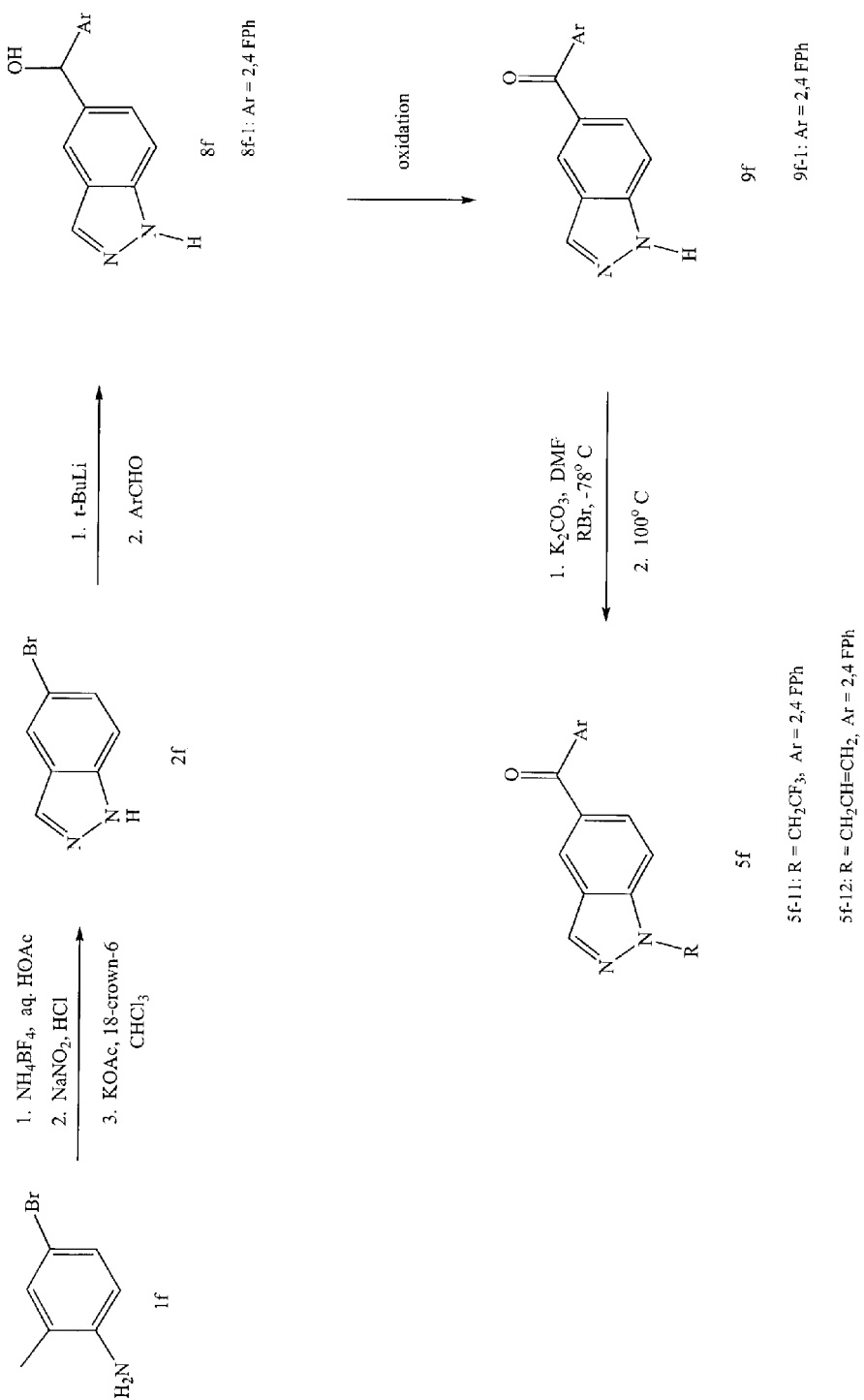
FIG. 33 shows an alternate reaction scheme for the synthesis of compounds having the generic structure 5f.

FIG. 32 shows and example of the synthesis of a specific compound having the general Formula XI. In one general synthetic process, compounds of Formula XI are prepared as follows. 4-Bromo-2-methyl aniline is added to a mixture of ammonium tetrafluoroborate and acetic acid. After a period of time, sodium nitrite is added to the mixture, followed by the addition of a base such as potassium acetate and a phase-transfer catalyst such as 18-crown-6 to provide 5-bromoindazole. The bromoindazole is treated with RBr in the presence of a base to provide a 1-N-substituted 5-bromoindazole intermediate, where R is "A" as defined above for Formula XI as defined above with the exception of hydrogen. Treatment of the 1-N-substituted intermediate with $Ar^1CHO$ in the presence of a strong base such as butyl lithium, where $Ar^1$ is as defined above, followed by treatment with a suitable oxidizing agent to provides the 1-N-substituted compound of Formula XI. An alternative method of synthesizing compound of Formula XI is shown in FIG. 33.

In another embodiment, this invention relates to compounds of the general Formula XII:

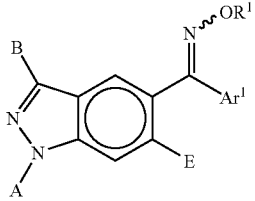

XII where A, B, E, $R^1$ and $Ar^1$ are defined as above.

Figure 27:
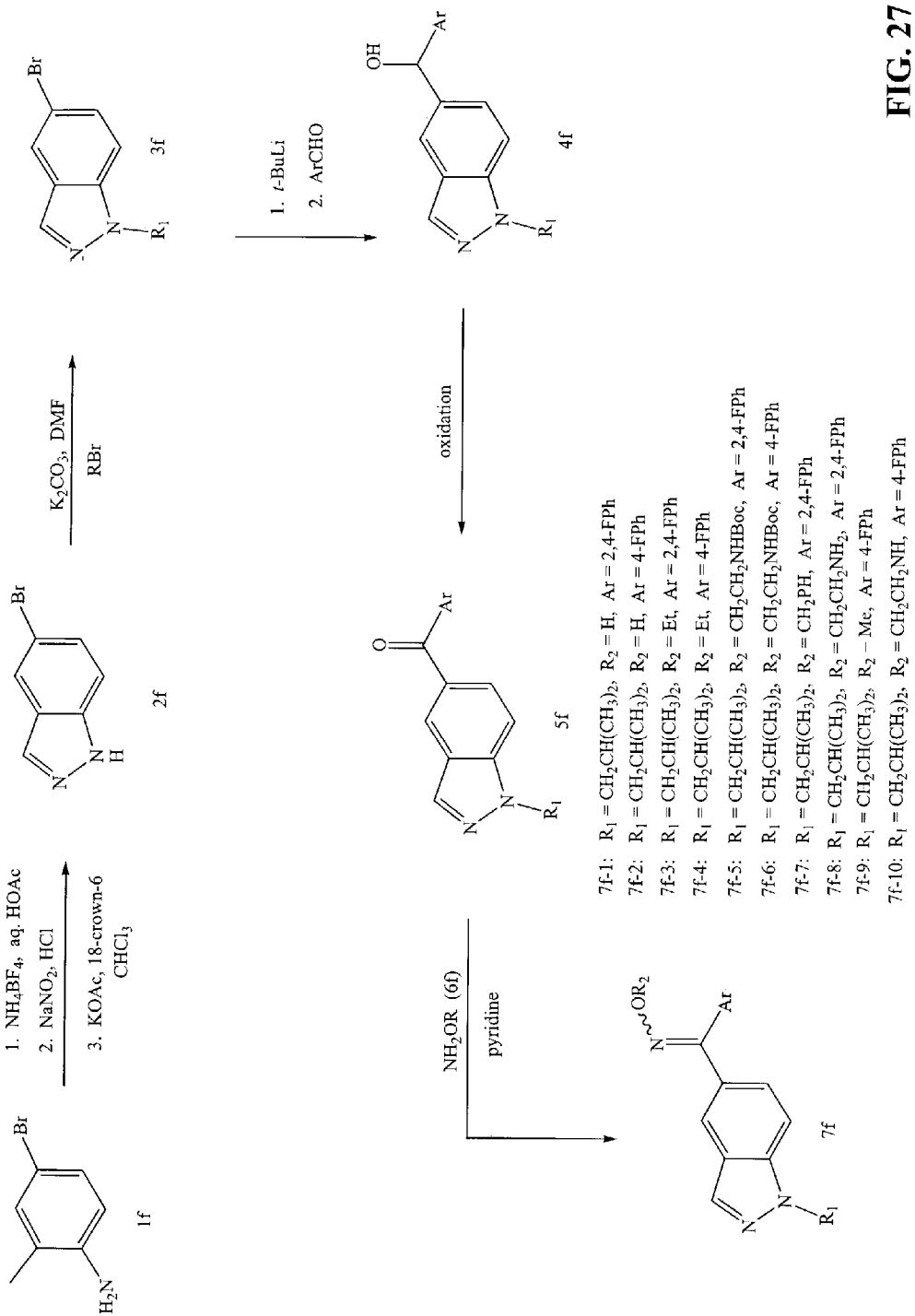
FIG. 27 shows a reaction scheme for the synthesis of compounds having the generic structure 7f.
Figure 28:
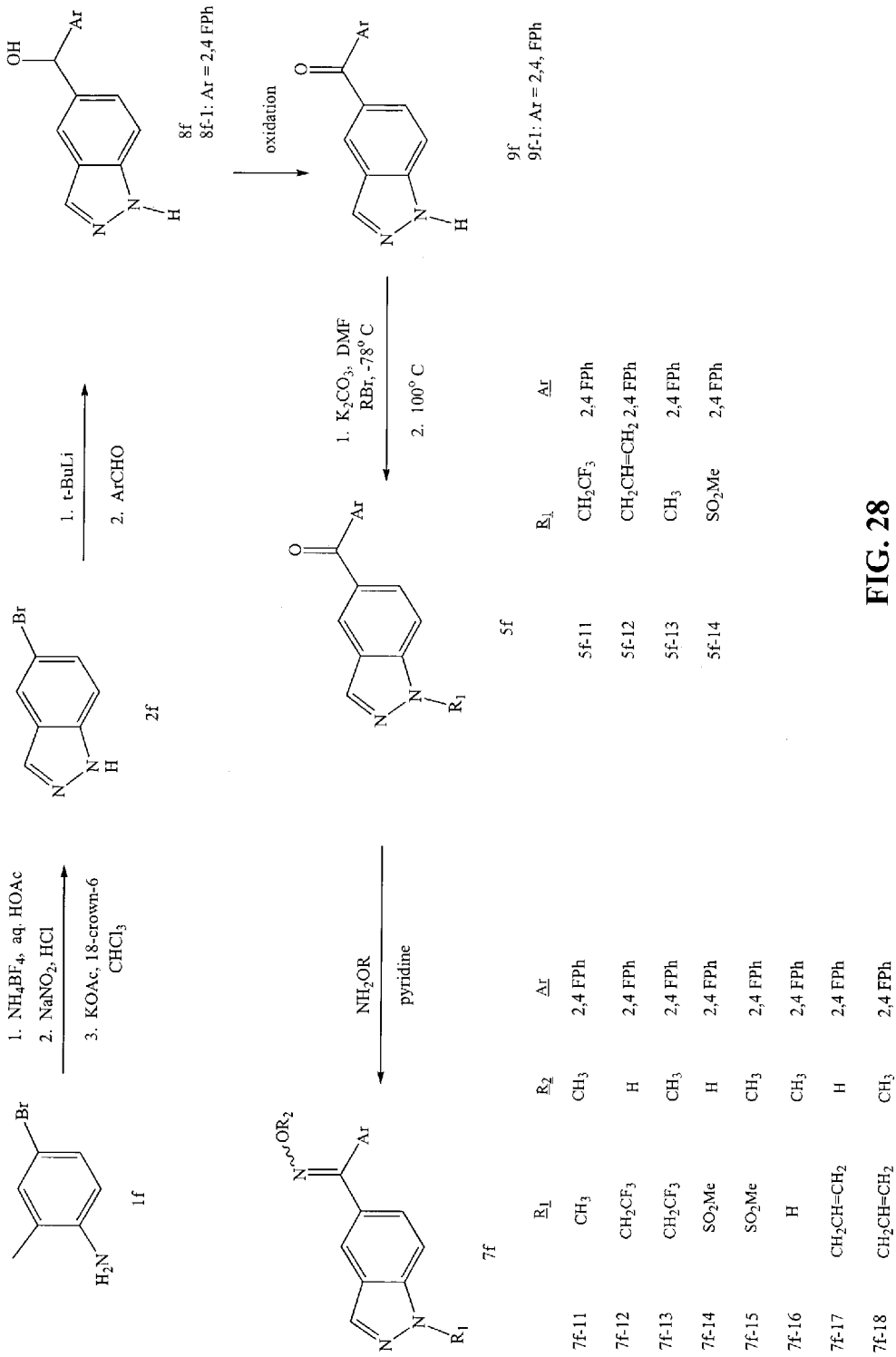
FIG. 28 shows an alternate reaction scheme for the synthesis of compounds having the generic structure 7f.
Figure 29:
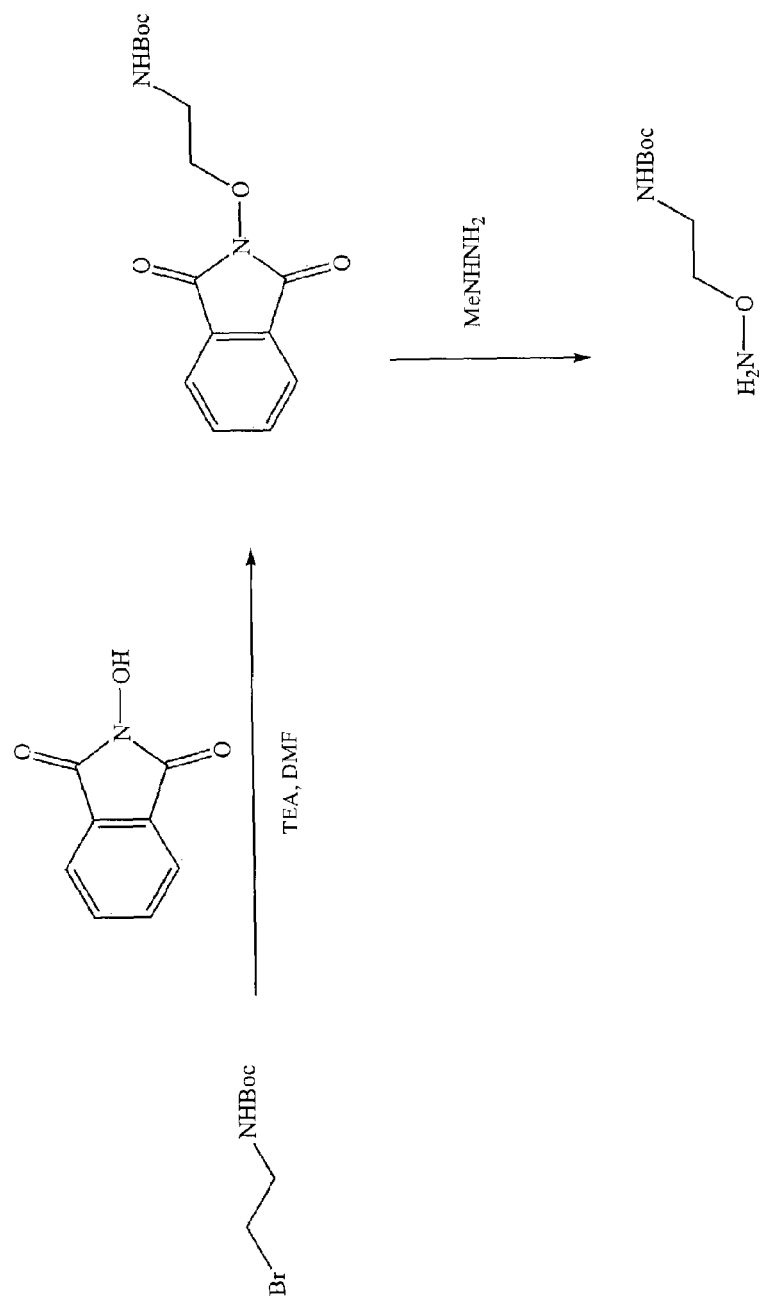
FIG. 29 shows a reaction scheme for the synthesis of an intermediate carboxamide acid used in the synthesis of compound 7f-5 and 7f-6.

FIG. 27 shows and example of the synthesis of a specific compound having the general Formula XII. In one general synthetic process, compounds of Formula XII are prepared as follows. 4-Bromo-2-methyl aniline is added to a mixture of ammonium tetrafluoroborate and acetic acid. After a period of time, sodium nitrite is added to the mixture, followed by the addition of a base such as potassium acetate and a phase-transfer catalyst such as 18-crown-6 to provide 5-bromoindazole. The bromoindazole is treated with RBr in the presence of a base to provide a 1-N-substituted 5-bromoindazole derivative, where R is alkyl, allyl, $ArCH_2$ or heteroaryl-$CH_2$ as defined above. Treatment of the 1-N-substituted derivative with Ar1CHO in the presence of a strong base such as butyl lithium, where Ar1 is as defined above, followed by treatment with a suitable oxidizing agent to provide the 1-N-substituted 5-C=OR derivative. Addition of $NH_2OR^1$ to this derivative in pyridine, where R6 is as defined above, provides an oxime compound of Formula XII. An alternative method for synthesizing compounds of Formula XII is shown in FIG. 28.

In another embodiment, this invention relates to compounds of the general Formula XIII:

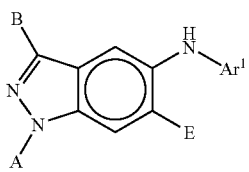

XIII where A, B, E and $Ar^1$ are defined as above.

Figure 34:
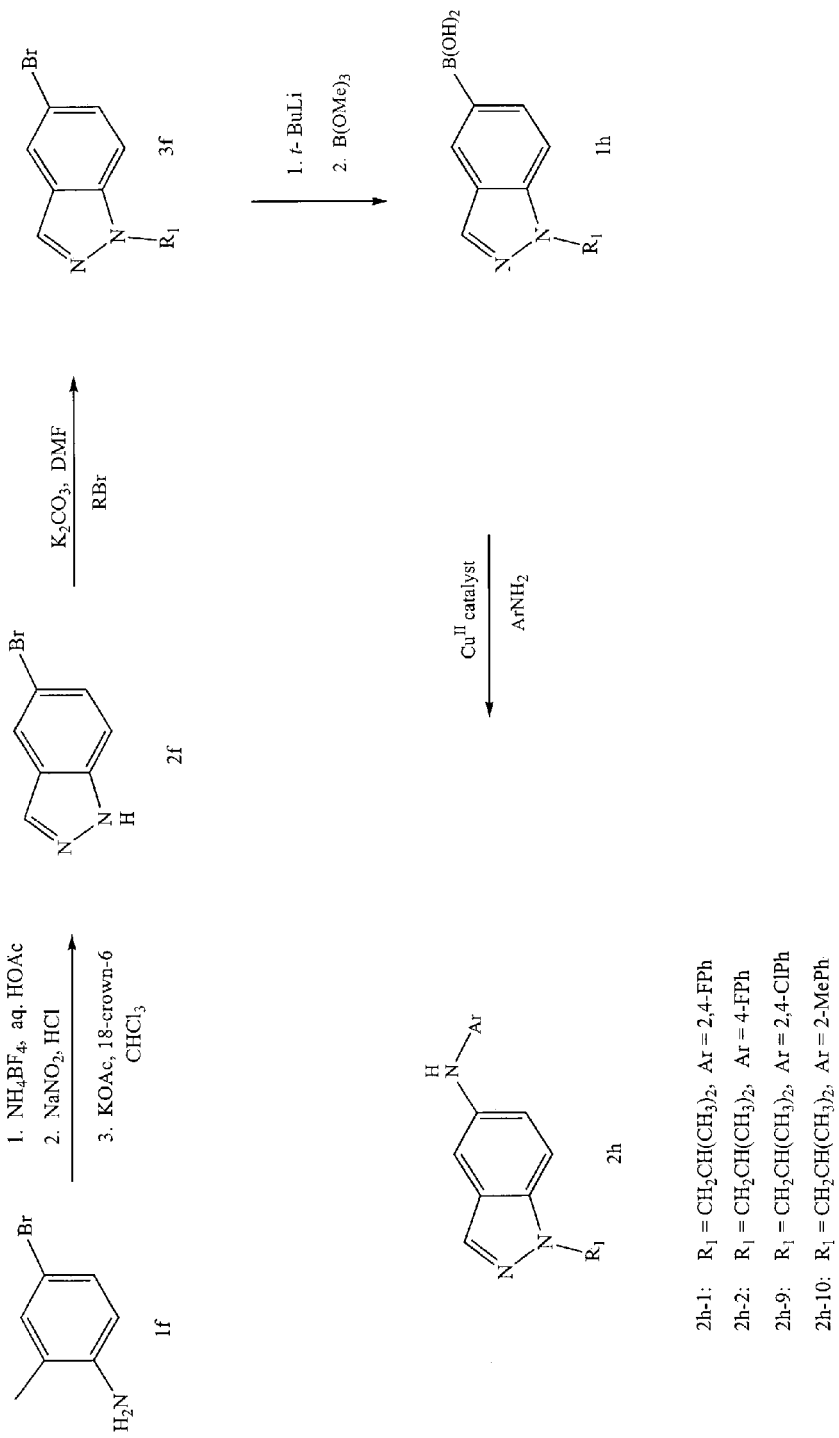
FIG. 34 shows a reaction scheme for the synthesis of compounds having the generic structure 2h.
Figure 35:
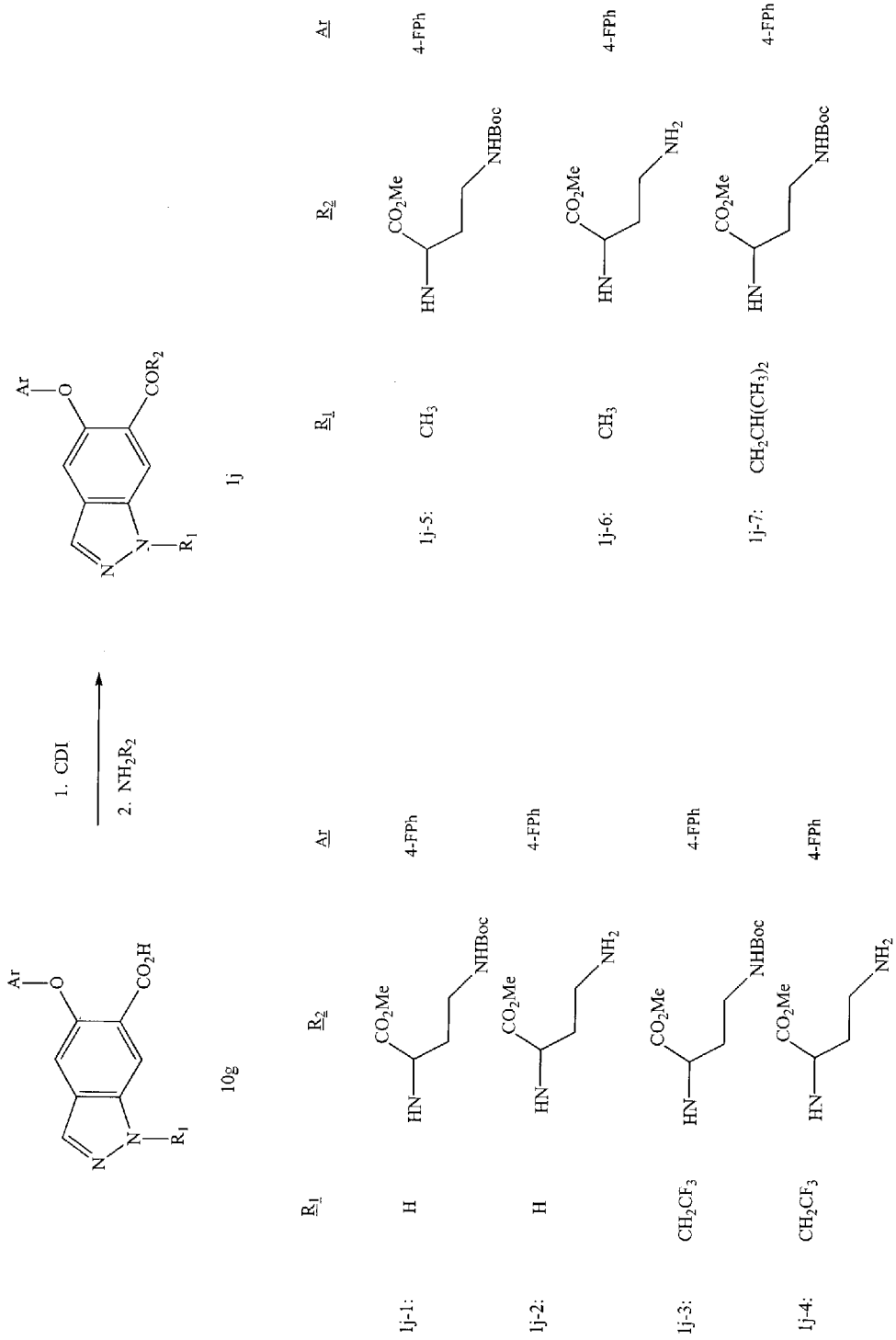
FIG. 35 shows a reaction scheme for the synthesis of compounds having the generic structure 1j.
Figure 36:
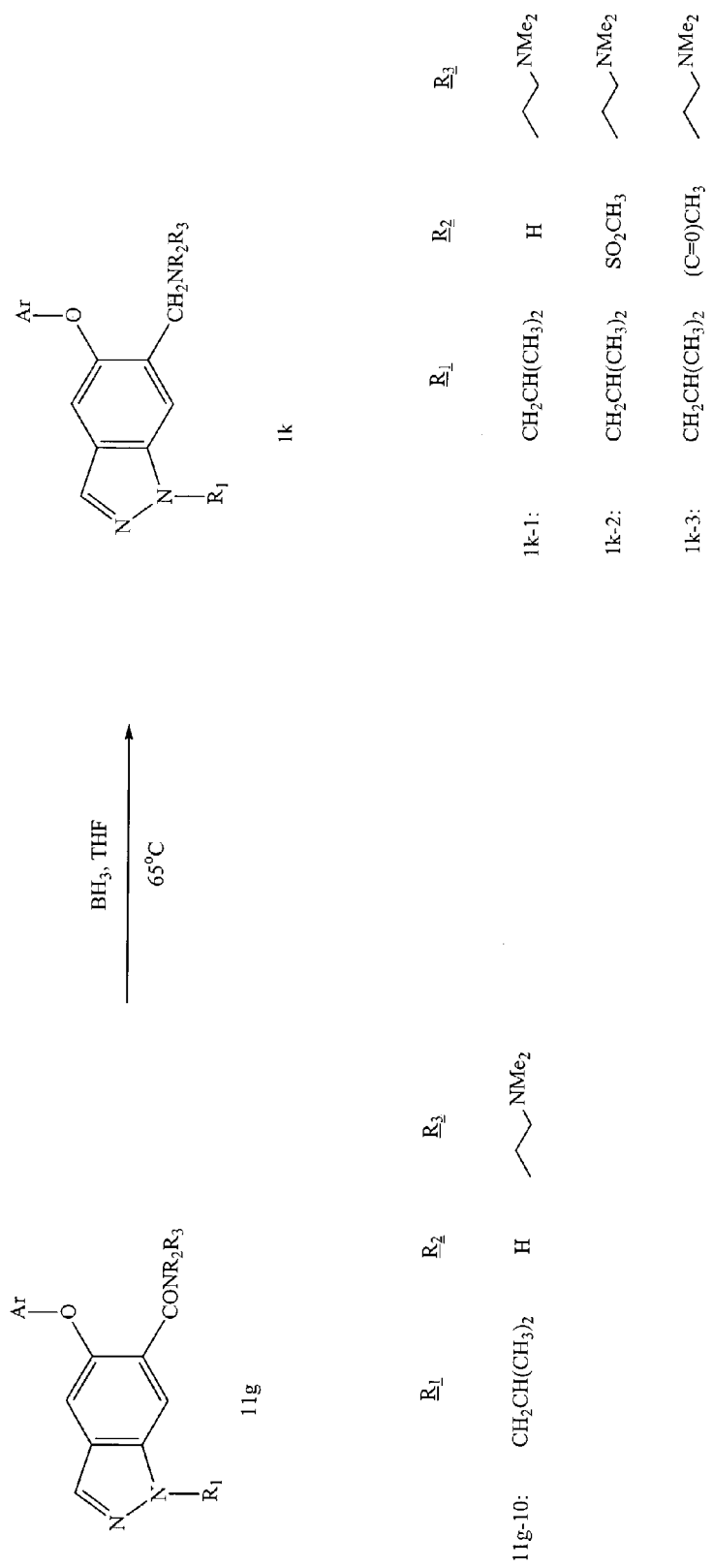
FIG. 36 shows a reaction scheme for the synthesis of compounds having the generic structure 1k.

FIG. 34 shows an example of the synthesis of a specific compound having the general Formula XIII. In one general synthetic process, compounds of Formula XIII are prepared as follows. 4-Bromo-2-methyl aniline is added to a mixture of ammonium tetrafluoroborate and acetic acid. After a period of time, sodium nitrite is added to the mixture, followed by the addition of a base such as potassium acetate and a phase-transfer catalyst such as 18-crown-6 to provide 5-bromoindazole. The bromoindazole is treated with RBr in the presence of a base to provide a 1-N-substituted 5-bromoindazole intermediate, where R is "A" as defined above for Formula XIII as defined above with the exception of hydrogen. Treatment of the 1-N-substituted intermediate with a strong base such as t-butyl lithium, followed by the addition of trimethylborate provides the 5-boronic acid indazole intermediate. Addition of a copper (II) catalyst, followed by the addition of a substituted or unsubstituted aniline provides a compound of the Formula XIII.

In another embodiment, this invention relates to compounds of the general Formula XIV:

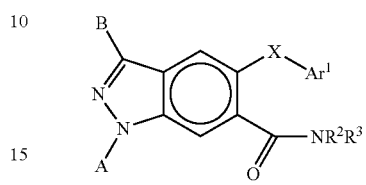

XIV where A, B, X, $Ar^1$, $R^2$ and $R^3$ are defined as above.

Figure 30A:
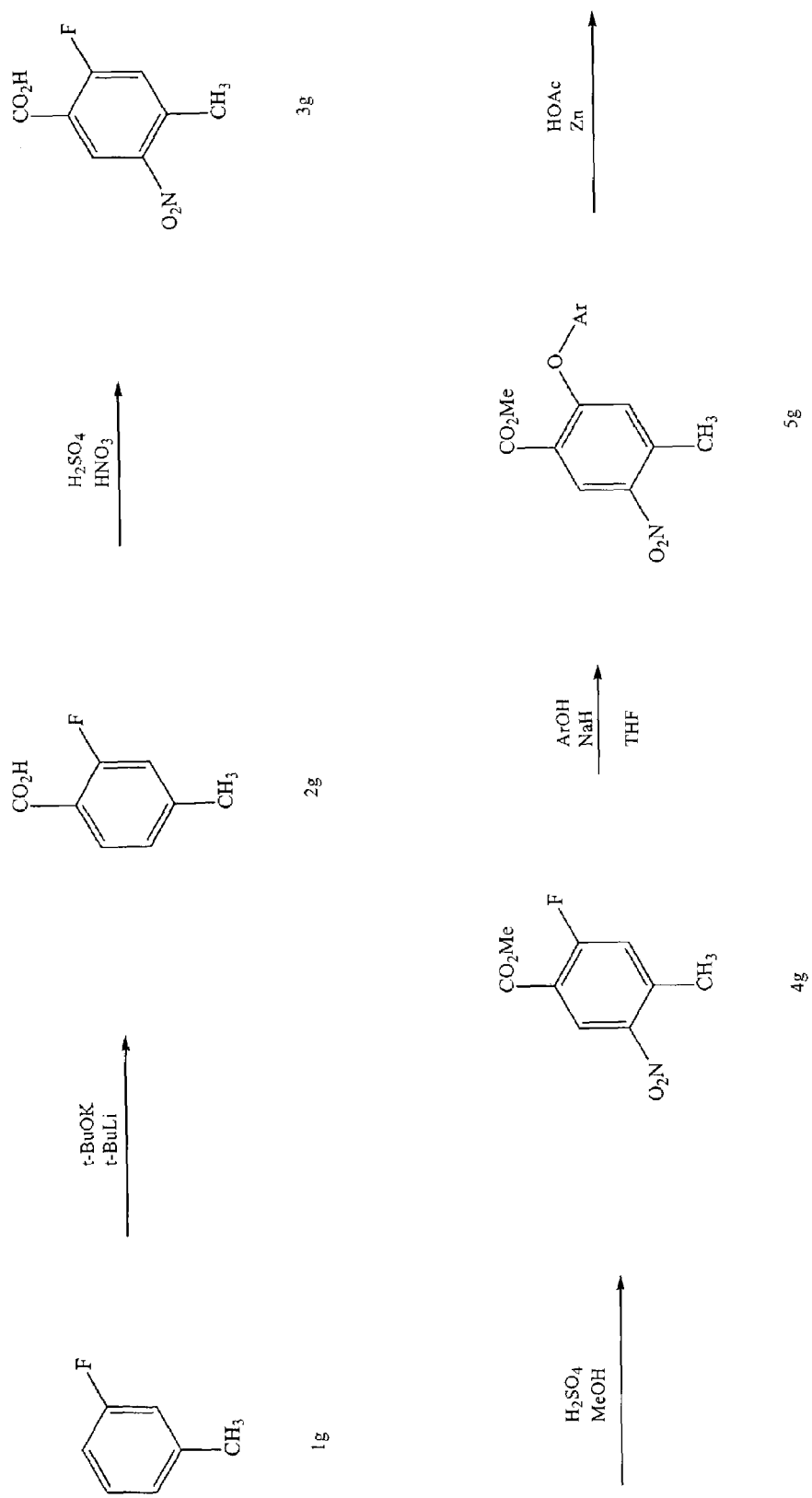
FIGS. 30A–30C show a reaction scheme for the synthesis of compounds having the generic structure 1g.
Figure 30B:
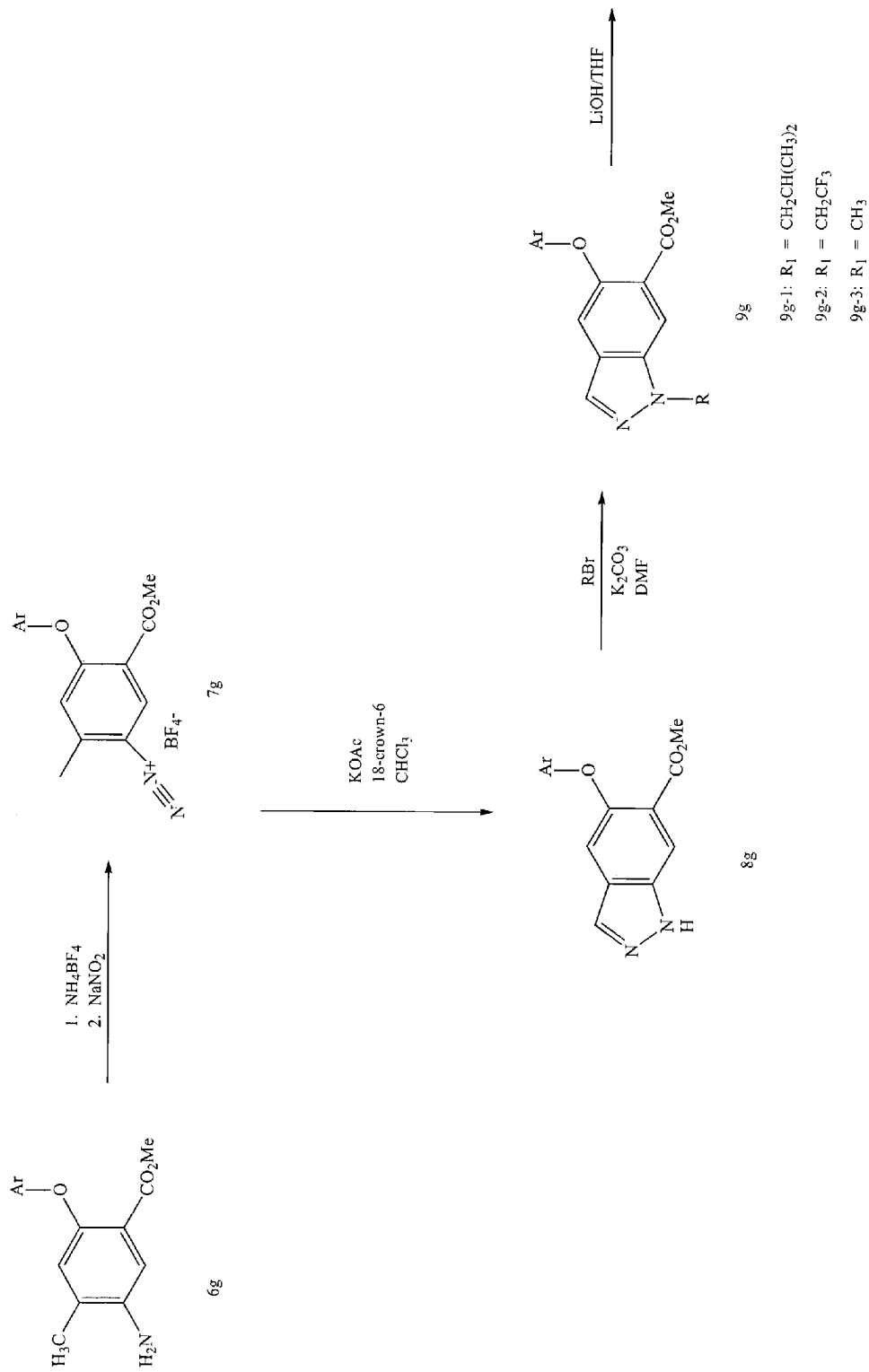
Figure 30C:
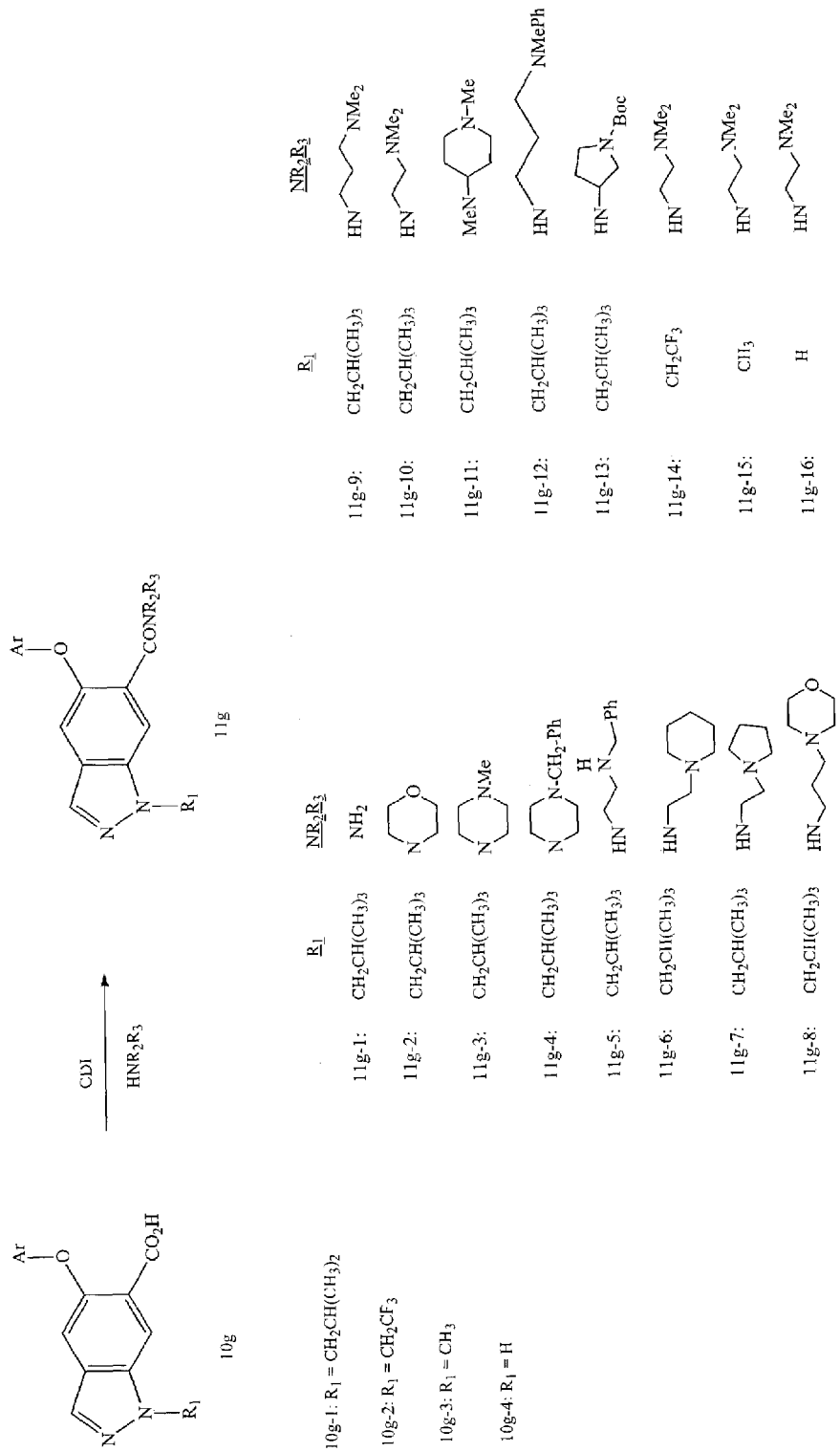

FIGS. 30A–30C show an example of the synthesis of a specific compound having the general Formula XIV. In one general synthetic process, compounds of Formula XIV are prepared as follows. 1-Fluoro-3-methyl-benzene undergoes an addition reaction to form 2-fluoro-4-methylbenzoic acid, followed by nitration to provide 2-fluoro-4-methyl-5-nitrobenzoic acid. The acid group is esterified, and then the fluoro group is replaced by ArO— upon treatment with ArOH and a strong base. Reduction of the nitro group followed by diazotization and cyclization provides the 5-OAr-6-$CO_2$Me indazole derivative, which is then treated with RBr in the presence of base to provide the 1-N substituted derivative. Hydrolysis of the ester group followed by amidation provides the 6-amide indazole derivative having Formula XIV.

In another embodiment, this invention relates to compounds of the general Formula XV:

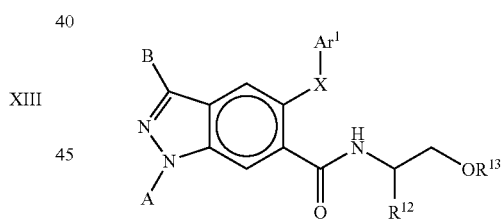

XV where A, B, X, and $Ar^1$ are defined as above, and $R^{12}$ and $R^{13}$ are independently alkyl, allyl, alkenyl, alkynyl, cycloalkyl, heterocycloalkyl, aryl, or heteroaryl, wherein said alkyl, allyl, alkenyl, alkynyl, cycloalkyl, heterocycloalkyl, aryl, or heteroaryl may be substituted or unsubstituted.

FIG. 34 shows an example of the synthesis of a specific compound having the general Formula XV. In one general synthetic process, compounds of Formula XV are prepared as follows. A 5-OAr-6-$CO_2$Me indazole derivative is prepared as described above with respect to the synthesis of Formula XIV, and then treated with RBr in the presence of base to provide the 1-N substituted derivative. Hydrolysis of the ester group followed treatment with carbonyldiimidazole and an amino acid provides the 6-substituted indazole derivative having Formula XV.

In another embodiment, this invention relates to compounds of the general Formula XVI:

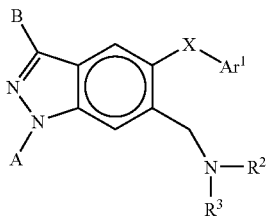

XVI where A, B, X, $R^2$, $R^3$, and $Ar^1$ are defined as above.

In one general synthetic process, compounds of Formula XVI are prepared as follows. A 5-OAr-6-CO$_2$Me indazole derivative is prepared as described above with respect to the synthesis of Formula XIV, and then reduced, for example, by treating with BH$_3$ in THF. Purification provides a compound of Formula XVI.

Therapeutically effective amounts of the compounds of the invention may be used to treat diseases mediated by modulation or regulation of protein kinases. An "effective amount" is intended to mean that amount of compound that, when administered to a mammal in need of such treatment, is sufficient to effect treatment for a disease mediated by the activity of one or more protein kinases, such as that p38 alpha and the associated p38 mediated events such as cytokine production. Thus, for example, a therapeutically effective amount of a compound selected from Formulas I–XVI or a salt, active metabolite or prodrug thereof, is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as p38, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I–XVI, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I–XVI, or a pharmaceutically acceptable salt or in vivo cleavable prodrug thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans will may contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I–XVI will naturally vary according to the nature and severity of the conditions, the age and sex of the animal or patient and the route of administration, according to well known principles of medicine.

In one aspect of this invention, the compounds of this invention or pharmaceutical salts or prodrugs thereof may be formulated into pharmaceutical compositions for administration to animals or humans to treat or prevent a p38-mediated condition. The term "p38-mediated condition" as used herein means any disease or other deleterious condition in which p38 is known to play a role. This includes conditions which are known to be caused by IL-1, TNF, IL-6 or IL-8 overproduction. Such conditions include, without limitation, inflammatory diseases, autoimmune diseases, destructive bone disorders, proliferative disorders, infectious diseases, viral disease, and neurodegenerative diseases Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Degenerative conditions or diseases which may be treated or prevented by the compounds of this invention include, but are not limited to, Alzheimer's disease, Parkinson's disease, cerebral ischemia and other neurodegenerative diseases.

"p38-mediated conditions" also include ischemia/reperfusion in stroke, heart attacks, myocardial ischemia, organ hypoxia, vascular hyperplasia, cardiac hypertrophy and thrombin-induced platelet aggregation.

In addition, the p38 inhibitors of this invention are also capable of inhibiting the expression of inducible pro-inflammatory proteins such as prostaglandin endoperoxide synthase-2 (PGHS-2), also referred to as cyclooxygenase-2

(COX-2). Therefore, other "p38-mediated conditions" are edema, analgesia, fever and pain, such as neuromuscular pain, headache, cancer pain, dental pain and arthritis pain.

The conditions and diseases that may be treated or prevented by the p38 inhibitors of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscel degeneration, cachexia, psoriatic arthritis, Reiter's syndrome, gout, traumatic arthritis, rubella arthritis, acute synovitis, diabetes, pancreatic .beta.-cell disease and Alzheimer's disease.

A TNF-mediated disease or condition includes rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated disease or condition includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

The compounds of this invention may be used in combination with other drugs and therapies used in the treatment of disease states which would benefit from the inhibition of cytokines, in particular IL-1, TNF, IL-6 or IL-8.

For example, by virtue of their ability to inhibit cytokines, the compounds of Formula I–XVI are of value in the treatment of certain inflammatory and non-inflammatory diseases which are currently treated with a cyclooxygenase-inhibitory non-steroidal anti-inflammatory drug (NSAID) such as indomethacin ketorolac, acetylsalicylic acid, ibuprofen, sulindac, tolmetin and piroxicam. Co-administration of a compound of the Formula I–XVI with a NSAID can result in a reduction of the quantity of the latter agent needed to produce a therapeutic effect, and thus the likelihood of adverse side-effects from the NSAID such as gastrointestinal effects are reduced. Thus according to a further feature of the invention there is provided a pharmaceutical composition which comprises a compound of Formula I–XVI, or a pharmaceutically-acceptable salt or in vivo cleavable ester thereof, in conjunction or admixture with a cyclooxygenase inhibitory non-steroidal anti-inflammatory agent, and a pharmaceutically-acceptable diluent or carrier.

The compounds of Formula I–XVI may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of Formula I–XVI may also be used in the treatment of asthma in combination with antiasthmatic agents such as bronchodilators and leukotriene antagonists.

Although the compounds of Formula I–XVI are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The activity of the compounds of this invention may be assayed for p38 inhibition in vitro, in vivo, or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands. These and other useful in vitro and cell culture assays are well known to those of skill in the art.

Cell culture assays of the inhibitory effect of the compounds of this invention may be used to determine the amounts of TNF-α, IL-1, IL-6 or IL-8 produced in whole blood or cell fractions thereof in cells treated with inhibitor as compared to cells treated with negative controls. Level of these cytokines may be determined through the use of commercially available ELISAs or as described in the Biological Examples section below.

BIOLOGICAL EXAMPLES

The biological activities of the compounds of the invention were demonstrated by the following in vitro assays.

p38 Biochemical Assay

P38 activity was assayed at room temperature in a 100 µl reaction containing 5 nM activated p38α enzyme and 1 uM ATF-2 (Activating Transcription Factor 2 fusion protein) as the substrate in 25 mM HEPES (pH 7.4), 100 µM Vanadate, 1 mM DTT, 10 mM $MgCl_2$ and 10 µM [γ-$^{33}$P]-ATP (~0.1 µCi $P^{33}$/reaction). The reaction was terminated after 30–40 minutes by adding 25% TCA, let stand for 5 minutes and then transferred directly to a GF-B membrane filter plate. The filter was washed twice for 30 seconds with 0.5% phosphoric acid using a Tomtec Mach III Automated Harvestor. After washing, the vacuum was continued for 30 seconds to dry the filter. Approximately 30 µl of scintillant was added per well to the filter plate and then read in a Liquid Scintillation Counter (Packard TopCount HTS).

PBMC Assay

The ability of compounds of this invention to inhibit TNF-α production was assessed by using human peripheral blood mononuclear cells ("PBMC") which synthesize and secrete TNF-α when stimulated with lipopolysaccharide.

Compound test solutions were made by making 5 fold serial dilutions in DMSO, which dilutions were then diluted to 5× stocks by diluting with MEM, 2% heat inactivated fetal bovine serum ("FBS"), 20 mM HEPES, 2 mM L-glutamine, and 1% penicillin/streptomycin.

PBMC's were isolated from human blood as follows. Whole blood samples were collected from human volunteers into Vacutainer™ CPT from Becton Dickinson. Tubes were mixed and centrifuged at room temperature (18–25° C.) in a horizontal rotor for a minimum of 15 minutes at 1500–1800 RCF (relative centrifugal force). For each donor, the buffy coat layers were pooled into a single tube and washed twice with phosphate buffered saline ("PBS"). The cell pellet was resuspended in MEM, 2% heat inactivated fetal bovine serum ("FBS"), 20 mM HEPES, 2 mM L-glutamine, and 1% penicillin/streptomycin. Total cell number was determined using a hemocytometer and the cell suspension was adjusted to 2×106 cells/mL.

0.1 mL of cell suspension was added to each well of a 96-well cell culture plate. 30 μL of a compound test solution was added, and the cells were incubated in a 37° C./5% CO2 incubator for 1 hour. 20 μL of 7.5 ng/mL lipopolysaccharide (LPS $E.$ $Coli$ K-235) was then added to each well, and the cells were returned to the 37° C./5% $CO_2$ incubator for 16–20 hours. The cells were centrifuged for 15 minutes at 1100 RCF. Approximately 0.12 mL of the supernatant was transferred into a clean 96 well polypropylene plate. The samples were either assayed immediately or were stored at −80° C. until ready for assay. TNF-α levels were determined in each sample using a human TNF-α ELISA assay such as that described below.

TNF-α levels were determined using the following assay. TNF-alpha antibody coated plates were prepared by adding 150 ul of 2 μg/mL anti-TNF-α purified mouse monoclonal IgG in Carbonate-Bicarbonate buffer (BupH™ Carbonate-Bicarbonate Buffer Pack) to wells of a 96-well Immulon 4 plate (Immulon 4 ELISA Flat Bottom Plate; Dynex, catalog number 011-010-3855) and incubated overnight at 2–8° C. Coating solution was removed and 200 ul of "blocking buffer" (20 mM HEPES pH 7.4, 150 mM NaCl, 2% BSA) was added and plates were stored 2–8° C. until ready to use. A ten-point recombinant human TNF-α standard curve was prepared by a 1:2 serial dilution in "sample diluent" (20 mM HEPES, pH 7.4, 150 mM NaCl, 2 mM $MgCl_2$, 1% BSA) with a top concentration of 6000 pg/mL.

Blocking solution was removed from TNF-α ELISA plates by washing five times with 300 μL of "wash buffer" (20 mM HEPES, pH 7.4, 150 mM NaCl, 2 mM MgCl2, 0.02% Tween-20). 50 μL of "sample diluent" was added to all wells, and then either 50 μL of a TNF-α standard curve solution or test compound supernatant was added to all wells. The plate was incubated at room temperature for one hour with shaking (300 rpm). The plate was washed wash five times with 300 μL "wash buffer". 100 μL of 0.2 μg/mL biotinylated goat anti-human TNF-α in "antibody diluent" (20 mM HEPES, pH 7.4, 150 mM NaCl, 2 mM $MgCl_2$, 1% BSA, 0.02% Tween-20) was added per well, and the plate was incubated at room temperature for one hour with shaking (300 rpm). The plate was washed wash five times with 300 μL "wash buffer" per well. 100 μL of 0.02 μg/mL streptavidin alkaline phosphatase in "antibody diluent" was added per well, and the plate was incubated at room temperature for one hour with shaking (300 rpm). The plate was washed wash five times with 300 μL wash buffer per well. 200 μl of 1 mg/ml pNPP (p-nitrophenyl phosphate) in diethanolamine buffer with 0.5 mM $MgCl_2$ was added per well, and the plate was incubated for 30 to 45 minutes at room temperature with shaking (300 rpm). Reaction progress was monitored by determining optical density: when the top standard reached an OD between 2.0 and 3.0, 50 μL of 2N NaOH was added per well. The optical density of each well was determined within 30 minutes, using a microtiter plate reader set to 405 nm. The data was analyzed in XL fit using 4-parameter curve fitting.

The following reagents were used in the above-described assays. Dulbecco's Phosphate Buffered Saline without Calcium or Magnesium (Gibco Catalog Number 14190); Minimum essential medium Eagle (MEM; Gibco Catalog Number 11090); penicillin-streptomycin (Gibco Catalog Number 15140); L-glutamine, 200 mM (Gibco Catalog Number 25030); HEPES, 1M (Gibco Catalog Number 15630); fetal bovine serum ("FBS"; HyClone Catalog Number SH30070.03); lipopolysaccharides from $Escherichia$ $coli$ K-235 ("LPS"; Sigma Catalog Number L2018); anti-TNF-α, Purified Mouse Monoclonal IgG (R&D Systems Catalog Number MAB210); BupH™ Carbonate-Bicarbonate Buffer Pack (Pierce Catalog Number 28382); HEPES (FW 238.3; Sigma Catalog Number H3575); NaCl (Sigma Catalog Number S7653); bovine serum albumin ("BSA"; Jackson ImmunoReseach Catalog Number 001-000-162); polyoxyethylene 20 sorbitan monolaurate (Sigma Catalog Number P2287); magnesium chloride, hexahydrate (Sigma Catalog Number M2670); recombinant human TNF-α (R&D Systems Catalog Number 210TA010); biotinylated TNF-α affinity purified goat IgG (R&D Systems Catalog Number BAF210); streptavidin alkaline phosphatase (Jackson ImmunoResearch Catalog Number 016-050-084); diethanolamine Substrate Buffer (Pierce Catalog Number 34064); p-nitrophenyl phosphate (Sigma Catalog Number N2765).

Table 3 shows the results of p38 inhibition and inhibition of LPS-induced TNF-α secretion from human peripheral blood mononuclear cells ("PBMC"). An "active" compound is defined as a compound having an $IC_{50}$ below 500 nM.

TABLE 3

| Compound | p38 Inhibition $IC_{50}$ (nM) | PBMC $IC_{50}$ (nM) |
| --- | --- | --- |
| 7f-1 | active | active |
| 7f-2 | active | active |
| 7f-3 | active | active |
| 7f-4 | active | not tested |
| 7f-7 | active | not tested |
| 7f-9 | active | not tested |
| 7f-12 | active | not tested |
| 7f-13 | active | not tested |
| 7f-14 | active | not tested |
| 7f-15 | active | not tested |
| 7f-17 | active | not tested |
| 11g-1 | active | not tested |
| 11g-10 | active | active |
| 11g-14 | active | not tested |
| 4f-1 | active | active |
| 4f-2 | active | active |
| 4f-7 | active | not tested |
| 4f-8 | active | not tested |
| 4f-9 | active | inactive |
| 4f-10 | active | not tested |
| 5f-1 | active | active |
| 5f-2 | active | active |
| 5f-7 | active | active |
| 5f-8 | active | not tested |
| 5f-9 | active | active |
| 5f-10 | active | active |
| 5f-11 | active | not tested |
| 5f-12 | active | not tested |
| 2h-1 | active | active |
| 2h-2 | active | active |
| 2h-10 | active | active |

TABLE 3-continued

| Compound | p38 Inhibition IC$_{50}$ (nM) | PBMC IC$_{50}$ (nM) |
|---|---|---|
| 1j-2 | active | not tested |
| 1j-4 | active | not tested |
| 2h-1 | active | active |

Mouse Assay

Mouse Model of LPS-Induced TNF-α Production

TNF-α was induced in male DBA-2J mice (from Jackson Laboratories) by tail vein injection with 2 mg/kg lipopolysaccharide (from Sigma, St. Louis). Ninety minutes later isoflurane anaesthetized mice were bled by cardiac puncture. The blood samples were then allowed to clot for two hours at 4° C. and centrifuged. Serum was separated into eppendorf tubes for later TNF-α analysis. TNF-α analysis was performed using an ELISA kit (Quantikine, MN) and was performed according to the instructions that accompanied the kit.

Compound AR-00112190 was prepared with 10% DMSO plus 90% of 20% 2-hydroxyl-β-Cyclodextrin (HPCD). Compound AR-00112190 is a derivative of compound 14g (see FIG. 3) where A is isobutyl. The compound was then serially diluted with vehicle (10% DMSO, 90% 20% HPCD) to prepare concentrations required for the lower dose levels.

The compound went into solution with the addition of DMSO, but then came out of solution on addition of 20% HPCD. Therefore, compounds were dosed as suspensions. Seven groups of male DBA-2J mice (seven/group) were dosed orally with AR-00112190 (10, 30 and 100 mg/kg) 30 minutes prior to LPS injection.

Treatment with compound AR-00112190 (10, 30 and 100 mg/kg) also significantly decreased TNF-α levels. AR-00112190 showed a mg/kg as evidenced by a similar inhibition (42%) seen with the 100 mg/kg dose (Table 4).

Results of this study demonstrated significant beneficial effects with 10, 30 and 100 mg/kg of AR-00112190 (29%, 44% and 42%).

TABLE 4

| Group | Treatment | Animal | TNF Level pg/ml | Mean | SE | % inhibition |
|---|---|---|---|---|---|---|
| I | LPS + Vehicle | 1 | 3290 | 3825 | 390 | 0 |
|   |   | 2 | 3545 |   |   |   |
|   |   | 3 | 3212 |   |   |   |
|   |   | 4 | 5604 |   |   |   |
|   |   | 5 | 4978 |   |   |   |
|   |   | 6 | 2947 |   |   |   |
|   |   | 7 | 3196 |   |   |   |
| II | LPS + AR-00112190 10 mg/kg | 1 | 3373 | 2706 | 206 | 29 |
|   |   | 2 | 2047 |   |   |   |
|   |   | 3 | 2782 |   |   |   |
|   |   | 4 | 2080 |   |   |   |
|   |   | 5 | 2365 |   |   |   |
|   |   | 6 | 3298 |   |   |   |
|   |   | 7 | 2967 |   |   |   |
| III | LPS + AR-00112190 30 mg/kg | 1 | 2815 | 2126 | 292 | 44 |
|   |   | 2 | 1826 |   |   |   |
|   |   | 3 |   |   |   |   |
|   |   | 4 | 1464 |   |   |   |
|   |   | 5 | 3135 |   |   |   |
|   |   | 6 | 1393 |   |   |   |
|   |   | 7 | 2124 |   |   |   |
| IV | LPS + AR-00112190 100 mg/kg | 1 | 2074 | 2216 | 224 | 42 |
|   |   | 2 | 1783 |   |   |   |
|   |   | 3 | 1832 |   |   |   |
|   |   | 4 | 2333 |   |   |   |
|   |   | 5 | 3257 |   |   |   |
|   |   | 6 | 1553 |   |   |   |
|   |   | 7 | 1683 |   |   |   |

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other p38 inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

EXAMPLES

In the examples described below, unless otherwise indicated all temperatures are set fourth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

1H-NMR spectra were recorded on a Bruker instrument operating at 300 MHz or on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Preparation of 5-(4-fluorophenylsulfanyl)-1-(4-methoxybenzyl)-1H-pyrazolo[3,4-c]pyridine (7a)

FIG. 1 shows a reaction scheme for the synthesis of compounds 7a having the general Formula II. In this example, the synthesis of compound 7a, where R is 4-methoxybenzyl and X is sulfur, is described.

Step A: 1.285 g of 2-chloro-4-methyl-5-nitropyridine (compound 1a) and 1.023 g of 4-fluorobenzenethiol were dissolved in 15 mL of anhydrous THF under dry nitrogen. To this solution was slowly added 207 mg of sodium hydride (95% in oil). The reaction mixture was then partitioned between EtOAc and 0.1 N aqueous NaOH (to remove any unreacted thiol) and then the organic layer was washed with brine, dried over $Na_2SO_4$, filtered and concentrated under vacuum. The resulting residue was purified on a Biotage column eluting with a gradient from 1:1 hexane/$CH_2Cl_2$ to 100% $CH_2Cl_2$ to give 1.90 g of compound 2a.

Step B: Approximately 1.90 g of compound 2a and 1.88 g of iron powder were added to 20 mL of acetic acid under an atmosphere of dry nitrogen. The reaction mixture was then heated to 90° C. for about 45 minutes to form intermediate product 3a. Approximately 1.90 g of the intermediate product 3a and 1.160 g of NaOH were dissolved in 20 mL of methanol under an atmosphere of dry nitrogen for about 3.5 hours, and then reaction mixture was cooled to ambient temperature and stirred at ambient temperature for 12 hours. The reaction mixture was concentrated under vacuum and then partitioned between $CH_2Cl_2$ and water. The $CH_2Cl_2$ layer was then washed with brine, dried over $Na_2SO_4$, filtered and concentrated under vacuum to provide compound 4a.

Step C: Without further purification, 1.54 g of compound 4a and 896 mg of ammonium tetrafluoroborate were taken up in 10 mL of a 1:1 solution of acetone and water. The reaction mixture was then placed in an ice bath (0° C.) to which was added 600 µL of concentrated HCl followed by 514 mg of sodium nitrite. The reaction mixture was then stirred for approximately 45 minutes after which time a precipitate of the intermediate compound 5a was formed. The precipitate was collected, air-dried, and then further dried by azeotroping from ethanol and toluene to provide approximately 800 mg of compound 5a. Without further purification, approximately 800 mg of compound 5a, 312 mg of potassium acetate and 190 mg of 18-crown-6 were dissolved/suspended in 5 mL of chloroform under an atmosphere of dry nitrogen. The reaction mixture was then partitioned between $CH_2Cl_2$ and water. The $CH_2Cl_2$ layer was washed with water and brine, dried over $Na_2SO_4$, filtered, and concentrated under vacuum. The resulting residue was purified on a Biotage column to give 388 mg of compound 6a.

Step D: 173.3 mg of compound 6a, 195 mg of potassium carbonate, 110 µL of 4-methoxybenzyl chloride and 10.5 mg of sodium iodide were dissolved/suspended in 1 mL of anhydrous DMF under an atmosphere of dry nitrogen. The reaction mixture was heated to 85° C. for approximately 1.5 hours, and then cooled to ambient temperature. The reaction mixture was partitioned between $CH_2Cl_2$ and water, and the $CH_2Cl_2$ layer was washed water and brine, dried over $Na_2SO_4$, filtered, and concentrated under vacuum. The resulting residue was purified on a Biotage column to give approximately 100 mg of compound 7a.

Example 2

Preparation of 1-allyl-5-(4-fluorophenoxy)-1H-pyrazolo[3,4-c]pyridine (14a)

Figure 2:
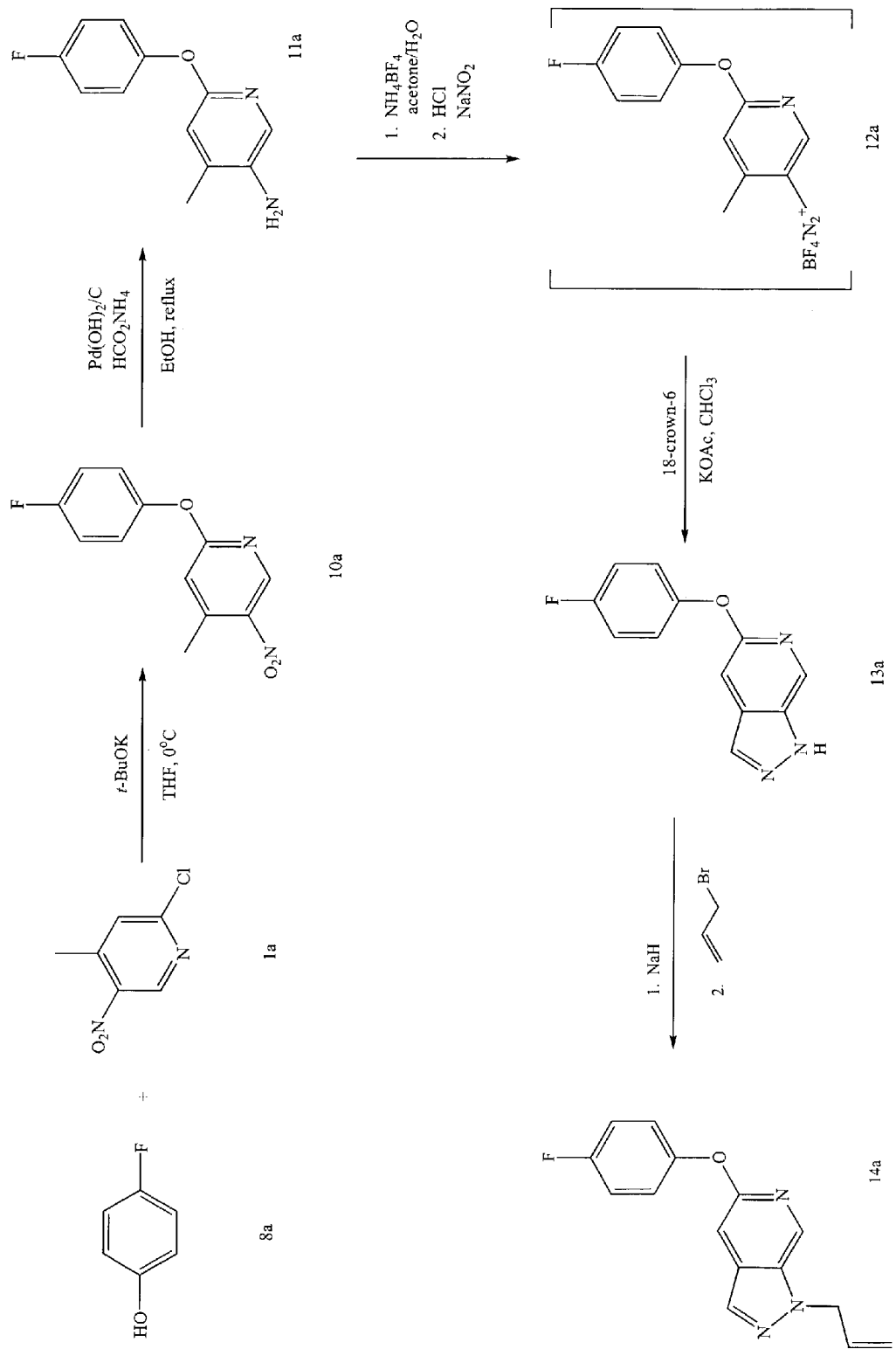

FIG. 2 shows a reaction scheme for the synthesis of compound 14a having the general Formula II.

Step A: In a round bottom flask, 4-fluorophenol (compound 8a; 1.3 mL, 2.0 mmols) was diluted with 25 mL of anhydrous THF and the reaction mixture was cooled in an ice bath as potassium t-butoxide (12.0 mL, 12.0 mmols) was slowly added. Next, 2-chloro-4-methyl-5-nitropyridine (compound 1a; 2.23 g, 12.5 mmols) was added and the reaction mixture was warmed to room temperature and stirred for 12 hours. The reaction mixture was concentrated, and the residue was diluted with $CH_2Cl_2$. The organic layer was washed with a 1N NaOH solution and brine, dried over $Na_2SO_4$, and filtered. The filtrate was concentrated to a dark residue which was purified on a Biotage 40 M silica column, eluting with 50:50 $CH_2Cl_2$/hexanes, to provide 2.84 g of compound 10a as a white solid.

Step B: In a round bottom flask, compound 10a (2.6 g, 11 mmols) was diluted with 40 mL EtOH, and then $Pd(OH)_2$ (230 mg, 2 mmols) was added followed by the addition of ammonium formate (3.3 g, 53 mmols). The reaction mixture was heated to 80° C. until the starting material 10a was gone as determined by HPLC. The reaction mixture was filtered through glass paper and the filtrate was concentrated. The residue was diluted with $CH_2Cl_2$ and the organic layer was washed with saturated $NaHCO_3$ and brine, dried over $Na_2SO_4$, filtered and concentrated to provide 1.92 g of compound 11a as a white solid.

Step C: Compound 11a was converted to compound 13a according to the method described in Step C of Example 1. Compound 11a and of ammonium tetrafluoroborate were taken up in a 1:1 solution of acetone and water. The reaction mixture was then placed in an ice bath (0° C.) to which was added concentrated HCl followed by sodium nitrite, and a precipitate was formed. The precipitate was collected, air-dried, and then further dried by azeotroping from ethanol and toluene to provide the intermediate compound 12a. Compound 12a, potassium acetate and 18-crown-6 were dissolved/suspended in chloroform under an atmosphere of dry nitrogen. The reaction mixture was then partitioned between $CH_2Cl_2$ and water. The $CH_2Cl_2$ layer was washed with water and brine, dried over $Na_2SO_4$, filtered, and concentrated under vacuum. The resulting residue was purified on a Biotage column to give compound 13a.

Step D: In a round-bottom flask, compound 13a was diluted with 4 mL of DMF, and then 22 mg of NaH was added and bubbling began. Upon settling, 0.8 mL of allyl bromide was added, and the mixture was stirred under nitrogen at room temperature. The reaction mixture was quenched with water and then concentrated. The residue was diluted with $CH_2Cl_2$ and the organic layer was washed with saturated sodium bicarbonate and brine, concentrated to a film, and dried. The resulting residue was purified on a Biotage column having a 12 M silica column, eluting with 4% EtOAc:$CH_2Cl_2$, to provide compound 14a.

Example 3

Preparation of 3[-5-(4-fluoro-phenyloxy)-pyrazolo[3,4-c]pyridin-1-yl]-propane-1,2-diol (15a)

Figure 3:
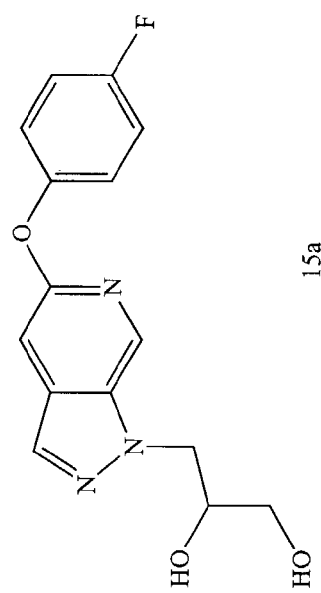
Figure 3:
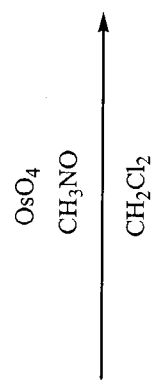
Figure 3:
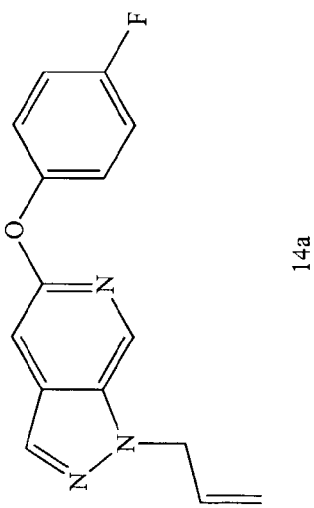

FIG. 3 shows the reaction scheme for the synthesis of compound 15a having the general Formula II. In a round-bottom flask, 79 mg (0.3 mmols) of compound 14a, prepared according to Example 2, was diluted with 2 mL of anhydrous $CH_2Cl_2$. Trimethylamine-N-oxide (27 mg, 0.35 mmol) was added under a nitrogen atmosphere. After all solids were dissolved, $OsO_4$ (11 mg, 0.04 mmols) was added and the reaction mixture was stirred at room temperature. The reaction mixture was then partitioned between $CH_2Cl_2$ and water. The organic layer was dried over $Na_2SO_4$, filtered, and then concentrated to a film. The film was purified on a Biotage 12 M silica column eluting with EtOAc to provide 82 mg of compound 15a.

Example 4

Preparation of [5-(4-fluorophenyloxy)-pyrazolo[3,4-c]pyridin-1-yl]-acetaldehyde (16a)

Figure 4:
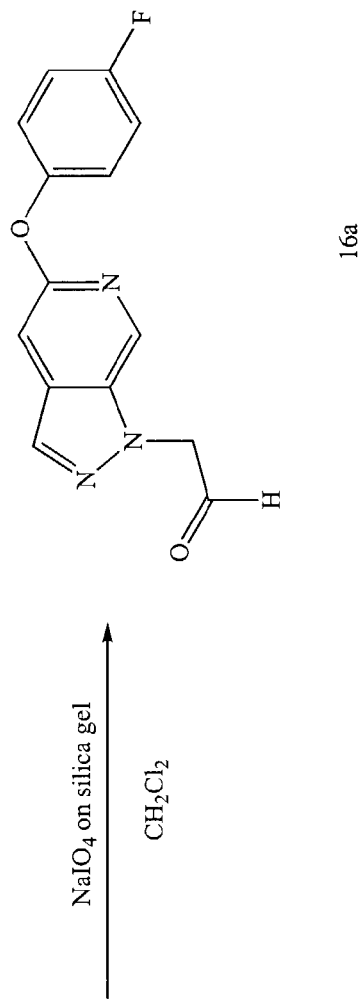
Figure 4:
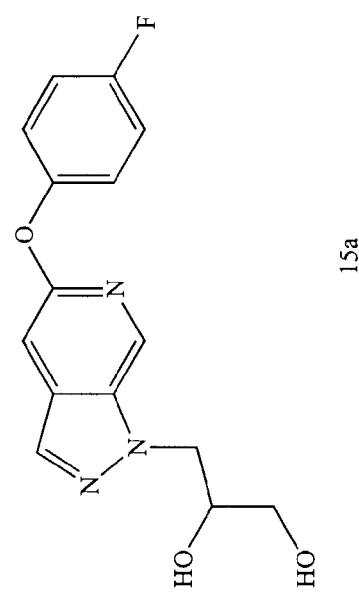

FIG. 4 shows a reaction scheme for the synthesis of compound 16a. A 0.3 M solution of $NaIO_4$ (2 mL) was combined with 1 g of silica gel to give slurry. The slurry was diluted with 3 mL of $CH_2Cl_2$ and 82 mg (0.3 mmols) of compound 15a, prepared according to Example 3, was added into the slurry with 1 mL of $CH_2Cl_2$, and the slurry was stirred for 2 hours. After 3 hours, the reaction mixture was filtered and the pad was washed with $CH_2Cl_2$. The filtrate was concentrated to provide 35 mg of compound 16a as a brown film.

Example 5

Preparation of 5-(4-fluorophenyloxy)-1-oxazol-5-ylmethyl-1H-pyrazolo[3,4-c]pyridine (17a)

Figure 5:
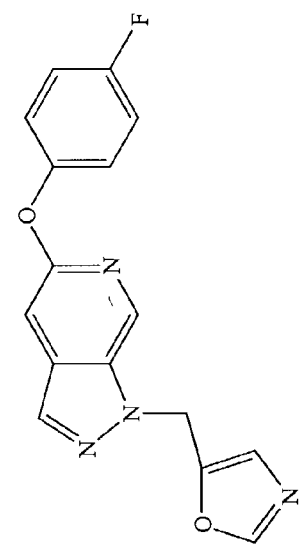
Figure 5:
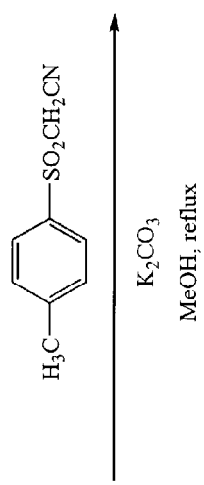
Figure 5:
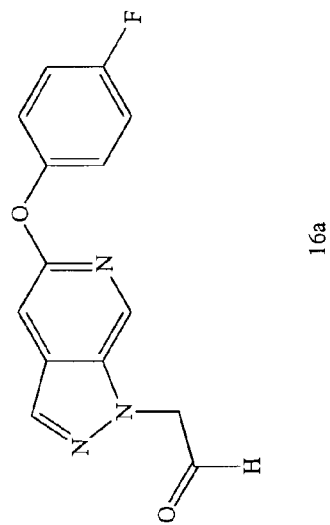

FIG. 5 shows the reaction scheme for the synthesis of compound 17a having the general Formula II. In a round bottom flask, compound 16a (32 mg, 0.11 mmols), prepared according to Example 4, was combined with MeOH (2 mL) and $K_2CO_3$ (32 mg, 0.2 mmols), and then tosylmethylisocyanide (25 mg, 0.13 mmols) was added and the reaction mixture was heated to reflux. The reaction mixture was then concentrated and the residue was diluted with $CH_2Cl_2$. The $CH_2Cl_2$ was washed with water and 1 N HCl, separated, and concentrated. The resulting residue was purified on a silica column, eluting with 80% EtOAc/$CH_2Cl_2$, to provide compound 17a.

Example 6

Preparation of 1-allyl-5-(4-fluoro-phenylsulfanyl)-1H-pyrazolo[3,4-c]pyridine (18a)

Figure 6:
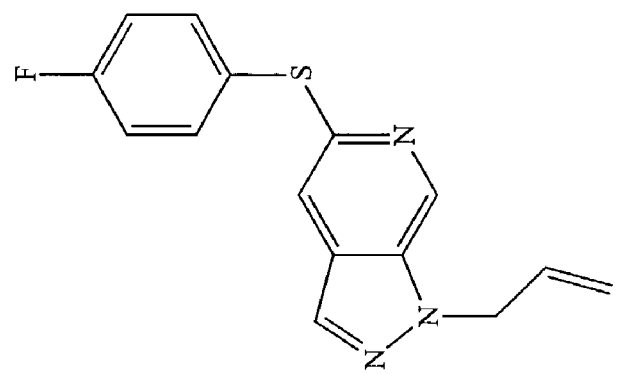
Figure 6:
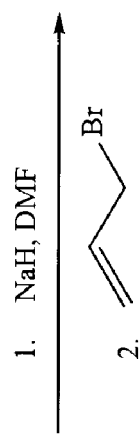
Figure 6:
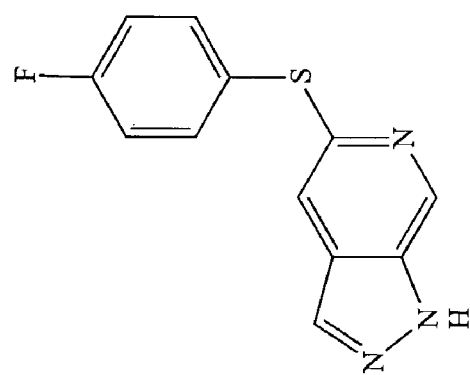

FIG. 6 shows the reaction scheme for the synthesis of compound 18a having the general Formula II. In a round bottom flask with an inlet for nitrogen, compound 6a, prepared according to Example 1, was diluted with 4 mL of DMF and then the 22 mg of NaH was added and bubbling began. Upon settling, allyl bromide (0.8 mL) was added and the reaction was stirred under nitrogen at room temperature. The reaction mixture was quenched with water and then concentrated. The residue was taken up in $CH_2Cl_2$ and washed with saturated sodium bicarbonate solution and brine, and then dried to an orange film. The film was purified on a Biotage column having a 12M silica column and eluting with 4% EtOAc/$CH_2Cl_2$ to provide compound 18a.

Example 7

Preparation of 1-N-substituted 4-azaindazoles (7b)

FIG. 7 shows a reaction scheme for the synthesis of compounds 7b having the general Formula III.

Step A: In a round bottom flask, 4-fluorobenzenethiol was diluted with anhydrous THF. The reaction mixture was cooled to 0° C. with an ice bath, and then 1.0 M potassium tert-butoxide in THF was slowly added to the reaction mixture. The reaction mixture was stirred at 0° C. for 10 minutes, and then 5-chloro-3-methyl-2-nitropyridine (compound 1b) was added and the reaction mixture was stirred at 0° C. for 10 minutes and then warmed to room temperature. The reaction mixture was concentrated and in the residue was diluted with $CH_2Cl_2$. The $CH_2Cl_2$ was washed with 1 N NaOH solution and brine, dried over $Na_2SO_4$, filtered, and the filtrate was concentrated to a yellow oil. The resulting residue was purified on a Biotage 40 M column eluting with 50:50 hexane/$CH_2Cl_2$ to provide compound 3b.

Step B: Compound 3b was reduced with iron powder and acetic acid as described Example 1, step B to provide compound 4b.

Step C: Compound 4b was then treated with ammonium tetrafluoroborate followed by concentrated HCl and sodium nitrite as described in Example 1, Step C to provide intermediate 5b. Without further purification, compound 5b was combined with potassium acetate and 18-crown-6 as described in Example 1, step C to provide compound 6b.

Step D: Compounds 7b-1, 7b-2, and 7b-3 were each prepared from compound 6b as shown in FIG. 7. To prepare compound 7b-1, compound 6b was treated with NaH and allyl bromide as described in Example 6.

Example 8

Preparation of 3-[5-(4-fluorophenylsulfanyl)-pyrazolo[4,3-b]pyridin-1-yl]-propylamine (8b)

FIG. 8 shows the reaction scheme for the synthesis of compound 8b having the general Formula III. In a round bottom flask, compound 7b-3, prepared according to Example 7, was diluted with $CH_2Cl_2$ and trifluoroacetic acid. The reaction mixture was stirred until the starting material was gone as determined by TLC, and then concentrated, and the resulting residue was diluted with $CH_2Cl_2$. The $CH_2Cl_2$ was washed with 1 N NaOH and brine, dried over $Na_2SO_4$, filtered, and concentrated. The resulting residue was purified on a Biotage 12M silica column, eluting with 10% MeOH/$CH_2Cl_2$/$NH_4OH$, to provide compound 8b.

Example 9

Preparation of 6-(4-fluorophenylsulfanyl)-3-(4-methoxybenzyl)-1H)indazole (10c)

Figure 9A:
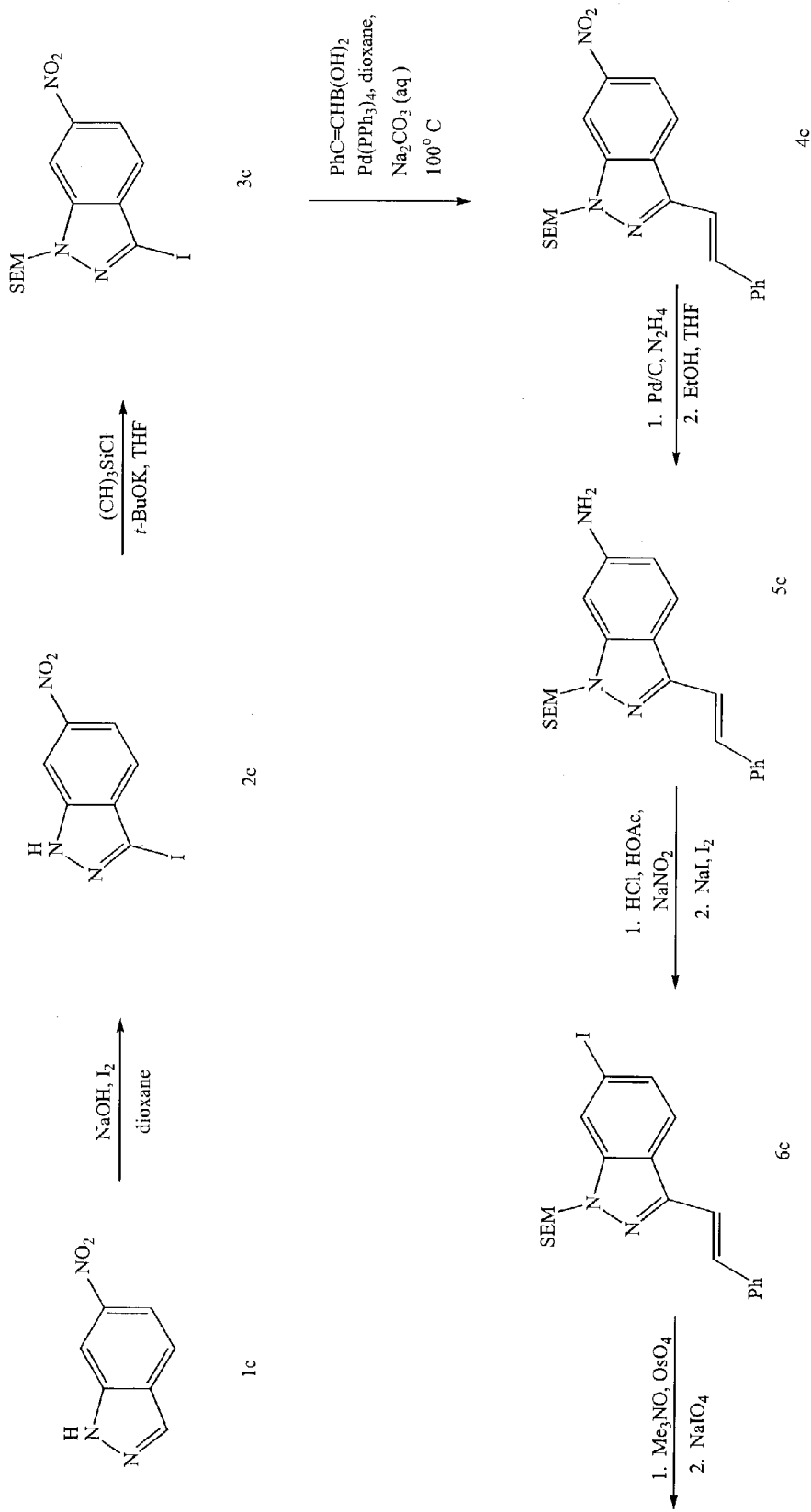
FIGS. 9A–9B show a reaction scheme for the synthesis of compound 10c.
Figure 9B:
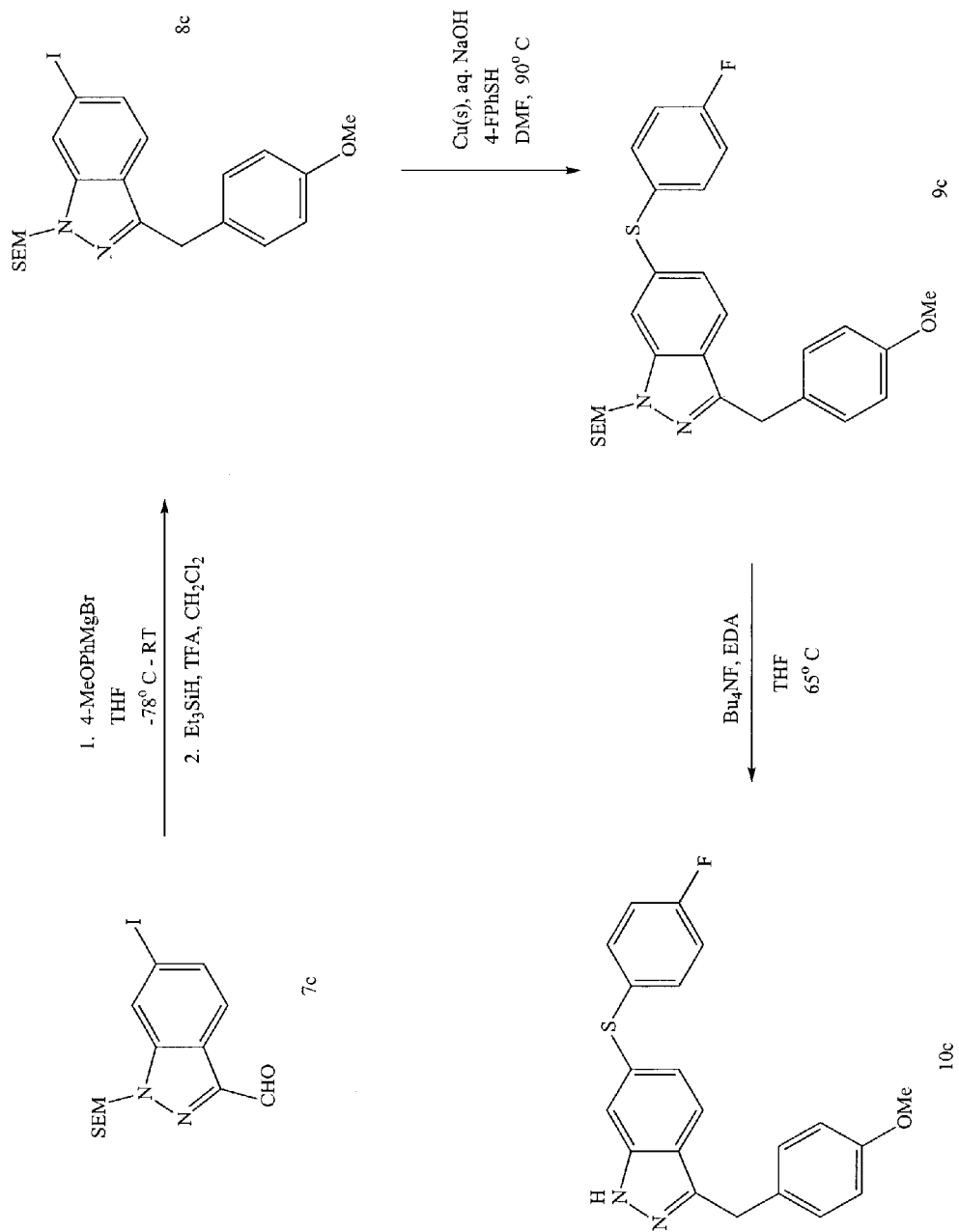

FIG. 9 shows the reaction scheme for the synthesis of compound 10c having the general Formula IV.

Step A: In a round-bottom flask, 6-nitroindole (compound 1c; 15.5 g, 95 mmols) was dissolved in 1,4-dioxane (400 mL). NaOH (3.8 g, 95 mmols) was added, and the reaction mixture was stirred for 10 minutes. Then, 266 mL of 2 N NaOH was added to the reaction mixture, followed by the addition of iodine crystals (two portions of 54.4 g for a total addition of 214 mmols), and the reaction mixture was stirred for 12 hours. The reaction mixture was quenched with 10% citric acid and diluted with EtOAc. The organic layer was washed with 10% $NaHSO_3$, $NaHCO_3$, and brine, dried over $Na_2SO_4$, filtered, and concentrated to provide 27.5 mg of compound 2c as an orange solid.

Step B: Compound 2c (5.18 g) was dissolved in 50 mL of anhydrous THF under an atmosphere of dry nitrogen. To this solution was added 18.8 mL of a 1.0 M solution of potassium tert-butoxide in THF. The reaction mixture was stirred for approximately 15 minutes after which time 3.20 mL of chlorotrimethylsilane was added. The reaction mixture was then partitioned between EtOAc and saturated aqueous $NaHCO_3$. The organic phase was dried over $Na_2SO_4$, filtered and concentrated under vacuum. The resulting residue was purified on a Biotage column to provide 3.85 g of compound 3c as a yellow solid.

Step C: Compound 3c (3.85 g), 766 g of trans-2-phenylvinylboronic acid, 531 mg of $Pd(PPh_3)_4$ and 14.20 mL of 2.0 M $Na_2CO_3$ were dissolved/suspended in 50 mL of dioxane under an atmosphere of dry nitrogen. The reaction mixture was heated to reflux overnight, and then cooled to ambient temperature and concentrated under vacuum. The resulting residue was partitioned between $CH_2Cl_2$ and water. The $CH_2Cl_2$ layer was dried over $Na_2SO_4$, filtered and concentrated under vacuum. The resulting residue was purified on a Biotage column to provide compound 4c.

Step D: Compound 4c (573 mg) and 103 mg of 10% Pd/C were dissolved/suspended in 10 mL of a 3:1 solution of EtOH/THF under an atmosphere of dry nitrogen. To this solution was added 500 μL of hydrazine, and the reaction mixture was stirred for 2 hours at ambient temperature. The reaction mixture was then filtered through Celite, the Celite was washed with EtOH and $CH_2Cl_2$, and the filtrate was concentrated under vacuum. The resulting residue was partitioned between $CH_2Cl_2$ and water. The $CH_2Cl_2$ layer was washed with water and brine, dried over $Na_2SO_4$, filtered and concentrated under vacuum to provide compound 5c.

Step E: Compound 5c (2.51 g) was dissolved in a solution of 30 mL of acetic acid and 6 mL of water under an atmosphere of dry nitrogen. To this reaction mixture was added 3.2 mL of concentrated HCl. The reaction was then cooled to 0° C., and 535 mg of sodium nitrite was added. The reaction mixture was then stirred for about 30 minutes after which time a 4.0 mL aqueous solution of 1.23 mg of sodium iodide and 885 mg of iodine was added to the reaction mixture. After about 4 hrs, the reaction mixture was quenched with aqueous saturated $NaHCO_3$ (slow addition) and then partitioned between $CH_2Cl_2$ and water. The $CH_2Cl_2$ layer was dried over $Na_2SO_4$, filtered and concentrated under vacuum. The resulting residue was purified on a Biotage column to give 1.90 g of compound 6c.

Step F: Compound 6c (1.90 g) and 509 mg of trimethylamine-N-oxide dihydrate were dissolved in 30 mL of $CH_2Cl_2$ under an atmosphere of dry nitrogen. To this reaction mixture was added 51 mg of osmium tetroxide. The reaction mixture was stirred for 12 hours at room temperature. Sodium periodate (1.71 g) dissolved in about 30 mL of water was added, and the reaction mixture was stirred for 1 hour. The reaction mixture was then partitioned between EtOAc and water. The EtOAc layer was washed with brine, dried over $Na_2SO_4$, filtered and concentrated under vacuum. The resulting residue was purified on a Biotage column to give 889 mg of compound 7c.

Step G: Compound 7c (460 mg) was added to 10 mL of anhydrous THF under an atmosphere of dry nitrogen. The mixture was cooled to −78° C. and then 2.80 mL of 4-methoxyphenyl magnesium bromide in THF (0.5 M) was added. The reaction mixture was slowly warmed to room temperature, quenched with water and partitioned between EtOAc and saturated aqueous $NaHCO_3$. The organic layer was dried over $Na_2SO_4$, filtered and concentrated under vacuum. The resulting residue was purified on a Biotage column to give 320 mg of an intermediate product. The intermediate product (151 mg) was dissolved in 1 mL of $CH_2Cl_2$ and 60 μL of triethylsilane under an atmosphere of dry nitrogen. To this reaction mixture was added 1 mL of trifluoroacetic acid. The reaction mixture was then concentrated under vacuum and the residue was partitioned between $CH_2Cl_2$ and aqueous saturated $NaHCO_3$. The $CH_2Cl_2$ layer was dried over $Na_2SO_4$, filtered and concentrated under vacuum. The resulting residue was purified on a Biotage column, eluting with a gradient from 10:1 hexane/$CH_2Cl_2$ to 100% $CH_2Cl_2$, to give 76.6 mg of compound 8c.

Step H: Compound 8c (151 mg), 80 μL of 4-fluorophenylthiol, 12.0 mg of copper powder and 300 μL of 5.0 M aqueous NaOH were added to 1 mL of anhydrous DMF in a sealed tube and then heated to 90° C. for 16 hours. The reaction mixture was partitioned between $CH_2Cl_2$ and 1.0 M aqueous NaOH. The $CH_2Cl_2$ layer was washed with 1.0 M aqueous NaOH, 3.0 N aqueous $NH_4OH$, and brine, dried over $Na_2SO_4$, filtered and concentrated under vacuum. The residue was purified on a Biotage column to give 76.6 mg of compound 9c.

Step I: Compound 9c (76.6 mg) and 100 μL of ethylenediamine were dissolved in 1.6 mL of 1.0 M solution of tetrabutylammonium fluoride in THF under an atmosphere of dry nitrogen. The reaction mixture was heated to reflux for about 12 hours. The reaction mixture was then cooled to room temperature and partitioned between $CH_2Cl_2$ and water. The $CH_2Cl_2$ layer was washed with 10% aqueous citric acid and saturated aqueous $NaHCO_3$, dried over $Na_2SO_4$, filtered and concentrated under vacuum. The residue was purified on a Biotage column, eluting with a gradient from 5:1 hexane/$CH_2Cl_2$ to 100% $CH_2Cl_2$ to give 25 mg of compound 10c.

Example 10

Preparation of [6-(4-fluorophenylsulfanyl)-1H-indazole-3-yl]methanol (14c)

Figure 10:
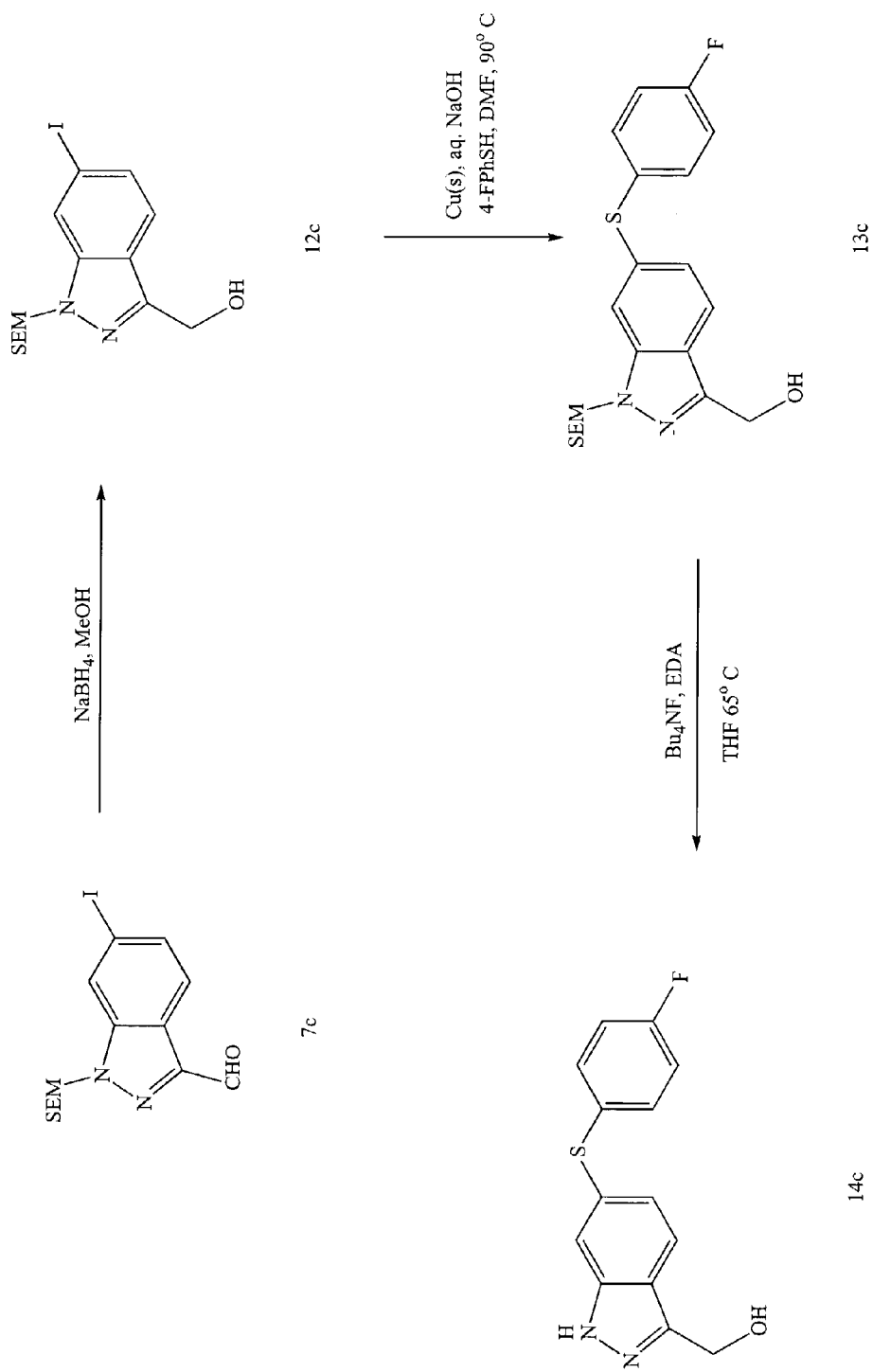
FIG. 10 shows a reaction scheme for the synthesis of e compound 14c.

FIG. 10 shows the reaction scheme for the synthesis of compound 14c having the general Formula IV.

Step A: Compound 7c (520 mg), prepared according to Example 9, was dissolved in 5 mL of methanol under an atmosphere of dry nitrogen. To this solution was added 98.3 mg of sodium borohydride. After about 30 minutes, the reaction mixture was concentrated under vacuum and then partitioned between $CH_2Cl_2$ and water. The $CH_2Cl_2$ layer was dried over $Na_2SO_4$, filtered and concentrated under vacuum. The resulting residue was purified on Biotage column to provide compound 12c.

Step B: Compound 12c (151 mg), methanol, 100 μL of 4-fluorophenylthiol, 6.0 mg of copper powder and 250 μL of 5.0 M aqueous NaOH were added to 1 mL of anhydrous DMF in a sealed tube and then heated to 90° C. for about 30 hours, after which the reaction mixture was cooled to ambient temperature and partitioned between $CH_2Cl_2$ and 1.0 M aqueous NaOH. The $CH_2Cl_2$ layer was washed with 1.0 M aqueous NaOH, 3.0 N aqueous $NH_4OH$, and brine, dried over $Na_2SO_4$, filtered, and concentrated under vacuum. The resulting residue was purified on a Biotage column, eluting with 5:1 $CH_2Cl_2$/EtOAc, to give 67.9 mg of compound 13c.

Step C: Compound 13c (67.9 mg) and 100 μL of ethylenediamine were dissolved in 1.5 mL of tetrabutylammonium fluoride in THF (1.0 M) under an atmosphere of dry nitrogen. The reaction mixture was heated to reflux for about 12 hours, and then cooled to room temperature and partitioned between $CH_2Cl_2$ and water. The $CH_2Cl_2$ layer was washed with 10% aqueous citric acid and saturated aqueous $NaHCO_3$, dried over $Na_2SO_4$, filtered, and concentrated under vacuum. The resulting residue was purified on a Biotage column to give 18 mg of compound 14c.

Example 11

Preparation of 6-(4-fluoro-phenylsulfanyl)-3-methoxymethyl-1H-indazole (17c)

Figure 11:
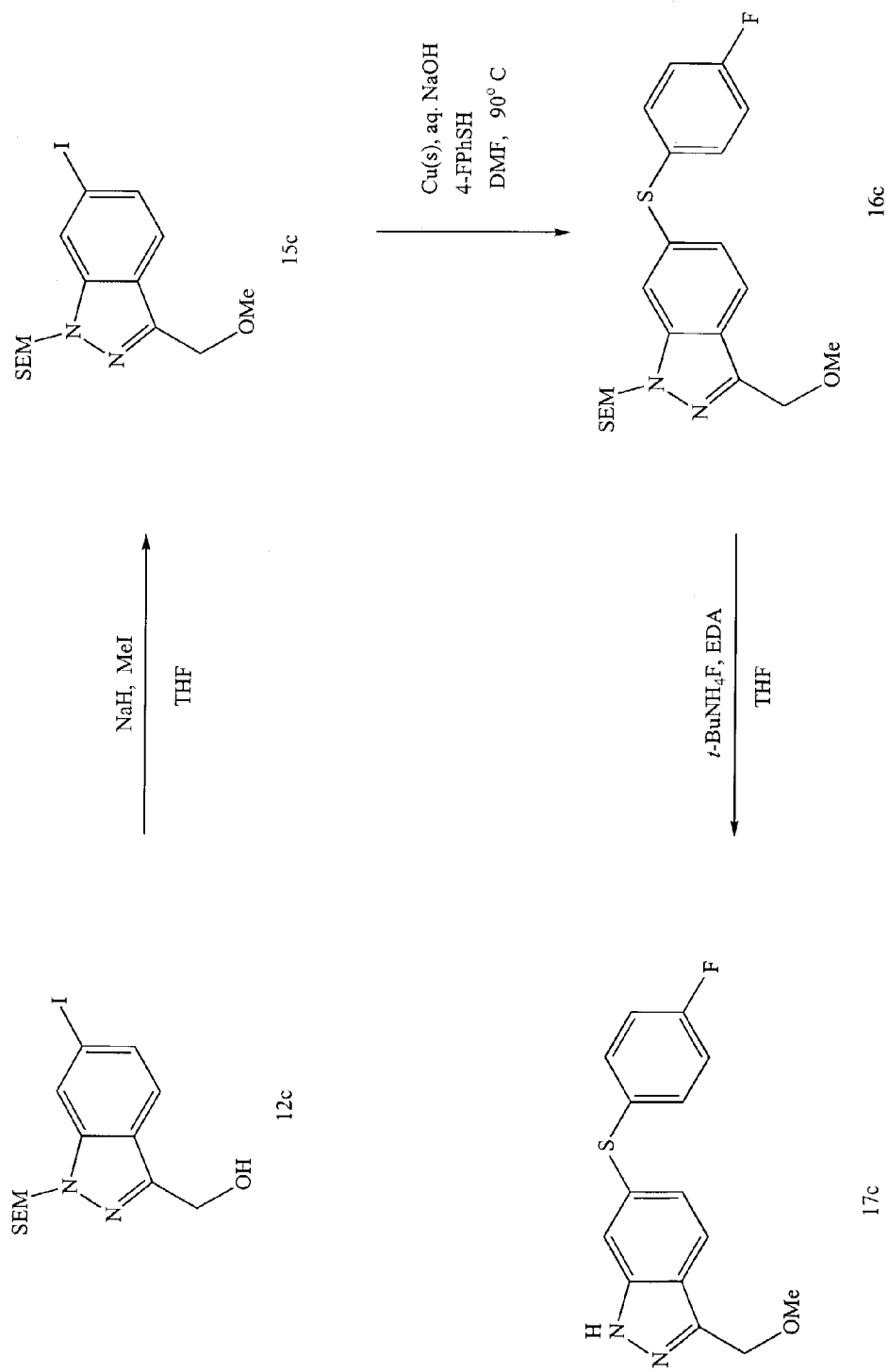
FIG. 11 shows a reaction scheme for the synthesis of compound 17c.

FIG. 11 shows the reaction scheme for the preparation of compound 17c having the general Formula IV.

Step A: Compound 12c (186 mg), prepared according to Example 10, Step A, was dissolved in 5 mL of anhydrous THF under an atmosphere of dry nitrogen. To this solution was added 36.8 mg of sodium hydride (60% in oil), the reaction was stirred for about 15 minutes, and then 60 μL of methyl iodide was added to the reaction mixture. After about 1 hour the reaction mixture was quenched with water and partitioned between $CH_2Cl_2$ and aqueous saturated $NaHCO_3$. The $CH_2Cl_2$ layer was dried over $Na_2SO_4$, filtered, and concentrated under vacuum. The resulting residue was purified on a Biotage column, eluting with 100:1 $CH_2Cl_2$/EtOAc to give 76.1 mg of compound 15c.

Step B: Compound 15c was reacted with 4-fluorothiophenol, copper powder, and aqueous NaOH in DMF in the same manner as in Step B of Example 10 to provide a 22% yield of compound 16c.

Step C: Compound 16c was reacted with tetrabutylammonium fluoride and ethylenediamine in THF in the same manner as in Step C of Example 10 to give a 53% yield of compound 17c.

Example 12

Preparation of 6-(4-fluorophenoxy)-3-methyl-1H-indazole (18c-2)

Figure 12:
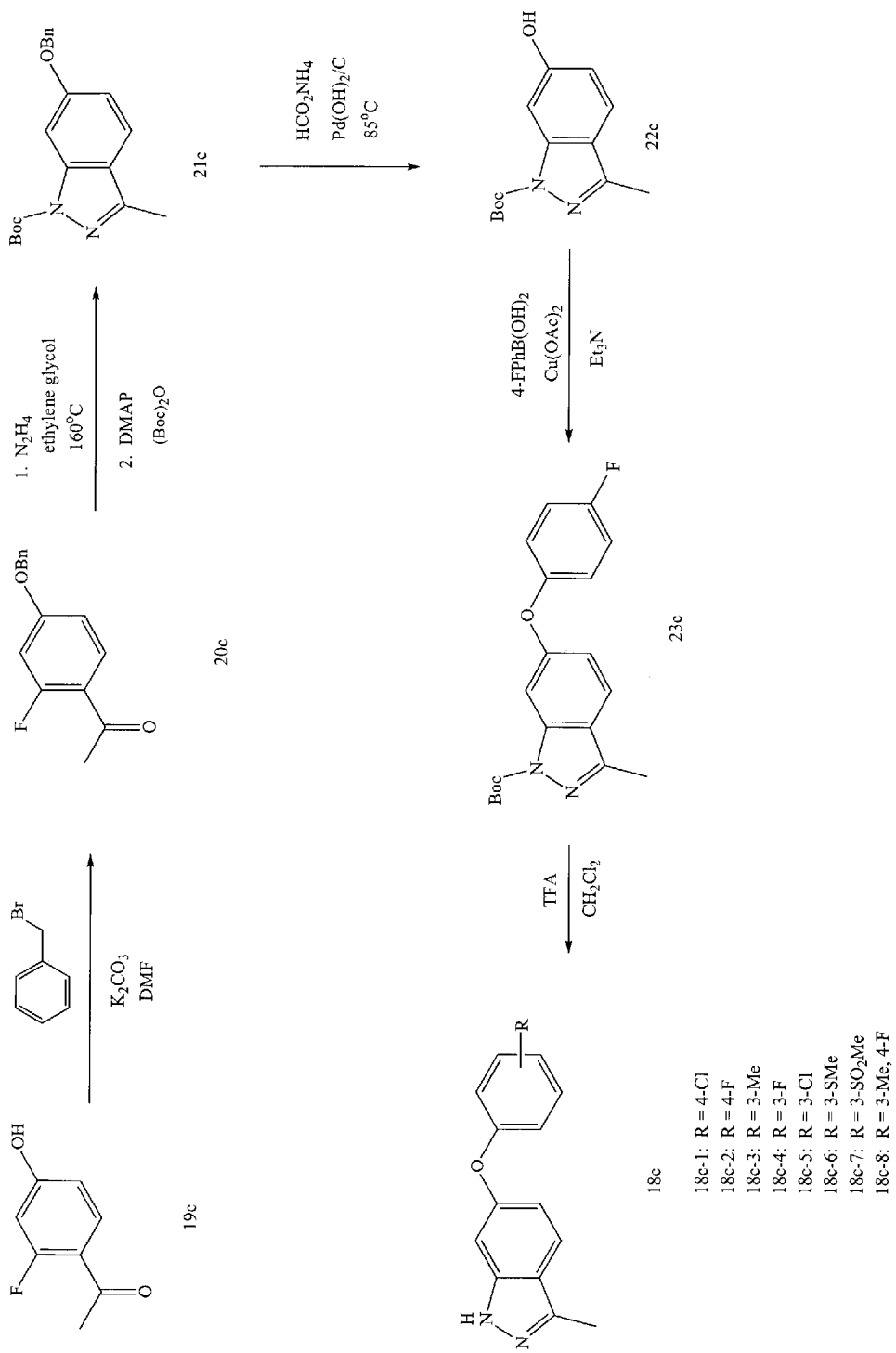
FIG. 12 shows a reaction scheme for the synthesis of compounds having the generic 18c.

FIG. 12 shows the reaction scheme for the synthesis of compounds having the generic structure 18c having the general Formula IV. In this example, the synthesis of compound 18c-2, where Ar is 4-fluorophenyl, is described.

Step A: 2-Fluoro-4-hydroxyacetophenone (compound 19c; 1.42 g) and 1.40 g of potassium carbonate were dissolved/suspended in 30 mL of anhydrous DMF under an atmosphere of dry nitrogen. To this reaction mixture was added 1.20 mL of benzyl bromide. After about 90 minutes the reaction mixture was heated to 65° C. for about 45 minutes, and then cooled to room temperature. The reaction mixture was concentrated under vacuum, and the residue was partitioned between $CH_2Cl_2$ and water. The $CH_2Cl_2$ layer was washed with water and brine, dried over $Na_2SO_4$, filtered and concentrated under vacuum to provide compound 20c.

Step B: Compound 20c (1.87 g) was added to 20 mL of ethylene glycol under an atmosphere of dry nitrogen. To this reaction mixture was added 250 μL of anhydrous hydrazine. The mixture was stirred for 1 hour at room temperature and then heated to 160° C. for about 7 hours. The reaction mixture was then cooled to room temperature and quenched with water. The precipitated salt was collected and air-dried and then further dried by azeotropic removal of water with ethanol and toluene. The precipitated salt was diluted with anhydrous acetonitrile, and then 500 mg of dimethylaminopyridine and 311 mg of di-tert-butyl dicarbonate (BOC anhydride) were added. After all solids were dissolved, the reaction mixture was concentrated under vacuum and the resulting residue was purified on a Biotage column to give 710 mg of compound 21c.

Step C: Compound 21c (710 mg), 662 mg of ammonium formate and 223 mg of Pearlman's catalyst ($Pd(OH)_2/C$) were dissolved/suspended in 20 mL of ethanol under an atmosphere of dry nitrogen. The reaction was heated to 85° C. for about 30 minutes and then filtered through Celite. The Celite was washed with EtOH and the combined filtrates were concentrated under vacuum. The resulting residue was partitioned between $CH_2Cl_2$ and saturated aqueous $NaHCO_3$, dried over $Na_2SO_4$, filtered and concentrated under vacuum to give compound 22c.

Step D: Compound 22c (103 mg), 174 mg of 4-fluorophenylboronic acid, 75 mg of copper (II) acetate, and 300 μL of triethylamine were dissolved/suspended in 2 mL of anhydrous $CH_2Cl_2$, and 4A molecular sieves were added to this solution. The reaction was exposed to air for about 5 hours, and then filtered and concentrated under vacuum. The resulting residue was purified on a Biotage column eluting with $CH_2Cl_2$ to give 85 mg of compound 23c.

Step E: Compound 23c (85 mg) was dissolved in 2 mL of a 1:1 solution of $CH_2Cl_2$/TFA under an atmosphere of dry nitrogen. The reaction mixture was stirred for about 30 minutes, after which time it was concentrated under vacuum. The resulting residue was partitioned between $CH_2Cl_2$ and aqueous saturated $NaHCO_3$. The $CH_2Cl_2$ layer was dried over $Na_2SO_4$, filtered and concentrated under vacuum to provide 18c-2.

To prepare other compounds having the generic structure 18c, compound 22c is reacted with phenyl borate or an appropriately substituted phenyl borate as described in Step D, and then treated as described in Step E.

Example 13

Preparation of 3-ethyl-6-(4-fluorophenylsulfanyl)-1H-indazole (26c)

Figure 13:
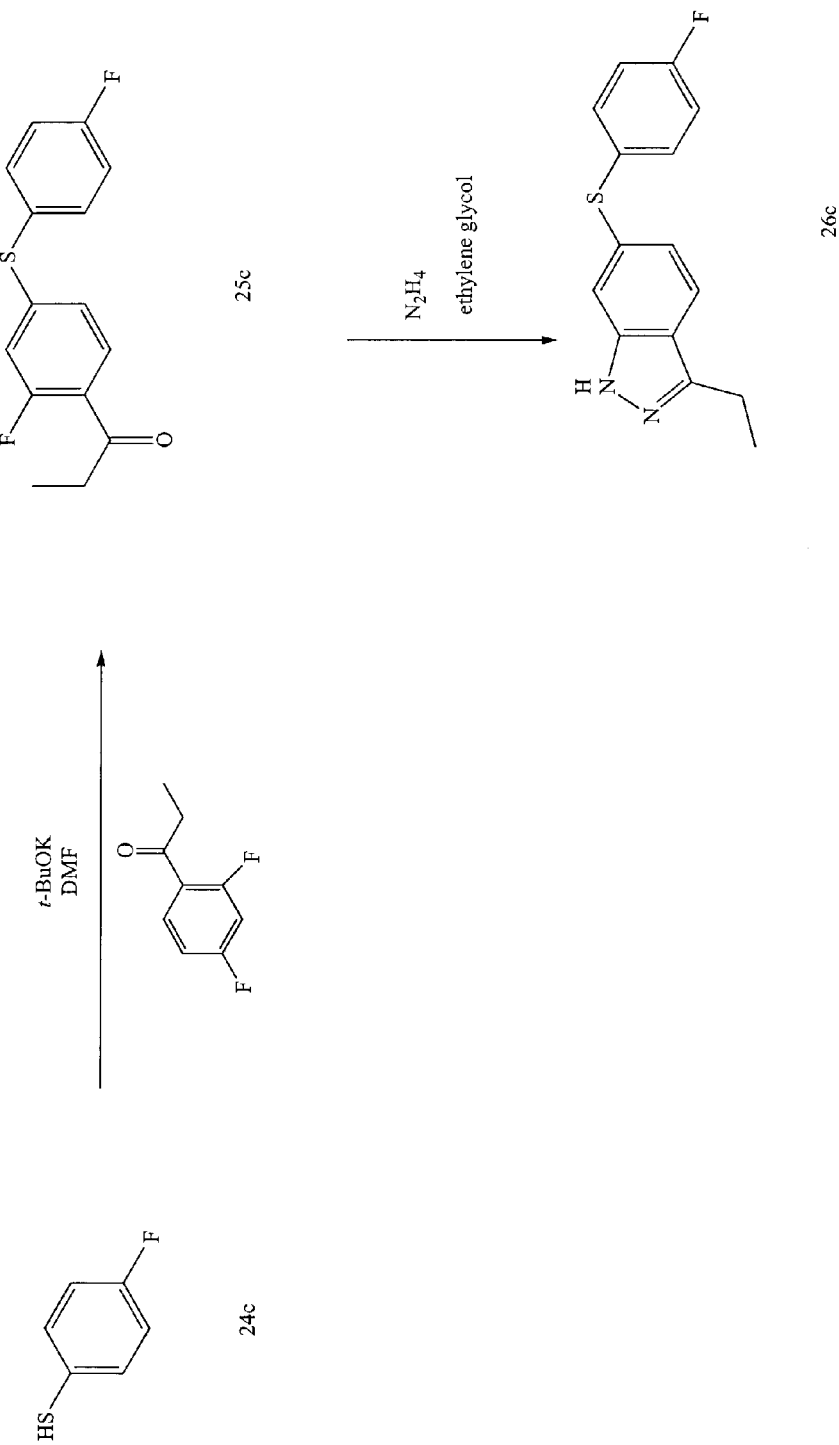
FIG. 13 shows a reaction scheme for the synthesis of compound 26c.

FIG. 13 shows the reaction scheme for the synthesis of compound 26c having the general Formula IV.

Step A: 4-Fluorothiophenol (compound 24c; 900 μL) was dissolved in 40 mL of anhydrous THF under an atmosphere of dry nitrogen. To this solution was added 8.40 mL of potassium tert-butoxide in THF (1.0 M) followed by the addition of 10 mL of anhydrous DMF. The reaction mixture was stirred at ambient temperature for 10 minutes, after which time 1.43 g of 2,4-difluoropropiophenone was added and the mixture was allowed to react for about 12 hours at room temperature. The reaction mixture was then partitioned between $Et_2O$ and water. The $Et_2O$ layer was washed with saturated aqueous $NaHCO_3$, dried over $Na_2SO_4$, filtered and concentrated under vacuum to provide compound 25c.

Step B: Compound 25c (2.34 g) and 260 μL of anhydrous hydrazine were suspended/dissolved in ethylene glycol under an atmosphere of dry nitrogen. The reaction mixture was then heated to about 70° C. for about an hour and then heated to about 160° C. for about 12 hours. The reaction mixture was cooled to room temperature and quenched with about 100 mL of water, and then partitioned between $CH_2Cl_2$ and water. The $CH_2Cl_2$ layer was washed with water and aqueous saturated $NaHCO_3$, dried over $Na_2SO_4$, filtered and concentrated under vacuum. The resulting residue was purified on a Biotage column to give 770 mg of compound 26c.

Example 14

Preparation of 5-(4-fluorophenoxy)-1H-indazol-3-yl-amine (34c)

FIG. 14 shows the reaction scheme for the synthesis of compound 34c having the general Formula VI.

Step A: In a round-bottom flask, 50 mL of MeOH and 200 mL of toluene were added to of 5-fluoro-2-nitrobenzoic acid (compound 27c; 10.0 g, 54.0 mmols). About 41 mL of trimethylsilyldiazomethane (2.0 M) were added slowly with stirring. After bubbling stopped, the reaction was quenched with 1 mL of acetic acid. The reaction mixture was concentrated in vacuum to provide compound 28c.

Step B: In a round-bottom flask, 4-fluorphenol (4.0 g, 35 mmols) was diluted with 100 mL of anhydrous THF. The reaction was cooled to 0° C. with an ice bath, and then 1.0 M potassium tert-butoxide in THF (35 mL, 35 mmols) was slowly added. The reaction mixture was stirred for 10 minutes, and then compound 28c (7.4 g, 37 mmols) in 50 mL of THF was added. The reaction mixture was stirred at 0° C. for 10 minutes and then warmed to room temperature and stirred for about 12 hours. The reaction mixture was concentrated and in the residue was diluted with $CH_2Cl_2$. The $CH_2Cl_2$ was washed with 1N NaOH and brine, and dried over $Na_2SO_4$, filtered, and concentrated to an oil. The oil was purified on a Biotage 40 M column eluting with 50:50 hexane/$CH_2Cl_2$ to provide compound 29c as an oil.

Step C: In a round-bottom flask, compound 29c (40 g, 13 mmols) was added to 60 mL of MeOH followed by the addition of 6 N NaOH (4.3 mL, 26 mmols). The reaction mixture was stirred at room temperature for 4 hours and then concentrated, and the resulting residue was diluted with 50 mL water. About 5 mL of 2N HCl (pH=2.0) was added, and a solid fell out of solution. The solid was dissolved in $CH_2Cl_2$, and the organic layer was washed with brine, dried over $Na_2SO_4$, filtered, and then concentrated in toluene to provide compound 30c as a white solid.

Step D: In a round-bottom flask, compound 30c was dissolved in 40 mL of thionyl chloride and heated to 90° C. for 2 hours. The reaction mixture was cooled and then concentrated down to a yellowish solid. The solid was dissolved in 20 mL of acetone and cooled to 0° C. in an ice bath, and then 10 mL of $NH_4OH$ was added very slowly. The reaction mixture was quenched with water and then concentrated. The resulting residue was extracted with $CH_2Cl_2$, and the $CH_2Cl_2$ was dried over $Na_2SO_4$ and concentrated to provide compound 31c.

Step E: In a round-bottom flask, compound 31c (3.4 g, 12.3 mmols) was dissolved in 100 mL of dichloroethane, and then oxalyl chloride (5.4 mL, 62 mmols) was added and the reaction mixture was heated to 55° C. for 2 hours. The reaction mixture was concentrated, and the resulting oil was stirred in water (50 mL) and then cooled to about 0° C. in an ice bath as $NH_4OH$ was slowly added to quench excess oxalyl chloride. The reaction mixture was extracted with $CH_2Cl_2$, and the organic layer was dried over a $Na_2SO_4$, filtered, and concentrated to provide compound 32c as a dark oil.

Step F: In a round-bottom flask, compound 32c (2.21 g, 8.5 mmols) was diluted with 100 mL EtOH and then $Pd(OH)_2$ (300 mg) was added, followed by the addition of ammonium formate (2.7 g, 43 mmols). The reaction mixture was heated to reflux for 18 hours, filtered through glass paper to remove Pd, and the paper was washed with EtOH. The filtrate was concentrated, and the resulting residue was taken up in $CH_2Cl_2$ and washed with saturated sodium bicarbonate and brine, dried over $Na_2SO_4$, filtered, and concentrated to provide compound 33c as a yellow solid.

Step G: Compound 33c (280 mg, 1.3 mmols) was placed a round-bottom flask in an ice water bath, and 5 mL of HOAc and 2.5 mL of $H_2O$ were added. The reaction mixture was maintained at 0° C., HCl (0.35 mL, 6 mmols) was added, and after 5 minutes $NaNO_2$ (93 mg, 1.3 mmols) was added. After about 1 hour, tin (II) chloride dihydrate (554 mg, 2.5 mmols) was added and the reaction was stirred for 30 minutes. The reaction mixture was then warmed to room temperature, and concentrated, and the residue was taken up in $CH_2Cl_2$. The organic layer was washed with water and brine, filtered, dried over $Na_2SO_4$, filtered, and concentrated to a film. The film was triturated material with $CH_2Cl_2$ and the solids were collected. The solids were then heated in 1-butanol (120° C.) in a pressure tube for 12 hours to induce cyclization, and then the reaction was cooled and the solid was collected by filtration to provide compound 34c.

Example 15

Preparation of N-[6-(4-fluorophenoxy)-1H-indzole-3-yl]-acetamide (38c-1)

FIG. 15 shows the reaction scheme for the synthesis of compounds 38c having the general Formula VI. In this example, the synthesis of compound 38c-1, where X is oxygen, is described.

Step A: 2-Fluoro-4-hydroxybenzonitrile (compound 35c-1; 1.40 g), 2.86 g of 4-fluorophenylboronic acid, 1.86 g of copper (II) acetate, and 7.20 mL of triethylamine were dissolved/suspended in 100 mL of anhydrous $CH_2Cl_2$, and 4A molecular sieves were added to this reaction mixture. The reaction mixture was exposed to air through a drying tube and stirred at ambient temperature for 16 hours. The reaction mixture was filtered, and the filtrate was washed with 10% aqueous $NaHSO_4$, 1N aqueous NaOH, and brine, dried over $Na_2SO_4$, filtered, and concentrated under vacuum to give 530 mg of compound 36c-1.

Step B: Compound 36c-1 (208 mg) and 150 µL of anhydrous hydrazine were dissolved in 5 mL of butanol. The reaction mixture was heated to reflux under an atmosphere of dry nitrogen for 15 hours, then cooled to ambient temperature, concentrated under vacuum and triturated with ethyl ether. The resulting pink solid, compound 37c-1, was collected via filtration, washed with ethyl ether, and then air-dried.

Step C: Compound 37c-1 (97 mg) and 40 µL of acetic anhydride were suspended/dissolved in dichloroethane under an atmosphere of dry nitrogen. The reaction mixture was heated to 60° C. for about 1 hour, then cooled to room temperature and stirred for 12 hours. The white precipitate, compound 38c-1, was collected by suction filtration and then air-dried.

Example 16

Preparation of 2-[6-(4-fluorophenoxy)-1H-indazol-3-yl]-isoindole-1,3-dione (39c)

Figure 16:
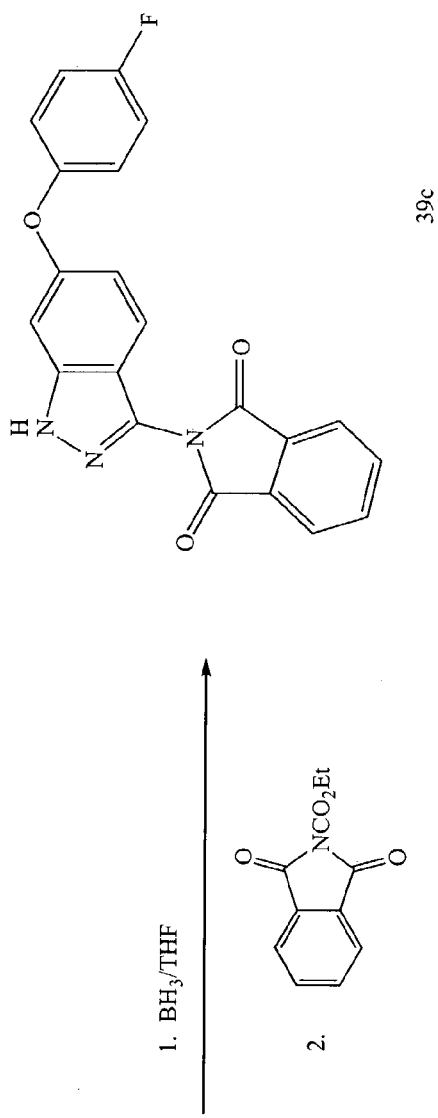
FIG. 16 shows a reaction scheme for the synthesis of compound 39c.
Figure 16:
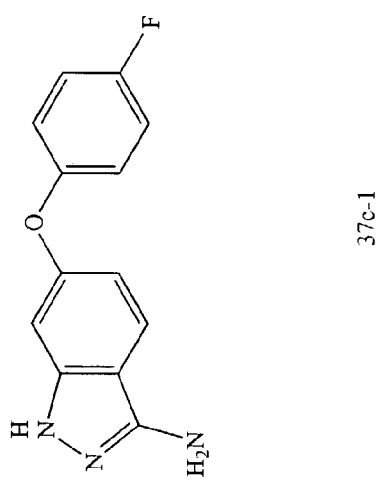

FIG. 16 shows the reaction scheme for the synthesis of compound 39c having the general Formula VI.

Step A: Compound 37c-1, prepared according to Example 15, was dissolved in 1 mL of borane in THF (1.0 M) under an atmosphere of dry nitrogen. The solution was heated to 60° C. for about 2 hours, then cooled to room temperature and quenched by the slow addition of methanol (3 mL). The reaction mixture was concentrated under vacuum, and the resulting residue was purified on a Biotage column eluting with 3:1 $CH_2Cl_2$/EtOAc to provide compound 37c-1.

Step B: Compound 37c-1 (660 mg) and 654 mg of N-carboethoxyphthalimide were suspended/dissolved in 15 mL of dichloroethane under an atmosphere of dry nitrogen at room temperature for about 13 hours. After about 20 minutes the reaction mixture was heated to 65° C. for about 5.5 hours, after which it was cooled to room temperature and filtered. The white precipitate, compound 39c, was washed with dichloroethane and then air-dried.

Example 17

Preparation of 3-(1,3-dihydroisoindol-2-yl)-6-(4-fluorophenoxy)-1H-indazole (40c)

Figure 17:
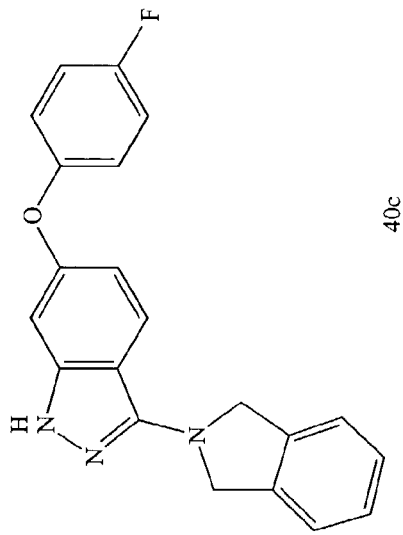
FIG. 17 shows a reaction scheme for the synthesis of compound 40c.
Figure 17:
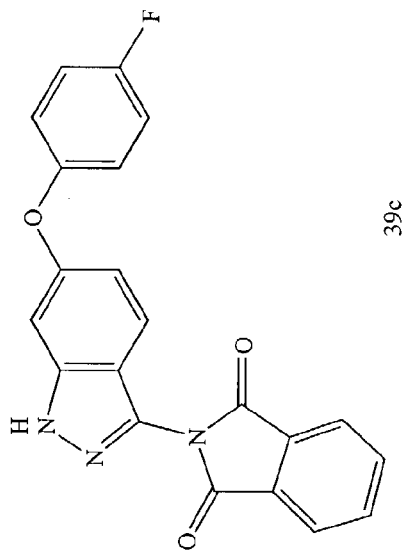

FIG. 17 shows the reaction scheme for the synthesis of compound 40c having the general Formula VI. Compound 39c (25 mg), prepared according to Example 16, was suspended in 1 mL of anhydrous THF under an atmosphere of dry nitrogen. To this solution was added 1.0 mL of a 1.0 M solution of $BH_3$ in THF. The reaction mixture was stirred at room temperature for about 1 hour, and then heated to reflux for 2 hours. The reaction mixture was then cooled to room temperature and 2.0 mL of methanol was carefully added. The mixture was stirred for about 10 minutes and then concentrated under vacuum. The resulting residue was purified on a Biotage column to give 5 mg of compound 40c.

Example 18

Preparation of 5-(4-fluorophenylsulfanyl)-1-H-indazole (4d)

FIG. 18 shows the reaction scheme for the synthesis of compound 4d having the general Formula VII.

Step A: A mixture of 6-iodo-1H-indazole (compound 1d) in $CH_3CN$ (11 mL) was treated with triethylamine and dimethylaminopyridine. After cooling to 0° C., a solution of di-tert-butyl dicarbonate (BOC anhydride) in $CH_3CN$ (10 mL) was added dropwise. After stirring at room temperature for 3 hours, the reaction mixture was concentrated in vacuum and the resulting residue was partitioned between $H_2O$ and ether. The pH was adjusted to 2 with 1N HCl and the organic phase was separated, dried ($Na_2SO_4$), filtered and concentrated in vacuum to provide compound 2d as an oil.

Step B: A mixture of compound 2d in DMF (25 mL) was treated with 5N KOH, Cu powder, and ArSH. In this example, ArSH was 4-fluorothiophenol. The reaction mixture was heated at 110° C. for 48 hours, then cooled to room temperature, concentrated in vacuum, acidified with 1N HCl, and extracted into $CH_2Cl_2$. The organic layer was filtered through 1PS paper, concentrated in vacuum, and the resulting residue was purified on a Biotage column, eluting with 100% $CH_2Cl_2$, 5% $Et_2O/CH_2Cl_2$, and then 10% $Et_2O/CH_2Cl_2$ to provide compound 4d.

Example 19

Preparation of 5-(4-fluorophenylsulfanyl)-1-isopropyl-1H-indazole (5d-1)

FIG. 19 shows the reaction scheme for the synthesis of compounds having the generic structure 5d having the general Formula VII. In this example, the synthesis of compound 5d-1, where R is isopropyl, is described.

A solution of compound 4d, prepared according to Example 18, in THF (1 mL) was treated with powdered KOH followed by the addition of 18-crown-6 and RI. In this example, RI was isopropyl iodide. The reaction mixture was stirred at room temperature for 18 hours under a nitrogen atmosphere. The reaction mixture was then diluted with $CH_2Cl_2$ and filtered, the filtrate was concentrated in vacuum, and the residue was diluted with $CH_2Cl_2$. The organic layer was washed with saturated aqueous $NaHCO_3$, filtered through 1PS paper, and concentrated in vacuum. The resulting residue was purified on a Biotage column, eluting with 4:1 hexane/$Et_2O$ to provide compound 5d-1 as a yellow oil.

Example 20

Preparation of 5-iodo-1-(4-methoxybenzyl)-1H-indazole (8d-1)

Figure 20:
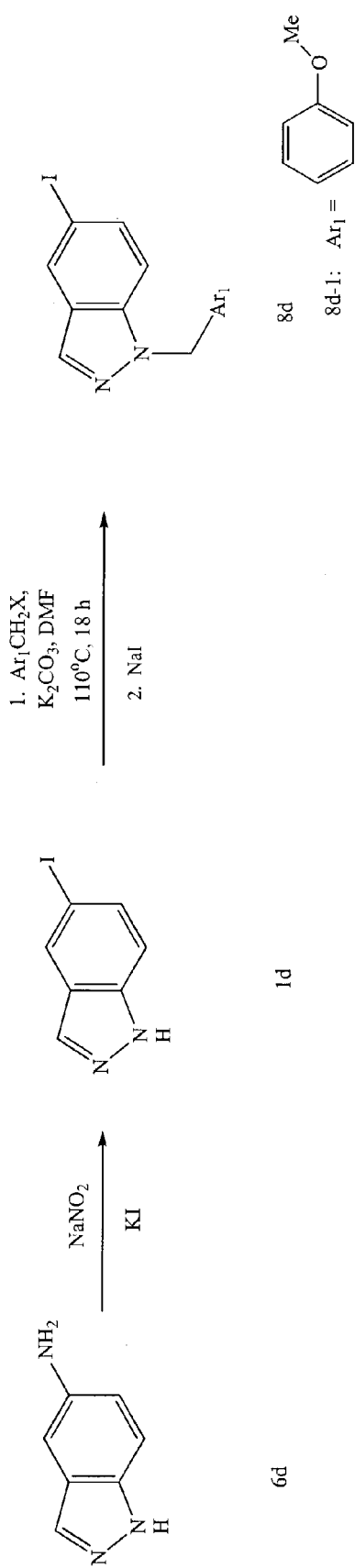
FIG. 20 shows a reaction scheme for the synthesis of compound 8d.

FIG. 20 shows the reaction scheme for the synthesis of compounds 8d. In this example, the synthesis of compound 8d-1, where Ar1 is 4-methoxyphenyl, is described.

Step A: A suspension of 5-aminoindazole (compound 6d) in 6M HCl (150 mL) was cooled to 0° C. and treated dropwise with a solution of $NaNO_2$ in water (15 mL). After stirring at 0° C. for 30 minutes, the reaction mixture was added to a cold solution of KI in water (105 mL). The mixture was allowed to warm to room temperature and stirring was continued at room temperature for 18 hours. The mixture was quenched with 10% $Na_2S_2O_3$ and extracted with $Et_2O$. The biphasic mixture was filtered and the insoluble solids were washed with water and dried in vacuum overnight. The organic phase was separated and further washed with aqueous saturated $NaHCO_3$, water, filtered through 1PS paper, evaporated in vacuum to a pink residue.

Step B: A solution of compound 1d in DMF was treated with $K_2CO_3$, followed by the addition of a substituted or unsubstituted benzyl halide at room temperature in a nitrogen atmosphere. In this example, the benzyl halide was benzyl chloride. The mixture was heated at 100° C. for 48 hours in a nitrogen atmosphere. The mixture was treated with 0.2 equivalents of NaI (123 mg) and heating was continued for 18 hours. The solvent was evaporated in vacuum and the residue taken up in $CH_2Cl_2$ and 1N HCl. The organic layer was separated, washed with aqueous saturated $NaHCO_3$, and concentrated to afford an oil. The oil was purified on a Biotage column, eluting with a gradient of 3:1 hexane/$Et_2O$ to 3:2 hexane/$Et_2O$, to provide compound 8d-1.

Example 21

Preparation of 5-(4-fluorobenzenesulfonyl)-1-(4-methoxybenzyl)-1H-indazole (10d-1)

FIG. 21 shows the reaction scheme for the synthesis of compounds 10d having the general Formula IX. In this example, the synthesis of compound 10d-1, where Ar¹ is 4-methoxyphenyl and Ar² is 4-fluorophenyl, is described.

Step A: A mixture of compound 8d, 5 N KOH, copper powder, and Ar$_2$SH in a solution of water and DMF was heated at reflux for about 18 hours. In this example, Ar$_2$SH was 4-fluorothiophenol. The mixture was then cooled to room temperature, acidified with 1N HCl, and extracted with CH$_2$Cl$_2$. The organic layer was filtered through 1PS paper, concentrated in vacuum, and the resulting residue was purified on a silica gel SepPak cartridge eluting with 4:1 hexane/Et$_2$O to provide compound 9d.

Step B: A solution of compound 9d in acetone (0.2 mL) containing MgSO$_4$ was treated with a solution of NaIO$_4$ and KMnO$_4$ in water (0.2 mL) and the reaction mixture was stirred at room temperature for 18 hours. The reaction mixture was then treated with aqueous sodium bisulfite, and extracted with CH$_2$Cl$_2$. The organic layer was filtered through 1PS paper and concentrated in vacuum to provide 2.1 mg of compound 10d as a yellow oil.

Example 22

Preparation of 5-(4-fluorobenzenesulfinyl)-1-(4-methoxybenzyl)-1H)-indazole (11 d-1)

FIG. 22 shows the reaction scheme for the synthesis of compound 11d-1 having the general Formula VIII. A solution of compound 9d-1, prepared according to Example 21, in 1:1 water/acetonitrile was treated with NaIO$_4$ and the reaction mixture was stirred at room temperature for 18 hours. The reaction mixture was then filtered, and the filtrate was concentrated in vacuum. The resulting residue was partitioned between water and CH$_2$Cl$_2$. The organic layer was separated, filtered through 1PS paper, concentrated in vacuum, and purified on a silica gel SepPak cartridge eluting with a gradient of 4:1, 2:1, and 1:1 hexane/Et$_2$O to provide compound 11d-1.

Example 23

Preparation of 1-benzenesulfonyl-5-(4-fluorophenyl-sulfanyl)-1H-indazole (13d)

FIG. 23 shows the reaction scheme for the preparation of compound 13d having the general Formula VII.

Step A: A solution of 5-iodoindazole (compound 1d) in pyridine was treated with benzenesulfonyl chloride at room temperature for 18 hours under a nitrogen atmosphere. The reaction mixture was concentrated in vacuum and the residue was taken up in CH$_2$Cl$_2$ and 1N HCl. The organic layer was separated, filtered through 1PS filter paper, and concentrated in vacuum. The resulting residue was purified on a Biotage column eluting with 5:1 hexane Et$_2$O to provide compound 12d.

Step B: A mixture of compound 12d, 5N KOH, copper powder, and 4-fluorothiphenol in a solution of water and DMF was heated at reflux for about 18 hours. The mixture was then cooled to room temperature, acidified with 1N HCl, and extracted with CH$_2$Cl$_2$. The organic layer was filtered through 1PS paper, concentrated in vacuum, and the resulting residue was purified on a silica gel SepPak cartridge eluting with 4:1 hexane/Et$_2$O to provide compound 13d.

Example 24

Preparation of 3-chloro-6-phenoxybenzo[d]isoxazole (8e-1)

FIG. 24 shows the reaction scheme for the synthesis of compounds 8e having the general Formula V. In this example, the synthesis of compound 8e-1, where Ar2 is phenyl, is described.

Step A: A solution of 4-fluoro-2-hydroxybenzoic acid (compound 1e) in MeOH was slowly treated with concentrated H$_2$SO$_4$ and then heated at reflux for 12 days. The reaction mixture was then concentrated in vacuum to a yellow oil, and the oil was taken up in CH$_2$Cl$_2$. The organic layer was washed with saturated aqueous NaHCO$_3$, brine, and water, dried over Na$_2$SO$_4$, filtered and concentrated in vacuum to provide 12.7 g of compound 2e as an amber oil.

Step B: A solution of compound 2e, K$_2$CO$_3$, and benzyl chloride in DMF (200 mL) was heated at 95° C. for 18 hours. The mixture was filtered and the filtrate was concentrated in vacuum to a yellow oil. The oil was purified on a Biotage column, eluting with 7:2 hexane/EtOAc to provide 19.4 g of compound 3e as a clear oil.

Step C: A solution of compound 3e in DMSO (2 mL) was treated with K$_2$CO$_3$, followed by the addition of Ar$_2$OH at room temperature in a nitrogen atmosphere. In this example, Ar$_2$OH was phenol. The mixture was heated at 90° C. for 3 days in a nitrogen atmosphere. Water (1 mL) was slowly added, and the product extracted with EtOAc. The aqueous layer was separated and extracted with EtOAc. The combined organic extracts were washed with brine, dried over Na$_2$SO$_4$, filtered and concentrated in vacuum to a dark oil. The oil was purified on a Biotage column, eluting with 6:1 hexane/Et$_2$O, to provide compound 4e-1 as a clear oil.

Step D: A 1.0 M solution of compound 4e-1 in MeOH (30 mL) was purged with nitrogen and treated with 20% Pd(OH)$_2$/C (15% wt=297 mg). The reaction mixture was purged with additional nitrogen and then stirred at room temperature for 2 days under hydrogen. The catalyst was filtered off and washed with MeOH. The filtrate was evaporated in vacuum to a clear oil, which was purified on a Biotage column, eluting with 5% Et$_2$O/hexane, to provide compound 5e-1 as a clear oil.

Step E: 3M NaOH (9 mL) was added to a solution of NH$_2$OH.HCl in water (14 mL), followed by addition of a solution of compound 5e-1 in dioxane (10 mL). The cloudy mixture was stirred at room temperature for 18 hours in a nitrogen atmosphere. The resulting clear mixture was cooled in an ice bath, acidified with 2M HCl, and extracted with EtOAc. The combined organic layers were washed with brine, filtered through 1PS paper and evaporated in vacuum to provide 235 mg of a beige solid. This solid was triturated in 4:1 hexane/EtOAc, and the resulting white solid, compound 6e-1, was collected by filtration.

Step F: A solution of carbonyldiimidazole in THF was added to a refluxing solution of compound 6e-1 in THF, and refluxing was continued for 18 hours. The mixture was then concentrated in vacuum, diluted with water, acidified with 1N HCl and extracted with CH$_2$Cl$_2$. The organic layer was filtered through 1PS paper, and evaporated in vacuum to provide compound 7e-1 as a pale yellow solid or foam.

Step G: A suspension of compound 7e-1 in POCl$_3$ was treated with triethylamine at room temperature, and the mixture was heated at 110° C. for 6 hours. The mixture was cooled to room temperature and poured into a beaker containing ice water. The product was extracted with CH$_2$Cl$_2$, filtered through 1PS paper and evaporated in vacuum to provide 10 mg of compound 8e-1 as an amber oil.

Example 25

Preparation of 3,6-diphenoxy-benzo[d]isoxazole (9e-1)

FIG. 25 shows the reaction scheme for the synthesis of compounds 9e having the general Formula V. In this example, the synthesis of compound 9e-1, where Ar$^1$ is phenyl and Ar$^2$ is phenyl, is described. A solution of compound 8e-1, prepared according to Example 24, in DMF (1 mL) was added to a mixture of NaH and phenol (1 mL) in DMF. The reaction mixture was heated at 110° C. for 18 hours. The solvent was evaporated in vacuum and the residue was partitioned between 1N HCl and CH$_2$Cl$_2$. The organic layer was separated and filtered through 1PS paper. Evaporate of the solvent afforded a brown oil, which was purified on a silica gel SepPak cartridge eluting with 4:1 hexane/Et$_2$O to provide compound 9e-1 as a clear oil that solidified to long white needles.

Example 26

Preparation of (4-methoxy-phenyl)-(6-phenoxy-benzol[d]isoxazol-3-yl)-amine (10e-1)

FIG. 26 shows the reaction scheme for the synthesis of compounds 10e having the general Formula V. In this example, the synthesis of compound 10e-1, where Ar$^1$ is 4-methoxyphenyl and Ar$^2$ is phenyl, is described. A solution of Ar$^1$NH$_2$ in THF was cooled to −78° C. and treated with n-butyl lithium under a nitrogen atmosphere. In this example, Ar1NH2 was aniline. After stirring at −78° C. for 20 minutes, a solution of compound 8e-1, prepared according to Example 25, in THF was added under nitrogen. The mixture was slowly warmed to room temperature, then quenched with aqueous saturated NH4Cl extracted with CH$_2$Cl$_2$. The organic layer was washed with 1N HCl and water, filtered through 1PS paper, concentrated in vacuum and purified on a SepPak cartridge eluting with 4:1 hexane/Et$_2$O to provide compound 10e-1 as a yellow oil.

Example 27

Preparation of (2,4-difluorophenyl)-(1-isobutyl-1H-indazol-5-yl)-methanone oxime (7f-1)

FIG. 27 shows the synthetic reaction scheme for the synthesis of compounds 7f having the general Formula XII. In this example, the synthesis of compound 7f-1, where R$^1$ is isobutyl, R$^2$ is H, and Ar is 2,4-difluorophenyl is described.

Step A: Ammonium tetrafluoroborate (20.97 g, 200 mmol) was dissolved in aqueous acetic acid (500 mL AcOH/250 mL water) and cooled to 0° C. 4-Bromo-2-methyl aniline (compound 1f, 18.61 g, 100 mmol) and 42 mL of aqueous concentrated HCl (36% w/w, 12N, 500 mmol) were sequentially added. The mixture was stirred for 20 minutes at 0° C., and then NaNO$_2$ (7.59 g, 110 mmol) was added. The reaction was stirred for 1 hour at 0° C. and warmed to room temperature. After 16 hours at room temperature, the mixture was concentrated under reduced pressure and the residue was azeotroped with toluene and dried under high vacuum. The solid was suspended in 500 mL of CHCl$_3$ and KOAc (12.76 g, 130 mmol) and 18-crown-6 (7.93 g, 30 mmol) were added. The reaction was stirred for 1.5 hours at room temperature. The mixture was washed with water, dried over anhydrous MgSO$_4$, filtered through Celite and concentrated under reduced pressure to provide 30 g of 5-bromo-1H-indazole (2f) as a tan solid. The crude material was used without further purification.

Step B: Crude compound 2f (100 mmol) was dissolved in 250 mL of DMF. K$_2$CO$_3$ (20.7 g, 150 mmol) and 1-bromo-2-methylpropane (16.3 mL, 150 mmol) were added. The mixture was heated to 120° C. under nitrogen atmosphere for 16 hours. The mixture was cooled to room temperature and concentrated under reduced pressure. Water (200 mL) and CH$_2$Cl$_2$ (200 mL) were added to the residue and stirred vigorously for 30 minutes. The layers were separated and the aqueous layer was extracted with CH$_2$Cl$_2$. The combined extracts were dried over anhydrous MgSO$_4$, filtered through Celite, and concentrated under reduced pressure to provide about 30 g of crude. The crude was purified by chromatography (1:9 to 1:4 ether/hexanes) to provide 12.87 g of compound 3f-1 as a dark red oil, yielding 50.8% for Steps A and B. MS ESI (+) m/z 253 and 255 (M+1) detected. $^1$H-NMR (400 MHz, CDCl$_3$) δ 7.93 (s, 1H), 7.87 (m, 1H), 7.43 (m, 1H), 7.29 (m, 1H), 7.29 (m, 1H), 4.15 (m, 2H), 2.33 (m, 1H), 0.92 (m, 6H).

Step C: Compound 3f-1 (121.0 mg, 0.478 mmol) was dissolved in 2 mL of ether and cooled to −78° C. To the solution was added t-BuLi (1.70 M in pentane, 0.59 mL, 1.004 mmol). The reaction stirred an additional hour at −78° C. 2,6-Difluorobenzaldehyde (58 µL, 0.526 mmol) was added at −78° C., the cold bath was removed and the reaction slowly warmed to room temperature. The reaction was quenched with 10 mL of water. The layers were separated and the aqueous layer was extracted several times with CH$_2$Cl$_2$. The combined extracts were dried over anhydrous MgSO$_4$, filtered through Celite, concentrated under reduced pressure, and purified by chromatography with 1:1 ether/hexanes to provide compound 4f-1 as a pale yellow crystalline solid (104.5 mg, 69.1% yield). MS ESI (+) m/z 317 (M+1) detected. $^1$H-NMR (400 MHz, CDCl$_3$) δ 7.96 (s, 1H), 7.73 (s, 1H), 7.56 (m, 1H), 7.40~7.35 (m, 2H), 6.91 (m, 2H), 6.78 (m, 1H), 6.22 (m, 1H), 4.15 (m, 2H), 2.39~2.26 (m, 2H, overlapped with —OH), 0.92 (m, 6H).

Step D: Compound 4f-1 (316.3 mg, 1.00 mmol), triacetoxyperiodinane (445.3 mg, 1.05 mmol), and 10 mL of CH$_2$Cl$_2$ were stirred for 2 hours at room temperature. The reaction mixture was quenched with 10 mL of saturated K$_2$CO$_3$ solution and layers were separated. The aqueous layer was extracted with CH$_2$Cl$_2$ and the combined extracts were dried over anhydrous MgSO$_4$, filtered through Celite, and concentrated under reduced pressure. The crude was purified by chromatography with 1:2 ether/hexanes to provide 237.6 mg of compound 5f-1 as a viscous light brown oil (75.6% yield). MS ESI (+) m/z 315 (M+1) detected. $^1$H-NMR (400 MHz, CDCl$_3$) δ 8.16 (s, 1H), 8.11 (s, 1H), 7.99 (m, 1H), 7.60 (m, 1H), 7.47 (m, 1H), 7.03 (m, 1H), 6.94 (m, 1H), 4.21 (m, 2H), 2.37 (m, 1H), 0.95 (m, 6H).

Step E: A mixture of compound 5f-1(96.7 mg, 0.308 mmol), hydroxylamine-HCl (compound 6f-1; 213.8 mg, 3.076 mmol), and 5 mL of pyridine was stirred at room temperature for 65 hours. Excess pyridine was removed under reduced pressure. The residue was dissolved in 20 mL of CH$_2$Cl$_2$. A white solid precipitated, and the mixture was transferred to a separatory funnel and washed with 1N HCl. The organic layer was dried over anhydrous MgSO$_4$, filtered through Celite, concentrated under reduced pressure and purified by chromatography with 1:2 ether/hexanes to provide 66.5 mg of compound 7f-1 as a pale yellow foamy solid (65.5% yield), which was a 1:4 mixture of isomers. MS ESI (+) m/z 330 (M+1) detected.

Example 28

Preparation of (2,4-difluorophenyl)-(1-isobutyl-1H-indazol-5-yl)-methanone O-ethyl-oxime (7f-3)

In this example, the synthesis of compound 7f-3 having the general Formula XII as shown in FIG. 27, where $R^1$ is isobutyl, $R^2$ is ethyl, and Ar is 2,4-difluorophenyl is described. Compound 5f where $R^1$ is isobutyl and Ar is 2,4-difluorophenyl was prepared according to Steps A–D of Example 27. A mixture of a compound 5f (43.3 mg, 0.138 mmol), O-ethyl-hydroxylamine-HCl salt (53.8 mg, 0.551 mmol), and 2 mL of dry pyridine was stirred at room temperature. The mixture was stirred for 90 hours at room temperature. Excess pyridine was removed under reduced pressure. To the residue were added 2 mL of water and 2 mL of $CH_2Cl_2$. The layers were separated and the aqueous layer was extracted with $CH_2Cl_2$. The combined extracts were washed with 1N HCl (20 mL), dried over $MgSO_4$, filtered through Celite, and concentrated under reduced pressure. The residue was purified by chromatography with 1:4 ether/hexanes to provide 21.2 mg of compound 7f-3 as an oil (43.1% yield), which was a 1:9 mixture of isomers.

Example 29

Preparation of {2-[(2,4-difluorophenyl)-(1-isobutyl-1H-indazol-5-yl)-methyleneaminooxy]-ethyl}-carbamic acid tert-butyl ester (7f-5)

In this example, the synthesis of compound 7f-5 having the general Formula XII as shown in FIG. 27, where $R^1$ is isobutyl, $R^2$ is $CH_2CH_2NHBoc$, and Ar is 2,4-difluorophenyl is described. Compound 5f, where $R^1$ is isobutyl and Ar is 2,4-difluorophenyl was prepared according to steps A–D of Example 27. A mixture of compound 5f (50 mg, 0.159 mmol), (2-aminooxyethyl)-carbamic acid tert-butyl ester prepared as described in Example 30 (112 mg, 0.636 mmol), pyridine (1.5 mL), and a drop of 6N HCl-MeOH (1:1 mixture of concentrated HCl and MeOH by volume) was stirred at room temperature for 64 hours. Excess pyridine was removed under reduced pressure and the residue was purified by chromatography with 1:2 ether/hexanes yielding 63.9% yield of compound 7f-5.

Example 30

Preparation of (2-aminooxy-ethyl)-carbamic acid t-butyl ester

FIG. 28 shows the reaction scheme for the synthesis of (2-aminooxy-ethyl)-carbamic acid tert-butyl ester.

Step A: A mixture of (2-bromo-ethyl)-carbamic acid t-butyl ester (2.77 g, 12.39 mmol), N-hydroxyphthalimide (2.02 g, 12.39 mmol), TEA (5.18 mL, 37.16 mmol) and 25 mL of DMF was stirred at room temperature for 64 hours. The mixture was diluted with 100 mL of water. A white solid precipitated and was collected by filtration. The solid was dissolved in $CH_2Cl_2$ (50 mL) and the solution was washed with 1N HCl (20 mL), saturated $NaHCO_3$ (20 mL) water (20 mL), and brine (20 mL). The solution was dried over anhydrous $MgSO_4$, filtered through Celite, and concentrated under reduced pressure to provide 0.842 g of a white solid (22% yield).

Step B: [2-(1,3-dioxo-1,3-dihydroisoindol-2-yloxy)-ethyl]-carbamic acid tert-butyl ester (0.842 g, 2.749 mmol) was dissolved in 20 ml of $CH_2Cl_2$ and methylhydrazine (150 µL, 2.776 mmol) was added at room temperature. As soon as methylhydrazine was added, a white precipitate was formed. The reaction was stirred at room temperature for 72 hours. The reaction mixture was filtered and the filtrate was concentrated under reduced pressure to provide 0.496 g of a viscous oil (102% yield). The crude material was used without further purification.

Example 31

Preparation of (4-fluorophenyl)-(1-isobutyl-1H-indazol-5-yl)-methanone oxime (7f-2)

In this example, the synthesis of compound 7f-2 having the general Formula XII as shown in FIG. 27, where $R^1$ is isobutyl, $R^2$ is H, and Ar is 4-fluorophenyl is described.

Steps A and B: Compound 3f was prepared as described in steps A and B of Example 27.

Step C: Compound 3f-2 (616.3 mg, 2.436 mmol) was dissolved in 20 mL of ether and cooled to −78° C. To the solution was added t-BuLi (1.70 M in pentane, 2.94 mL) dropwise. After the addition of t-BuLi, the mixture was stirred for 30 minutes at −78° C. 4-fluorobenzaldehyde (290 µL, 2.678 mmol) was added dropwise at −78° C. The mixture was slowly warmed to room temperature. The reaction was quenched with $CH_2Cl_2$ and the combined extracts were washed with brine (20 mL), dried over anhydrous $MgSO_4$, filtered through Celite, and concentrated to provide 750 mg of compound 4f-2 as a tan solid. The solid was purified by chromatography with 1:1 ether/hexanes to provide 554 mg of compound 4f-2 as a light brown solid (76.3% yield).

Step D: Compound 4f-2 (100.6 mg, 0.337 mmol) was dissolved in 10 mL of $CH_2Cl_2$ and "Dess Martin periodinane" (triacetoxyperiodinane; 150.2 mg, 0.354 mmol) was added to the solution. The mixture became turbid after 25 minutes at room temperature. The reaction was stirred an additional 30 minutes at room temperature and was transferred to a separatory funnel. The mixture was diluted with 30 mL of $CH_2Cl_2$ and washed with saturated $NaHCO_3$. A yellow insoluble solid was formed between the organic and aqueous layers and was removed. The organic layer was dried over anhydrous $MgSO_4$, filtered through Celite, and concentrated under reduced pressure. The residue was purified by chromatography with 1:1 ether/hexanes to provide compound 5f-2 as an oil in 85.4% yield.

Step E: A mixture of compound 5f-2 (41.6 mg, 0.140 mmol) and hydroxylamine hydrochloride (20.0 mg, 0.281 mmol) in 1 mL of pyridine was stirred overnight at room temperature. After one day, an HPLC trace showed about 50% conversion. An additional 5 equivalents of $NH_2OH$—HCl were added and the reaction was stirred for 72 hours. Excess pyridine was removed under reduced pressure and the residue was purified by chromatography with 1:2 ether/hexanes, to provide 31.4 mg of compound 7f-2 (71.8% yield) as a 1:2 mixture of isomers. MS ESI (+) m/z 312 (M+1) detected.

Example 32

Preparation of (4-fluorophenyl)-(1-isobutyl-1H-indazol-5-yl)-methanone O-ethyl-oxime (7f-4)

In this example, the synthesis of compound 7f-4 having the general Formula XII as shown in FIG. 27, where $R^1$ is isobutyl, $R^2$ is ethyl, and Ar is 4-fluorophenyl is described.

Steps A–D: Compound 5f-2 was prepared as described in steps A–D of Example 31.

Step E: A mixture of compound 5f-2 (51.2 mg, 0.173 mmol), O-ethyl-hydroxylamine-HCl (67.4 mg, 0.691 mmol), and 2 mL of dry pyridine was stirred at room temperature. The mixture was stirred for 90 hrs at room temperature. Excess pyridine was removed under reduced pressure. To the residue was added 2 mL of water and 2 mL of $CH_2Cl_2$. The layers were separated, and the aqueous layer was extracted with $CH_2Cl_2$. The combined extracts were washed with 1 N HCl (20 mL), dried over anhydrous $MgSO_4$, filtered through Celite, and concentrated under reduced pressure. The residue was purified by chromatography with 1:4 ether/hexanes to provide 47.1 mg of compound 7f-4 as an oil (80.3% yield), which was a 1:2 mixture of isomers. MS ESI (+) m/z 340 (M+1) detected.

Example 33

Preparation of {2-[(4-fluorophenyl)-(1-isobutyl-1H-indazol-5-yl)-methyleneaminooxy]-ethyl}-carbamic acid tert-butyl ester (7f-6)

In this example, the synthesis of compound 7f-6 having the general Formula XII as shown in FIG. 27, where $R^1$ is isobutyl, $R^2$ is $CH_2CH_2NHBoc$, and Ar is 4-fluorophenyl is described.

Steps A–D: Compound 5f-2 was prepared as described in steps A–D of Example 31.

Step E: A mixture of compound 5f-2, (2-aminooxyethyl)-carbamic acid tert-butyl ester prepared as described in Example 30 (120 mg, 0.675 mmol), pyridine (1.5 mL), and a drop of 6N HCl/MeOH (1:1 mixture of concentrated HCl and MeOH by volume) was stirred at room temperature for 39 h. Excess pyridine was removed under reduced pressure. The residue was purified by chromatography with 1:1 ether/hexanes to provide 65.6 mg (85.5% yield) of compound 7f-6 as pale yellow oil. $^1$H-NMR showed that compound 7f-6 was a 1:1.8 ratio of isomers.

Example 34

Preparation of (2,4-difluorophenyl)-(1-isobutyl-1H-indazol-5-yl)-methanone O-benzyl-oxime (7f-7)

The synthesis of compound 7f-7 having the general Formula XII is shown in FIG. 27.

Step A: Compound 5f was prepared as described in Example 27.

Step B: Compound 5f (76.9 mg, 0.244 mmol) was dissolved in 2 mL of pyridine and O-benzylhydroxylamine hydrochloride (0.195 g, 1.22 mmol) was added. The mixture was stirred at room temperature for 2 days and concentrated under reduced pressure. The residue was suspended in $CH_2Cl_2$ and the suspension was filtered through a plug of cotton and purified by chromatography with 1:4 ether/hexanes to provide 0.069 g of compound 7f-7 as a 1:4 mixture of E and Z-isomers (67.2% yield). MS (ESI+) m/z 420 (M+H) detected.

Example 35

Preparation of (2,4-difluorophenyl)-(1-isobutyl-1H-indazol-5-yl)-methanone O-(2-aminoethyl)-oxime (7f-8)

The synthesis of compound 7f-8 having the general Formula XII is shown in FIG. 27.

Step A: Compound 7f-5 was prepared as described in Example 29.

Step B: Compound 7f-5 (32.3 mg, 0.0656 mmol) was dissolved in 2 mL of 1:1 mixture of $CH_2Cl_2$: TFA and the mixture was stirred for 0.5 hours at room temperature. The entire mixture was concentrated under reduced pressure and dried under high vacuum overnight. The residue was dissolved in 5 mL of $CH_2Cl_2$ and washed with saturated $K_2CO_3$. The organic layer was dried over $MgSO_4$, filtered through Celite, and concentrated under reduced pressure to provide 18.6 mg of compound 7f-8 as an oil (76.1% yield). MS (ESI+) m/z 373 (M+H) detected.

Example 36

Preparation of (4-fluorophenyl)-(1-isobutyl-1H-indazol-5-yl)-methanone O-methyl-oxime (7f-9)

The synthesis of compound 7f-9 having the general Formula XII is shown in FIG. 27.

Step A: Compound 5f-2 was prepared as described in Example 31.

Step B: Compound 5f-2 was dissolved ethyl)-carbamic acid tert-butyl ester (120 mg, 0.675 mmol), pyridine (1.5 mL), and one drop in 2 mL of pyridine and $MeONH_2$—HCl was added. The mixture was stirred at room temperature for 2 days and concentrated under reduced pressure. The residue was suspended in $CH_2Cl_2$ and the suspension was filtered through a plug of cotton and purified by chromatography with 1:4 ether/hexanes to provide 33.5 mg of fraction 1, 1.0 mg of fraction 2, and 17.7 mg of a mixed fraction, totaling 52.2 mg of compound 7f-9 (58% yield). MS (ESI+) m/z 344 (M+H) detected.

Example 37

Preparation of (4-fluorophenyl)-(1-isobutyl-1H-indazol-5-yl)-methanone O-(2-aminoethyl)-oxime (7f-10)

The synthesis of compound 7f-10 having the general Formula XII is shown in FIG. 27.

Step A: Compound 7f-6 was prepared as described in Example 33.

Step B: Compound 7f-6 (50.5 mg, 0.107 mmol) was dissolved in 4 mL of $CH_2Cl_2$ and trifluoroacetic acid (4 mL) was added to the solution. After 0.5 hours at room temperature, the mixture was concentrated under reduced pressure and dried under high vacuum overnight. The oil was dissolved in 10 mL of $CH_2Cl_2$ and washed with saturated $K_2CO_3$ solution. The organic layer was dried over anhydrous $MgSO_4$, filtered through Celite, and concentrated under reduced pressure to provide 34.9 mg of compound 7f-10 as an oil comprising a 1:2 mixture of isomers (88.6% yield). MS (ESI+) m/z 355 (M+H) detected.

Example 38

Preparation of 2,4-difluoro-phenyl)-(1-methyl-1H-indazol-5-yl)-methanone O-methyl-oxime (7f-11)

The synthesis of compound 7f-11 having the general Formula XII is shown in FIG. 27.

Step A: Compound 9f-1 was prepared as described in Example 74.

Step B: Compound 9f-1 (622 mg, 2.409 mmol), $K_2CO_3$ (499 mg, 1.50 equivalents), and DMF (10 mL) were placed in a Schlenk tube. Iodomethane (225 μL, 1.50 equivalents) was added and the tube was sealed. The tube was heated to 100° C. After 23 hours at 100° C., the mixture was cooled to room temperature and unsealed. The mixture was transferred to round bottomed flask and concentrated under reduced pressure. The residue was quenched with water and $CH_2Cl_2$ and layers were separated. The aqueous layer was extracted with $CH_2Cl_2$. The combined organic extracts were dried over $MgSO_4$, filtered through Celite, and concentrated under reduced pressure. The residue was purified by chromatography with 1:1 ether/hexanes to provide 176 mg of compound 5f-13 as a yellow solid (26.9% yield). MS (ESI+) m/z 273 (M+H) detected.

Step C: Compound 5f-13 (0.040 g, 0.147 mmol) and methoxylamine HCl salt (0.123 g, 1.47 mmol) were placed in a 5 mL reaction vial and 1 mL of pyridine was added. The reaction vial was sealed and heated to 50° C. After 18 hr excess pyridine was removed under reduced pressure and water was added to the residue. The aqueous mixture was extracted with $CH_2Cl_2$. The combined extracts were washed with 1 N HCl and saturated $NaHCO_3$, dried over $MgSO_4$, filtered through Celite, and concentrated under reduced pressure. The residue was purified by chromatography with 1:1 ether/hexanes to provide 0.033 g of compound 7f-11 (74.6% yield) as a viscous oil comprising a 1:9 mixture of isomers. MS (ESI+) m/z 302 (M+H) detected.

Example 39

Preparation of (2,4-difluoro-phenyl)-[1-(2,2,2-trifluoro-ethyl)-1H-indazol-5-yl]-methanone oxime (7f-12)

The synthesis of compound 7f-12 having the general Formula XII is shown in FIG. 27.

Step A: Compound 5f-11 was prepared as described in Example 74.

Step B: Compound 5f-11, hydroxylamine-HCl (0.051 g 0.735 mmol), and 1 mL of pyridine was placed in a vial and the mixture was heated to 50° C. After 14.5 hr pyridine was removed under reduced pressure and the residue was diluted with $CH_2Cl_2$ and water. The layers were separated and the aqueous layer was extracted with $CH_2Cl_2$. The combined extracts were washed with 1 N HCl and saturated $NaHCO_3$, dried over anhydrous $MgSO_4$, filtered through Celite, and concentrated under reduced pressure. The residue was purified by chromatography with 1:1 ether/hexanes to provide 22.9 mg (87.7% yield) of compound 7f-12 as a white foam comprising a 1:4 mixture of isomers. MS (ESI+) m/z 356 (M+H) detected.

Example 40

Preparation of (2,4-difluorophenyl)-[1-(2,2,2-trifluoro-ethyl)-1H-indazol-5-yl]-methanone O-methyl-oxime (7f-13)

The synthesis of compound 7f-13 having the general Formula XII is shown in FIG. 27.

Step A: Compound 5f-11 was prepared as described in Example 74.

Step B: Compound 5f-11 (0.023 g, 0.067 mmol), hydroxylamine-HCl (0.056 g, 0.676 mmol), and 1 mL of pyridine were placed in a vial and the mixture was heated to 50° C. After 14.5 hr pyridine was removed under reduced pressure and the residue was diluted with $CH_2Cl_2$ and water. The layers were separated and the aqueous layer was extracted with $CH_2Cl_2$. The combined extracts were washed with 1 N HCl and saturated $NaHCO_3$, dried over anhydrous $MgSO_4$, filtered through Celite, and concentrated under reduced pressure. The residue was purified by chromatography with 1:1 ether/hexanes to provide 19.6 mg of compound 7f-13 (78.5% yield) as a white foam comprising a 1:4 mixture of isomers. MS (ESI+) m/z 370 (M+H) detected.

Example 41

Preparation of (2,4-difluoro-phenyl)-(1-methanesulfonyl-1H-indazol-5-yl)methanone oxime (7f-14)

The synthesis of compound 7f-14 having the general Formula XII is shown in FIG. 27.

Step A: Compound 9f-1 was prepared as described in Example 13.

Step B: Compound 9f-1 (258 mg, 1.00 mmol) was dissolved in 5 mL of pyridine and methanesulfonyl chloride (81 μL, 1.05 mmol) was added. After 15 hr excess pyridine was removed under reduced pressure and water was added to the residue. The aqueous mixture was extracted with $CH_2Cl_2$. The combined extracts were washed with 1 N HCl and saturated $NaHCO_3$, dried over $MgSO_4$, filtered through Celite, and concentrated under reduced pressure. The residue was purified by chromatography with 1:1 ether/hexanes to provide 238.1 mg of compound 5f-14 as a white solid (70.8% overall yield). $^1H$ NMR (400 MHz, $CDCl_3$) δ 8.38 (s, 1H), 8.23 (s, 1H), 8.18 (d, 1H), 8.07 (d, 1H), 7.66 (q, 1H), 7.06 (t, 1H), 6.95 (t, 1H), 3.36 (s, 3H).

Step C: Compound 5f-14 (0.060 g, 0.177 mmol), hydroxylamine-HCl (0.123 g, 1.77 mmol), and 1 mL of pyridine was place in a vial and the mixture was heated to 50° C. After 26 hr excess pyridine was removed under reduced pressure and the residue was diluted with $CH_2Cl_2$ and water. The layers were separated and the aqueous layer was extracted with $CH_2Cl_2$. The combined extracts were washed with 1 N HCl and saturated $NaHCO_3$, dried over anhydrous $MgSO_4$, filtered through Celite, and concentrated under reduced pressure. The residue was purified by chromatography with 2:1 ether/hexanes. The compound was dissolved in MeOH—$CH_2Cl_2$ mixture and loaded to the column yielding 37.4 mg (60.0% yield) of compound 7f-14 as a white powder comprising a 1:2 mixture of isomers. MS (ESI+) m/z 352 (M+H) detected.

Example 42

Preparation of (2,4-difluoro-phenyl)-(1-methanesulfonyl-1H-indazol-5-yl)-methanone O-methyl-oxime (7f-15)

The synthesis of compound 7f-15 having the general Formula XII is shown in FIG. 27.

Step A: Compound 5f-14 was prepared as described in Example 41.

Step B: Compound 5f-14 (0.060 g, 0.250 mmol), methoxylamine-HCl, (0.209 g, 2.50 mmol), and 1 mL of pyridine were placed in a vial and the mixture was heated to 50° C. After 26.5 hr excess pyridine was removed under reduced pressure and the residue was diluted with $CH_2Cl_2$ and water. The layers were separated and the aqueous layer was extracted with $CH_2Cl_2$. The combined extracts were washed with 1 N HCl and saturated $NaHCO_3$, dried over anhydrous $MgSO_4$, filtered through Celite, and concentrated under reduced pressure. The residue was purified by chromatography with 1:1 ether/hexanes to provide compound 44.8 mg of 7f-15 as a white solid comprising a 1:4 mixture of isomers (49% yield). MS (ESI+) m/z 366 (M+H) detected.

Example 43

Preparation of (2,4-difluoro-phenyl)-(1H-indazol-5-yl)-methanone O-methyl-oxime (7f-16)

The synthesis of compound 7f-16 having the general Formula XII is shown in FIG. 27.

Step A: Compound 9f-1 was prepared as described in Example 13.

Step B: Compound 9f-1 and methoxylamine HCl salt were placed in a 5 mL reaction vial and 1 mL of pyridine was added. The reaction vial was sealed and heated to 50° C. After 18 hours, excess pyridine was removed under reduced pressure and water (10 mL) was added to the residue. The aqueous mixture was extracted with $CH_2Cl_2$. The combined extracts were washed with 1 N HCl (20 mL) and saturated $NaHCO_3$ (20 mL), dried over $MgSO_4$, filtered through Celite, and concentrated under reduced pressure. The residue was purified by chromatography with 1:1 ether/hexanes to provide 33.0 mg (74.6% yield) of compound 7f-16 as a viscous oil comprising a 1:4 mixture of isomers. MS (ESI+) m/z 288 (M+H) detected.

Example 44

Preparation of (1-allyl-1H-indazol-5-yl)-(2,4-difluoro-phenyl)-methanone oxime (7f-17)

The synthesis of compound 7f-17 having the general Formula XII is shown in FIG. 27.

Step A: Compound 9f-1 was prepared as described in Example 13.

Step B: Compound 9f-1 (0.516 g, 2.00 mmol), $K_2CO_3$ (0.0415 g, 3.00 mmol), DMF (10 mL), and allyl bromide (0.363, 3.00 mmol were added to a Schlenk type tube. The tube was sealed and heated to 100° C. After 19 hr the supernatant solution was decanted and salt was washed with DMF (5 mL×3). The combined supernatant solution was concentrated under reduced pressure. The residue was dissolved in $CH_2Cl_2$ and washed with water. The aqueous layer was extracted with $CH_2Cl_2$. The combined extracts were dried over anhydrous $MgSO_4$, filtered through Celite, and concentrated under reduced pressure. The residue was purified by chromatography with 1:1 ether/hexanes to provide 142.1 mg (23.8% yield) of compound 5f-12. MS (ESI+) m/z 299 (M+H) detected.

Step C: Compound 5f-12 (0.027 g, 0.090 mmol), hydroxylamine-HCl (0.063 g, 0.90 mmol), and pyridine (1 mL) were placed in a reaction vial and the mixture was heated to 50° C. After 21.5 hr the reaction was transferred to a separatory funnel and water (10 mL) was added. The mixture was extracted with $CH_2Cl_2$. The combined extracts were washed with 1 N HCl (20 mL) and saturated $NaHCO_3$, dried over $MgSO_4$, filtered through Celite, and concentrated under reduced pressure. The residue was purified by chromatography with 1:1 ether/hexanes to provide 23.1 mg (81.6% yield) of compound 7f-17 as a foamy solid comprising a 1:3 mixture of isomers. MS (ESI+) m/z 356 (M+H) detected.

Example 45

Preparation of (1-allyl-1H-indazol-5-yl)-(2,4-difluoro-phenyl)-methanone O-methyl-oxime (7f-18)

The synthesis of compound 7f-18 having the general Formula XII is shown in FIG. 27.

Step A: Compound 5f-12 was prepared as described in Example 44.

Step B: Compound 5f-12 (0.027 g, 0.090 mmol), methoxylamine-HCl (0.063 g, 0.90 mmol), and pyridine (1 mL) were placed in a reaction vial and the mixture was heated to 50° C. After 21.5 hr the reaction mixture was transferred to a separatory funnel and water (10 mL) was added. The mixture was extracted with $CH_2Cl_2$. The combined extracts were washed with 1 N HCl and saturated $NaHCO_3$, dried over $MgSO_4$, filtered through Celite, and concentrated under reduced pressure. The residue was purified by chromatography with 1:1 ether/hexanes to provide 24.7 mg (83.1% yield) of compound 7f-18 as an oil comprising a 1:3 mixture of isomers. MS (ESI+) m/z 328 (M+H) detected.

Examples 46–61 describe the synthesis of amide compound of this invention having the generic Formula XIII. FIGS. 30A–30C show the reaction scheme for the synthesis compounds having the generic structure 11g.

Example 46

Preparation of 5-(4-fluorophenoxy)-1-isobutyl-1H-indazole-6-carboxylic acid amide (11g-1)

Step A: 1-Fluoro-3-methyl-benzene (compound 1g; 18.7 g, 170 mmol) was added to a three neck 500 mL flask and cooled to −78° C. Next, solution of potassium t-butoxide (11.0 g, 170 mmol) in THF was added slowly by syringe. After 10 minutes, t-BuLi (19.0 g, 170 mmol) in pentane was added slowly by cannula under nitrogen to the reaction. After 2.5 hours of stirring, the reaction was quenched with large amount of crushed fresh dry ice, taken off the −78° C. bath and manually stirred with a metal spatula to turn the dark brown material into a much lighter yellow slurry. After 20 minutes of mixing by hand, about 500 mL of water were added and reaction mixture was stirred. The reaction mixture was then washed With $Et_2O$ and then acidified with 6 N HCl to pH less than 3 and extracted with $Et_2O$. The organic was washed with brine, dried over $MgSO_4$ filtered and concentrated to yield 10 gm (45% yield) of compound 2g. $^1$H NMR (400 MHz, $CDCl_3$) δ 7.90 (t, 1H), 7.04 (d, 1H), 6.97 (d, 1H), 2.39 (s, 3H).

Step B: Compound 2g (8.0 g, 52 mmol) was added to a 500 mL flask and cooled to salt water ice bath temp. $H_2SO_4$ (150 mL) was added and the mixture stirred. Next, a mixture of freshly prepared $H_2SO_4$ (6.11 g, 62.3 mmol) and $HNO_3$ (5.2 g, 83 mmol) was dripped into the reaction mixture over 10 minutes. After 3 hours at 0° C., the reaction was complete and was added to 1500 ml of ice/ice water and stirred for 1 hour. The reaction was filtered and rinsed several times with cold water and dried under high vacuum, yielding 8 g (80% yield) of compound 3g. $^1$H NMR (400 MHz, $CDCl_3$) δ 8.74 (d, 1H), 7.20 (d, 1H), 2.69 (s, 3H).

Step C: Compound 3g (8 g, 40.0 mmol) was dissolved in MeOH and $H_2SO_4$ (20.0 g, 201 mmol) was slowly added. The reaction was heated to 65° C. for 20 hours. The reaction was concentrated, diluted with ice and water, sonicated, filtered, rinsed several times with cold water and dried on high vacuum for 2 days. The crude was material, compound 4g, was used directly in the next step. $^1$H NMR (400 MHz, $CDCl_3$) δ 8.66 (d, 1H), 7.01 (d, 1H), 3.95 (s, 3H), 2.68 (s, 3H).

Step D: Compound 4g (5.4 g, 41 mmol) was added to THF and cooled to 0° C. To this was added 4-fluorophenol (5.1 g, 45 mmol). Next, NaH (60% in oils) (1.8 g, 45 mmol) was added in portions. After 1 hour, the reaction warmed to room temperature and stirred for 2 more hours. The reaction was concentrated and quenched with a large excess of 0.5 N $Na_2CO_3$ to pH 7.0. The reaction was sonicated for 30 minutes, filtered, and rinsed with more buffer and $H_2O$. The reaction was dried on high vacuum for 1 hour, then added to THF and $MgSO_4$ to dry, was filtered and evaporated to yield approximately 8 g (75% yield) of compound 5g. $^1$H NMR (400 MHz, DMSO-d6) δ 8.66 (d, 1H), 7.01 (d, 1H), 3.95 (s, 3H), 2.68 (s, 3H).

Step E: Compound 5g (10.0 g, 33.0 mmol) and zinc (11.0 g, 164 mmol) were added to methanol and stirred. Acetic acid (4.0 g, 66 mmol) was slowly added. The reaction was stirred overnight, sonicated and passed through Celite. Solution was concentrated to yield approximately 14 g of compound 6g and zinc by-products. The crude material was taken on to the next step.

Step F: Compound 6g (9.0 g, 33.0 mmol), ammonium tetrafluoroborate (6.0 g, 65 mmol), and HCl (17.0 g, 163 mmol), were added to 200 mL of $AcOH/H_2O$ (2:1) and sonicated. The material was scraped off the sides of round bottom and $NaNO_2$ (2.7 g, 3 mmol) was added. The reaction was sonicated for 10 minutes turning dark brown while the appearance of a new precipitate formed (product salt). The reaction was allowed to stir for 4 hours. The reaction was concentrated on a speed vacuum at 65° C., then taken up in toluene and evaporated to dryness. The crude material, compound 7g, was taken directly on to the next step without any workup.

Step G: Compound 7g (11.0 g, 31 mmol), potassium acetate (5.2 g, 53 mmol) and 18-crown-6 (0.1 equivalents) were added to chloroform and sonicated for 10 minutes. The reaction ran overnight at room temperature. A column was packed in a 1000 mL filter flask consisting of approximately 2 inches of silica gel, 2 inches of Celite layered on top or the silica gel, a sheet of filter paper on top of the Celite, and one half inch of sand on top of the filter paper. The column was washed with $CHCl_3$. The crude material was loaded onto the column directly in $CHCl_3$, and the column was eluted with $CHCl_3$ until a large amount of yellow material came off. Next, the product was eluted from the column with ethyl acetate and the ethyl acetate collections were pooled and concentrated to give around 7 g (95% yield) of compound 8g. MS (ESI+) m/z 287 (M+H) detected.

Step H: Compound 8g (0.250 g, 0.87 mmol), was added to dry DMF, and to this was added isobutyl bromide (0.15 ml, 1.2 mmol), and $K_2CO_3$ (0.5 g, 3.6 mmol). This reaction mixture was then placed in a septum covered vial and stirred at 95° C. overnight. The material was purified by column chromatography with 1:1 diethyl ether/hexanes to provide 0.1 g (33% yield) of compound 9g-1. MS (ESI+) m/z 343 (M+H) detected.

Step I: Compound 9g-1 (0.100 g, 0.292 mmol) was placed in a 1:1 mixture of 1 N LiOH/THF and stirred at 55° C. After 4 hours, the THF was evaporated and 1 N HCl was added. The reaction mixture was sonicated and filtered to isolate around 0.075 g (78% yield) of compound 10g as a pure material. MS (ESI+) m/z 329 (M+H) detected.

Step J: A solution of compound 10g (20 mg, 0.061 mmol) in THF (1 ml) was treated with CDI (1.2 equivalents) at room temperature under nitrogen atmosphere. After stirring for 18 hours, the reaction was treated with 0.5 M $NH_4$ in dioxane (0.11 ml, 0.67 mmol). After an additional 18 hours, the solvent was allowed to slowly evaporate and the mixture was purified in a Sep Pak cartridge eluting with $CH_2Cl_2$—5% $MeOH/CH_2Cl_2$ to provide 2.2 mg of compound 11g-1 as an oil in 12% yield. $^1$H NMR (400 MHz, DMSO-d6) δ 8.01 (s, 1H), 7.99 (s, 1H), 7.73 (s, 1H), 7.57 (s, 1H), 7.26 (s, 1H), 7.20 (m, 2H), 7.05 (m, 2H), 4.27 (d, 2H), 2.24 (m, 1H), 0.86 (d, 6H).

Example 47

Preparation of [5-(4-fluorophenoxy)-1-isobutyl-1H-indazol-6-yl]-morpholin-4-yl-methanone (11g-2)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with morpholine (1 equivalent). After an additional 18 hours, the solvent was allowed to slowly evaporate and the residue was purified in a Sep Pak cartridge eluting with a gradient of 100% $CH_2Cl_2$ to $MeOH/CH_2Cl_2$ to provide compound 11g-2 as an oil in 93% yield.

Example 48

Preparation of [5-(4-fluorophenoxy)-1-isobutyl-1H-indazol-6-yl]-(4-methylpiperazin-1-yl)-methanone (11g-3)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 1-methyl-piperazine (1 equivalent). After an additional 18 hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-3 as an oil in 95% yield.

Example 49

Preparation of 5-(4-fluorophenoxy)-1-isobutyl-1H-indazole-6-carboxylic acid (1-benzylpiperidin-4-yl)-amide (11g-4)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 1-benzyl-piperidin-4-yl-amine (1 equivalent). After an additional 18 hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-4 as an oil in 97% yield.

Example 50

Preparation of 5-(4-fluorophenoxy)-1-isobutyl-1H-indazole-6-carboxylic acid (2-benzylaminoethyl)-amide (11g-5)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring at for 18 hours, the reaction was treated with N1-benzyl-ethane-1,2-diamine (1 equivalent). After an additional 18 hours, the solvent was allowed to slowly evaporate and the residue was purified in a Sep Pak cartridge eluting with a gradient of 100% $CH_2Cl_2$ to MeOH/$CH_2Cl_2$ to provide compound 11g-5 as an oil in 100% yield.

Example 51

Preparation of 5-(4-fluorophenoxy)-1-isobutyl-1H-indazole-6-carboxylic acid (2-piperidin-yl-ethyl)-amide (11g-6)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 2-piperidin-1-yl-ethylamine (1 equivalent). After an additional 18 hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-6 as an oil in 100% yield.

Example 52

Preparation of 5-(4-fluorophenoxy)-1-isobutyl-1H-indazole-6-carboxylic acid (2-pyrrolidin-1-yl-ethyl)-amide (11g-7)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 2-pyrrolidin-1-yl-ethylamine (1 equivalent). After an additional 18 hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-7 as an oil in 63% yield.

Example 53

Preparation of 5-(4-fluorophenoxy)-1-isobutyl-1H-indazole-6-carboxylic acid (3-morpholin-4-yl-propyl)-amide (11g-8)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 3-morpholin-4-yl-propylamine (1 equivalent). After an additional 18 hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-8 as an oil in 70% yield.

Example 54

Preparation of 5-(4-fluorophenoxy)-1-isobutyl-1H-indazole-6-carboxylic acid (3-dimethylaminopropyl)-amide (11g-9)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with N-1-dimethyl-propane-1,3-diamine (1 equivalent). After 18 additional hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-9 as an oil in 44% yield.

Example 55

Preparation of 5-(4-fluorophenoxy)-1-isobutyl-1H-indazole-6-carboxylic acid (2-dimethylaminoethyl)-amide (11g-10)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with N1-dimethyl-ethane-1,2-diamine; 1 equivalent). After 18 additional hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-10 as an oil in 58% yield.

Example 56

Preparation of 5-(4-fluorophenoxy)-1-isobutyl-1H-indazole-6-carboxylic acid methyl-(1-methylpiperidin-4-yl)-amide (11g-11)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with methyl-(1-methyl-piperidin-4-yl)-amine (1 equivalent). After 18 additional hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-11 as an oil in 3% yield.

Example 57

Preparation of 5-(4-fluorophenoxy)-1-isobutyl-1H-indazole-6-carboxylic acid [3-(methylphenylamino)-propyl]-amide (11g-12)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with N1-Methyl-N1-phenyl-propane-1,3-diamine (1 equivalent). After 18 additional hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-12 as an oil in 78% yield.

Example 58

Preparation of 3-{[5-(4-fluorophenoxy)-1-isobutyl-1H-indazole-6-carbonyl]-amino}-pyrrolidine-1-carboxylic acid tert-butyl ester (11g-13)

A solution of 5-(4-fluorophenoxy)-1-isobutyl-1H-indazole-6-carboxylic acid (compound 10g, prepared as described in Example 46) in THF was treated with carbonyldiimidazole (1.2 equivalents) at room temperature under nitrogen atmosphere. After stirring for 18 hours, the reaction was treated with 3-amino-pyrrolidine-1-carboxylic acid tert-butyl ester (1 equivalent). After 18 additional hours, the solvent was allowed to slowly evaporate and the residue was purified in a Sep Pak cartridge eluting with a gradient of 100% $CH_2Cl_2$ to 5% MeOH/$CH_2Cl_2$ to provide compound 11g-13 as an oil in 94% yield.

Example 59

Preparation of 5-(4-fluorophenoxy)-1-(2,2,2-trifluoroethyl)-1H-indazole-6-carboxylic acid (2-dimethylaminoethyl)amide (11g-14)

Step A: Compound 8g was prepared as described in Example 46.

Step B: Compound 8g, 2-bromo-1,1,1-trifluoro-ethane and $K_2CO_3$ and DMF were combined and the reaction mixture was stirred overnight at 75° C. Two additional equivalents of 2-bromo-1,1,1-trifluoroethane were added and the reaction stirred at 90° C. Several additional equivalents of 2-bromo-1,1,1-trifluoroethane were added and the reaction stirred at 50° C. for 72 hr. The reaction was concentrated, taken up in toluene, and purified by column chromatography (eluted with hexane/$Et_2O$), yielding 80 mg (24% yield) of compound 9g-2. MS (ESI+) m/z 369 (M+H) detected.

Step C: Compound 9g-2 (0.075 g, 0.20 mmol) was placed in a 1:1 mixture of 1 N LiOH/THF and stirred for 18 hours at room temperature. The THF was evaporated and 1 N HCl was added to the reaction mixture, which was then sonicated and filtered to isolate approximately 0.070 g (97% yield) of compound 10g-2 as pure material. MS (ESI+) m/z 355 (M+H) detected.

Step D: Compound 10g-2 (0.03 g, 0.847 mmol), benzotriazole-1,3-diol (0.022 g, 0.25 mmol) and (3-dimethylaminopropyl)-ethylcarbodiimide (0.011 g, 0.10 mmol) were added to dichloroethane and stirred for 5 minutes. Next, $N^1$-dimethyl-ethane-1,2-diamine (0.019 g, 0.10 mmol) was added and the reaction stirred for 3 hours. The reaction mixture was concentrated, taken up in dicloromethane, dried under high vacuum and purified by reverse phase HPLC according to method C (see below), yielding 25 mg (56% yield) of compound 11g-14 as the TFA salt. $^1$H NMR (400 MHz, $CDCl_3$) δ 8.45 (s, 1H), 8.10 (s, 1H), 7.90 (s, 1H), 7.12 (m, 4H), 5.02 (q, 2H), 3.93 (br, 2H), 3.34 (br, 6H), 2.72 (s, 6H).

Example 60

Preparation of 5-(4-fluorophenoxy)-1-methyl-1H-indazole-6-carboxylic acid (2-dimethylaminoethyl) amide (11g-15)

Step A: Compound 8g was prepared as described in Example 46.

Step B: Compound 8g, iodomethane and $K_2CO_3$ were added to DMF and heated to about 75° C. After 48 hours the reaction was filtered to remove the $K_2CO_3$, concentrated, taken up in toluene and purified by column chromatography (eluting with 1:1 $Et_2O$/hexane), yielding 70 mg (36.7% yield) of compound 9g-3. MS (ESI+) m/z 301 (M+H) detected.

Step C: Compound 9g-3 (0.075 g, 0.25 mmol) was placed in a 1:1 mixture of 1 N LiOH/THF and stirred for 18 hours at room temperature. The THF was evaporated and 1 N HCl was added to the reaction mixture, which was then sonicated and filtered to provide approximately 0.060 g (84% yield) of compound 10g-3 as pure material. MS (ESI+) m/z 287 (M+H) detected.

Step D: Compound 10g-3 (0.030 g, 0.105 mmol), benzotriazole-1,3-diol (0.028 g, 0.31 mmol) and (3-dimethylamino-propyl)-ethyl-carbodiimide (0.019 g, 0.13 mmol) were added to dichloroethane and stirred for 5 minutes. Next, $N^1$-dimethyl-ethane-1,2-diamine (0.024 g, 0.13 mmol) was added and the reaction stirred for 3 hours. The reaction mixture was then concentrated, taken up in dichloroethane, dried under high vacuum and purified by reversed phase HPLC according to Method C of Example 86, yielding 25 mg (52% yield) of compound 11g-15 as the TFA salt. $^1$H NMR (400 MHz, $CDCl_3$) δ 8.44 (br, 1H), 8.21 (s, 1H), 7.85 (s, 1H), 7.05 (m, 4H), 4.15 (s, 3H), 3.90 (br, 2H), 3.30 (br, 2H), 2.92 (s, 6H).

Example 61

Preparation of 5-(4-fluorophenoxy)-1H-indazole-6-carboxylic acid (2-dimethylaminoethyl)amide (11g-16)

Step A: Compound 8g was prepared as described in Example 46.

Step B: Compound 8g was stirred in THF, one volume equivalent of 1 N LiOH was added and the reaction stirred at 60° C. for 6 hours. The reaction was concentrated, quenched with 1 N HCl, cooled, sonicated, filtered and dried to give 0.40 g of compound 10g-4 (84% pure material). MS (ESI+) m/z 287 (M+H) detected.

Step C: Compound 10g-4 (0.030 g, 0.110 mmol), benzotriazole-1,3-diol (0.029 g, 0.33 mmol) and (3-dimethylaminopropyl)-ethylcarbodiimide (0.020 g, 0.13 mmol) were added to dichloroethane and stirred for 5 minutes. Next, $N^1$-dimethylethane-1,2-diamine (0.025 g, 0.13 mmol) was added and the reaction stirred for 3 hours. The reaction was evaporated, taken up in dichloroethane and dried under high vacuum and purified by reversed phase HPLC according to Method B of Example 86, to provide 25 mg (51% yield) of compound 11g-16 as the TFA salt. $^1$H NMR (400 MHz, CDCl$_3$) δ 8.45 (br, 1H), 8.22 (s, 1H), 7.91 (s, 1H), 7.09 (s, 1H), 7.06 (m, 3H), 3.85 (br, 2H), 3.20 (br, 2H), 2.90 (s, 6H).

Examples 62–67 describe the synthesis of alcohol compounds having the general Formula IX. FIG. 30 shows a synthetic reaction scheme for the synthesis of generic compound 4f.

Example 62

Preparation of (2,4-difluorophenyl)-(1-isobutyl-1H-indazol-5-yl)-methanol (4f-1)

In this example, the synthesis of compound 4f-1 as shown in FIG. 30, where $R^1$ is isobutyl and Ar is 2,4-difluorophenyl is described.

Step A: Ammonium tetrafluoroborate (20.97 g, 200 mmol) was dissolved in aqueous acetic acid (500 mL AcOH/250 mL water) and cooled to 0° C. 2-Methyl-4-bromoaniline (compound 1f, 18.61 g, 100 mmol) and 42 mL of aqueous concentrated HCl (36% w/w, 12N, 500 mmol) were sequentially added. The mixture was stirred for 20 minutes at 0° C. and NaNO$_2$ (7.59 g, 110 mmol) was added. The reaction was stirred for 1 hour at 0° C. and warmed to room temperature. After 16 hours at room temperature, the mixture was concentrated under reduced pressure and the residue was azeotroped with toluene and dried under high vacuum. The solid was suspended in 500 mL of CHCl$_3$ and KOAc (12.76 g, 130 mmol) and 18-crown-6 (7.93 g, 30 mmol) were added. The reaction was stirred for 1.5 hours at room temperature. The mixture was washed with water, dried over anhydrous MgSO$_4$, filtered through Celite and concentrated under reduced pressure to provide 30 g of 5-bromo-1H-indazole (compound 2f) as a tan solid. The crude material was used without further purification.

Step B: The crude 5-bromo-1H-indazole (compound 2f; 100 mmol) was dissolved in 250 mL of DMF. K$_2$CO$_3$ (20.7 g, 150 mmol) and 1-bromo-2-methylpropane (16.3 mL, 150 mmol) were added. The mixture was heated to 120° C. under nitrogen atmosphere for 16 hours. The mixture was cooled to room temperature and concentrated under reduced pressure. Water (200 mL) and CH$_2$Cl$_2$ (200 mL) were added to the residue and stirred vigorously for 30 minutes. The layers were separated and the aqueous layer was extracted with CH$_2$Cl$_2$. The combined extracts were dried over anhydrous MgSO$_4$, filtered through Celite, and concentrated under reduced pressure to provide about 30 g of crude material. The crude material was purified by chromatography (1:9 to 1:4 ether/hexanes) to provide 12.870 g of compound 3f as a dark red oil, yielding 50.8% for steps A and B. MS ESI (+) m/z 253 and 255 (M+1) detected. $^1$H-NMR (400 MHz, CDCl$_3$) δ 7.93 (s, 1H), 7.87 (m, 1H), 7.43 (m, 1H), 7.29 (m, 1H), 7.29 (m, 1H), 4.15 (m, 2H), 2.33 (m, 1H), 0.92 (m, 6H).

Step C: Compound 3f (121.0 mg, 0.478 mmol) was dissolved in 2 mL of ether and cooled to −78° C. To the solution was added t-BuLi (1.70 M in pentane, 0.59 mL, 1.004 mmol). The reaction stirred an additional hour at −78° C. 2,6-Difluorobenzaldehyde (58 μL, 0.526 mmol) was added at −78° C., the cold bath was removed and the reaction slowly warmed to room temperature. The reaction was quenched with 10 mL of water. The layers were separated and the aqueous layer was extracted with CH$_2$Cl$_2$. The combined extracts were dried over anhydrous MgSO$_4$, filtered through Celite, concentrated under reduced pressure, and purified by chromatography with 1:1 ether/hexanes to provide 104.5 mg (69.1% yield) compound 4f-1 as a pale yellow crystalline solid. MS ESI (+) m/z 317 (M+1) detected. $^1$H-NMR (400 MHz, CDCl$_3$) δ 7.96 (s, 1H), 7.73 (s, 1H), 7.56 (m, 1H), 7.40~7.35 (m, 2H), 6.91 (m, 2H), 6.78 (m, 1H), 6.22 (m, 1H), 4.15 (m, 2H), 2.39~2.26 (m, 2H, overlapped with —OH), 0.92 (m, 6H).

Example 63

Preparation of (4-chloro-2-fluoro-phenyl)-(1-isobutyl-1H-indazol-5-yl)-methanol (4f-7)

In this example, the synthesis of compound 4f-7 as shown in FIG. 30, where $R^1$ is isobutyl and Ar is 4-chloro-2-fluorophenyl is described.

Steps A–B: 5-Bromo-1-isobutyl-1H-indazole (compound 3f) was prepared as described in Example 1, steps A–B.

Step B: Compound 3f (132 mg, 0.521 mmol) in 1 mL of ether was cooled to −78° C. To the solution was added t-BuLi (1.70 M in pentane, 0.64 mL, 1.10 mmol). After 1 hour at −78° C., a solution 4-chloro-2-fluorobenzaldehyde (86.8 mg, 0.548 mmol) in 1 mL of ether was added and the mixture was slowly warmed to room temperature. The mixture was quenched with water (5 mL) and layers were separated. The aqueous layer was extracted with CH$_2$Cl$_2$ and the combined extracts were dried over anhydrous MgSO$_4$, filtered through Celite, and concentrated under reduced pressure. The crude was purified by chromatography with 1:2 ether/hexanes to provide 43.7 mg of compound 4f-7 as a pale yellow solid (25.2% yield). MS ESI (+) m/z 333 and 335 (M+1) detected. $^1$H-NMR (400 MHz, CDCl$_3$) δ 7.96 (s, 1H), 7.72 (s, 1H), 7.56 (m, 1H), 7.39~7.35 (m, 2H), 7.18 (m, 1H), 7.05 (m, 1H), 6.21 (m, 1H), 4.15 (m, 2H), 2.37~2.27 (m, 2H, overlapped with —OH), 0.91 (m, 6H).

Example 64

Preparation of (2-chloro4-fluoro-phenyl)-(1-isobutyl-1H-indazol-5-yl)-methanol (4f-8)

In this example, the synthesis of compound 4f-8 as shown in FIG. 30, where $R^1$ is isobutyl and Ar is 2-chloro-4-fluorophenyl is described.

Steps A–B: 5-Bromo-1-isobutyl-1H-indazole (compound 3f) was prepared as described in Example 1, steps A–B.

Step C: A solution of compound 3f (116.2 mg, 0.459 mmol) in 1 mL of ether was cooled to −78° C. To the solution was added t-BuLi (1.70 M in pentane, 0.57 mL) at −78° C. After 1 hour at −78° C., a solution 2-chloro-4-fluorobenzaldehyde (76.4 mg, 0.482 mmol) in 1 mL of ether was added and the mixture was slowly warmed to room temperature. The mixture was quenched with water (5 mL) and layers were separated. The aqueous layer was extracted with CH$_2$Cl$_2$ and the combined extracts were dried over MgSO$_4$, filtered through Celite, and concentrated under reduced pressure. The crude was purified by chromatography with 1:2 ether/hexanes to provide 47.6 mg of compound 4f-8 as a pale yellow solid (31.2% yield). MS ESI (+) m/z 333 and 335 (M+1) detected. $^1$H-NMR (400 MHz, CDCl$_3$) δ 7.96 (s, 1H), 7.72~7.66 (m, 2H), 7.39~7.34 (m, 2H), 7.13~7.03 (m, 2H), 6.29 (m, 1H), 4.15 (m, 2H), 2.38~2.27 (m, 2H, overlapped with —OH), 0.92 (m, 6H).

Example 65

Preparation of (4-fluoro-phenyl)-(1-isobutyl-1H-indazol-5-yl)-methanol (4f-2)

In this example, the synthesis of compound 4f-2 as shown in FIG. 30, where R$^1$ is isobutyl and Ar is 4-fluorophenyl is described.

Steps A–B: 5-Bromo-1-isobutyl-1H-indazole (compound 3f) was prepared as described in Example 1, steps A–B.

Step C: Compound 3f (1.49 g, 5.89 mmol) was dissolved in 50 mL of ether and the solution was cooled to −78° C. To the solution was added t-BuLi (1.70 M in pentane, 7.01 mL, 12.07 mmol) dropwise. As the t-BuLi was added, a brown solid formed and the mixture became a slurry. After the complete addition of t-BuLi, the mixture was stirred an additional 30 minutes at −78° C. 4-Fluorobenzaldehyde (700 µL, 6.475 mmol) was added dropwise at −78° C., after which the cold bath was removed and the reaction mixture was slowly warmed to room temperature. The reaction was quenched with 20 mL of water and the layers were separated. The aqueous layer was extracted with CH$_2$Cl$_2$ and the combined extracts were washed with brine (20 mL), dried over MgSO$_4$, filtered through Celite, and concentrated to provide 1.70 g of a tan solid. The solid was then purified by chromatography with 1:1 ether/hexanes to provide 1.233 g of compound 4f-2 as a light brown solid (70.2% yield). MS ESI (+) m/z 299 (M+1) detected. $^1$H-NMR (400 MHz, CDCl$_3$) δ 7.97 (s, 1H), 7.72 (s, 1H), 7.40~7.31 (m, 4H), 7.07~7.00 (m, 2H), 5.96 (m, 1H), 4.15 (m, 2H), 2.38~2.27 (m, 2H, overlapped with —OH), 0.92 (m, 6H).

Example 66

Preparation of (2,4-dichloro-phenyl)-(1-isobutyl-1H-indazol-5-yl)-methanol (4f-9)

In this example, the synthesis of compound 4f-9 as shown in FIG. 30, where R$^1$ is isobutyl and Ar is 2,4-dichlorophenyl is described.

Steps A–B: 5-Bromo-1-isobutyl-1H-indazole (compound 3f) was prepared as described in Example 1, steps A–B.

Step C: Compound 3f (106.8 mg, 0.422 mmol) was dissolved in 2 mL of ether. The solution was cooled to −78° C. and stirred for 15 minutes. t-BuLi (1.70 M in pentane, 0.52 mL, 0.886 mmol) was slowly added to the mixture. The mixture became a red slurry and was stirred an additional hour at −78° C. 2,4-Dichlorobenzaldehyde (81.2 mg, 0.464 mmol) was dissolved in 1 mL of ether and the solution was transferred to the slurry by a double ended needle. The cold bath was removed to allow the reaction warm slowly to room temperature. The reaction was quenched with 10 mL of water and the layers were separated. The aqueous layer was extracted with CH$_2$Cl$_2$. The combined extracts were dried over anhydrous MgSO$_4$, filtered through Celite, concentrated under reduced pressure, and purified by chromatography with 1:1 ether/hexanes to provide compound 4f-9 as a yellow foam (99.6 mg, 67.6% yield). MS ESI (+) m/z 349 and 351 (M+1) detected. $^1$H-NMR (400 MHz, CDCl$_3$) δ 7.96 (s, 1H), 7.70 (s, 1H), 7.68 (m, 1H), 7.38~7.36 (m, 3H), 7.33 (m, 1H), 6.27 (m, 1H), 4.15 (m, 2H), 2.39 (m, 1H, —OH), 2.37~2.26 (m, 1H), 0.92 (m, 6H).

Example 67

Preparation of (1-isobutyl-1H-indazol-5-yl)-O-tolyl methanol (4f-10)

In this example, the synthesis of compound 4f-10 as shown in FIG. 30, where R$^1$ is isobutyl and Ar is 2-methylphenyl is described.

Steps A–B: 5-Bromo-1-isobutyl-1H-indazole (compound 3f) was prepared as described in Example 1, steps A–B.

Step C: Compound 3f (123.3 mg, 0.487 mmol) was dissolved in 2 mL of ether. The solution was cooled to −78° C. and stirred for 15 minutes. t-BuLi (1.70 M in pentane, 0.62 mL, 1.023 mmol) was slowly added to the mixture. The mixture became a red slurry and was stirred an additional hour at −78° C. O-Tolualdehyde (62 µL, 0.536 mmol) was added at −78° C. and the cold bath was removed to allow the reaction warm slowly to room temperature. The reaction was quenched with 10 mL of water, the layers were separated and the aqueous layer was extracted with CH$_2$Cl$_2$. The combined extracts were dried over anhydrous MgSO$_4$, filtered through Celite, concentrated under reduced pressure, and purified by chromatography with 1:1 ether/hexanes to provide compound 4f-10 as a very viscous pale yellow oil (96.4 mg, 67.2% yield). MS ESI (+) m/z 295 (M+1) detected. $^1$H-NMR (400 MHz, CDCl$_3$) δ 7.94 (s, 1H), 7.64~7.61 (m, 2H), 7.38~7.33 (m, 2H), 7.29, (m, 1H), 7.23 (m, 1H), 7.17~7.13 (m, 1H), 6.13 (m, 1H), 4.15 (m, 2H), 2.32 (m, 1H), 2.24 (s, 3H), 2.18 (m, 1H, —OH), 0.91 (m, 6H).

Examples 68–75 describe the synthesis of compound of the general Formula X. FIG. 31 shows a synthetic reaction scheme for the synthesis of compounds having the generic structure 5f.

Example 68

Preparation of (2,4-difluorophenyl)-(1-isobutyl-1H-indazol-5-yl)-methanone (5f-1)

In this example, the synthesis of compound 5f-1 as shown in FIG. 31, where R$^1$ is isobutyl and Ar is 2,4-difluorophenyl is described.

Step A: Ammonium tetrafluoroborate (20.97 g, 200 mmol) was dissolved in aqueous acetic acid (500 mL AcOH/250 mL water) and cooled to 0° C. 2-Methyl-4-bromoaniline (18.61 g, 100 mmol) and 42 mL of aqueous concentrated HCl (36% w/w, 12N, 500 mmol) were sequentially added. The mixture was stirred for 20 minutes at 0° C. and NaNO$_2$ (7.59 g, 110 mmol) was added. The reaction was stirred for 1 hour at 0° C. and warmed to room temperature. After 16 hours at room temperature, the mixture was concentrated under reduced pressure and the residue was azeotroped with toluene and dried under high vacuum. The solid was suspended in 500 mL of CHCl$_3$ and KOAc (12.76 g, 130 mmol) and 18-crown-6 (7.93 g, 30 mmol) were added. The reaction was stirred for 1.5 hours at room temperature. The mixture was washed with water, dried over anhydrous MgSO$_4$, filtered through Celite and concentrated under reduced pressure to provide 30 g of 5-bromo-1H-indazole (compound 2f) as a tan solid. The crude material was used without further purification.

Step B: The crude 5-bromo-1H-indazole (compound 2f; 100 mmol) was dissolved in 250 mL of DMF. K$_2$CO$_3$ (20.7 g, 150 mmol) and 1-bromo-2-methylpropane (16.3 mL, 150 mmol) were added. The mixture was heated to 120° C. under nitrogen atmosphere for 16 hours. The mixture was cooled to room temperature and concentrated under reduced pressure. Water (200 mL) and CH$_2$Cl$_2$ (200 mL) were added to the residue and stirred vigorously for 30 minutes. The layers were separated and the aqueous layer was extracted with CH$_2$Cl$_2$. The combined extracts were dried over anhydrous MgSO$_4$, filtered through Celite, and concentrated under reduced pressure to provide about 30 g of crude material. The crude material was purified by chromatography (1:9 to 1:4 ether/hexanes) to provide 12.870 g of compound 3f as a dark red oil, yielding 50.8% for steps A and B. MS ESI (+) m/z 253 and 255 (M+1) detected. $^1$H-NMR (400 MHz, CDCl$_3$) δ 7.93 (s, 1H), 7.87 (m, 1H), 7.43 (m, 1H), 7.29 (m, 1H), 7.29 (m, 1H), 4.15 (m, 2H), 2.33 (m, 1H), 0.92 (m, 6H).

Step C: Compound 3f (121.0 mg, 0.478 mmol) was dissolved in 2 mL of ether and cooled to −78° C. To the solution was added t-BuLi (1.70 M in pentane, 0.59 mL, 1.004 mmol). The reaction stirred an additional hour at −78° C. 2,4-Difluorobenzaldehyde (58 μL, 0.526 mmol) was added at −78° C., the cold bath was removed and the reaction slowly warmed to room temperature. The reaction was quenched with 10 mL of water. The layers were separated and the aqueous layer was extracted with CH$_2$Cl$_2$. The combined extracts were dried over anhydrous MgSO$_4$, filtered through Celite, concentrated under reduced pressure, and purified by chromatography with 1:1 ether/hexanes to provide compound 4f-1 as a pale yellow crystalline solid (104.5 mg, 69.1% yield). MS ESI (+) m/z 317 (M+1) detected. $^1$H-NMR (400 MHz, CDCl$_3$) δ 7.96 (s, 1H), 7.73 (s, 1H), 7.56 (m, 1H), 7.40~7.35 (m, 2H), 6.91 (m, 2H), 6.78 (m, 1H), 6.22 (m, 1H), 4.15 (m, 2H), 2.39~2.26 (m, 2H, overlapped with —OH), 0.92 (m, 6H).

Step D: Compound 4f-1 (316.3 mg, 1.00 mmol), "Dess Martin Periodinane" (triacetoxyperiodinane; 445.3 mg, 1.05 mmol), and 10 mL of CH$_2$Cl$_2$ were stirred for 2 hours at room temperature. The reaction mixture was quenched with 10 mL of saturated K$_2$CO$_3$ solution and layers were separated. The aqueous layer was extracted with CH$_2$Cl$_2$. The combined extracts were dried over anhydrous MgSO$_4$, filtered through Celite, and concentrated under reduced pressure. The crude was purified by chromatography with 1:2 ether/hexanes to provide 237.6 mg of compound 5f-1 as a viscous light brown oil (75.6% yield). MS ESI (+) m/z 315 (M+1) detected. $^1$H-NMR (400 MHz, CDCl$_3$) δ 8.16 (s, 1H), 8.11 (s, 1H), 7.99 (m, 1H), 7.60 (m, 1H), 7.47 (m, 1H), 7.03 (m, 1H), 6.94 (m, 1H), 4.21 (m, 2H), 2.37 (m, 1H), 0.95 (m, 6H).

Example 69

Preparation of (4-fluorophenyl)-(1-isobutyl-1H-indazol-5-yl)-methanone (5f-2)

In this example, the synthesis of compound 5f-2 as shown in FIG. 31, where R$^1$ is isobutyl and Ar is 4-fluorophenyl is described.

Steps A–C: (4-fluorophenyl)-(1-isobutyl-1H-indazol-5-yl)-methanol (compound 4f-2) was prepared as described in Example 27, steps A–C, with the exception that 4-fluorobenzaldehyde was used in place of 2,4-difluorobenzaldehyde.

Step D: A mixture of (4-fluorophenyl)-(1-isobutyl-1H-indazol-5-yl)-methanol (compound 4f-2; 745.9 mg, 2.50 mmol), "Dess Martin Periodinane" (triacetoxyperiodinane; 1.166 g, 2.75 mmol), and 50 mL of CH$_2$Cl$_2$ was stirred at room temperature for 2 hours. The reaction was quenched with 20 mL of saturated K$_2$CO$_3$ solution. The layers were separated and the aqueous layer was extracted with CH$_2$Cl$_2$. The combined extracts were dried over anhydrous MgSO$_4$, filtered through Celite, and concentrated under reduced pressure. The residue was purified by chromatography with 1:4 ether/hexanes to provide 599 mg of compound 5f-2 as light brown solid (80.9% yield). MS ESI (+) m/z 297 (M+1) detected.

$^1$H-NMR (400 MHz, CDCl$_3$) δ 8.17 (s, 1H), 8.11 (s, 1H), 7.94 (m, 1H), 7.87 (m, 1H), 7.85 (m, 1H), 7.49 (m, 1H), 7.22~7.16 (m, 2H), 4.23 (m, 2H), 2.38 (m, 1H), 0.96 (m, 6H).

Example 70

Preparation of (2,4-dichlorophenyl)-(1-isobutyl-1H-indazol-5-yl)-methanone (5 f-9)

In this example, the synthesis of compound 5f-9 as shown in FIG. 31, where R$^1$ is isobutyl and Ar is 2,4-dichlorophenyl is described.

Steps A–C: (2,4-Dichlorophenyl)-(1-isobutyl-1H-indazol-5-yl)-methanol (compound 4f-9) was prepared as described in Example 27, steps A–C, with the exception that 2,4-dichlorobenzaldehyde was used in place of 2,4-difluorobenzaldehyde.

Step D: A mixture of compound 4f-9, "Dess Martin Periodinane" (triacetoxyperiodinane; 20 mg, 0.046 mmol), and 1 mL of CH$_2$Cl$_2$ was stirred at room temperature for 2 hours. The mixture was loaded onto a Biotage system and eluted with 1:2 ether/hexanes to provide 12.9 mg of compound 5f-9 (85% yield). MS ESI (+) m/z 347 and 349 (M+1) detected. $^1$H-NMR (400 MHz, CDCl$_3$) δ 8.09 (s, 1H), 8.06 (m, 1H), 7.53 (m, 1H), 7.47 (m, 1H), 7.41~7.34 (m, 2H), 4.21 (m, 2H), 2.36 (m, 1H), 0.95 (m, 6H).

Example 71

Preparation of (1-isobutyl-1H-indazol-5-yl)-O-tolyl-methanone (5f-10)

In this example, the synthesis of compound 5f-10 as shown in FIG. 31, where R$^1$ is isobutyl and Ar is 2-methylphenyl is described.

Steps A–C: (1-isobutyl-1H-indazol-5-yl)-O-tolyl methanol (compound 4f-10) was prepared as described in Example 27, steps A–C, with the exception that O-tolualdehyde was used in place of 2,4-difluorobenzaldehyde.

Step D: Compound 4f-10, (21 mg, 0.070 mmol), "Dess Martin Periodinane" (triacetoxyperiodinane; 31 mg, 0.0735 mmol), and 1 mL of CH$_2$Cl$_2$ was stirred at room temperature for 2 hours. The mixture was loaded onto a Biotage system and eluted with 1:2 ether/hexanes to provide 18.7 mg of compound 5f-10 (91.4% yield). MS ESI (+) m/z 293 (M+1) detected. $^1$H-NMR (400 MHz, CDCl$_3$) δ 8.07 (s, 1H), 8.06 (s, 1H), 8.04 (m, 1H), 7.46 (m, 1H), 7.41 (m, 1H), 7.35~7.30 (m, 2H), 7.30~7.25 (m, 1H), 4.21 (m, 2H), 2.36 (m, 1H), 2.33 (s, 3H), 0.95 (m, 6H).

Example 72

Preparation of (2-chloro-4-fluorophenyl)-(1-isobutyl-1H-indazol-5-yl)-methanone (5f-8)

In this example, the synthesis of compound 5f-8 as shown in FIG. 31, where R$^1$ is isobutyl and Ar is 2-chloro-4-fluorophenyl is described.

Steps A–C: (2-chloro-4-fluorophenyl)-(1-isobutyl-1H-indazol-5-yl)-methanol (compound 4f-8) was prepared as described in Example 27, steps A–C, with the exception that 2-chloro-4-fluorobenzaldehyde was used in place of 2,4-difluorobenzaldehyde.

Step D: (2-chloro-4-fluorophenyl)-(1-isobutyl-1H-indazol-5-yl)-methanol (compound 4f-8; 16.2 mg, 0.0487 mmol), "Dess Martin Periodinane" (triacetoxyperiodinane; 21.7 mg, 0.0511 mmol), and 1 mL of $CH_2Cl_2$ was stirred for 2 hrs at room temperature. The reaction was loaded onto a Biotage system and eluted with 1:2 ether/hexanes to provide 13.0 mg of compound 5f-8 as an oil (80.7% yield). MS ESI (+) m/z.

Example 73

Preparation of (4-chloro-2-fluorophenyl)-(1-isobutyl-1H-indazol-5-yl)-methanone (5 f-7)

In this example, the synthesis of compound 5f-7 as shown in FIG. 31, where $R^1$ is isobutyl and Ar is 4-chloro-2-fluorophenyl is described.

Steps A–C: (4-chloro-2-fluorophenyl-(1-isobutyl-1H-indazol-5-yl)-methanol (compound 4f-7) was prepared as described in Example 27, steps A–C, with the exception that 4-chloro-2-fluorophenylbenzaldehyde was used in place of 2,4-difluorobenzaldehyde.

Step D: (4-chloro-2-fluorophenyl)-(1-isobutyl-1H-indazol-5-yl)-methanol (compound 4f-7; 20.4 mg, 0.0613 mmol), "Dess Martin Periodinane" (triacetoxyperiodinane; 27.3 mg, 0.0644 mmol), and 1 mL of $CH_2Cl_2$ was stirred for 2 hours at room temperature. The reaction was loaded onto a Biotage system. The elution with 1:2 ether/hexanes provided 12.0 mg of compound 5f-7 as a solid (59.2% yield). MS ESI (+) m/z. $^1$H-NMR (400 MHz, CDCl$_3$) δ 8.15 (s, 1H), 8.11 (s, 1H), 7.99 (m, 1H), 7.53 (m, 1H), 7.47, (m, 1H), 7.30 (m, 1H), 7.24 (m, 1H), 4.21 (m, 1H), 2.37 (m, 1H), 0.95 (m, 6H).

Example 74

Preparation of (2,4-difluoro-phenyl)-[1-(2,2,2-trifluoro-ethyl)-1H-indazol-5-yl]-methanone (5f-11)

Step A: 5-bromoindazole (compound 2f; 9.852 g, 50.0 mmol) was dissolved in 150 mL of ether and the solution was cooled to −78° C. t-BuLi (1.70 M in pentane, 88.2 mL, 150 mmol) was added slowly at −78° C. After 0.5 hours at −78° C., the reaction was quenched with 2,4-difluorobenzaldehyde (10.9 mL, 100.0 mmol) and slowly warmed to room temperature. The mixture was stirred for 72 hr. at room temperature under nitrogen atmosphere and quenched with 100 mL of water. The layers were separated and the aqueous layer was extracted with $CH_2Cl_2$ (6×50 mL). The combined organic extracts were washed with saturated NaCl solution (100 mL), dried over anhydrous $MgSO_4$, filtered through Celite, and concentrated under reduced pressure to provide a yellow solid. The reaction was purified by chromatography, eluting with 5% MeOH in $CH_2Cl_2$. During the sample handling for chromatography, it was found that the desired fractions had poor solubility in $CH_2Cl_2$. Mixed fractions were combined and concentrated under reduced pressure. The resulting oil was treated with $CH_2Cl_2$ (approximately 50 mL) and the solid was formed. The solid was collected by filtration. $^1$H NMR for flashed and filtered were identical. Since the samples had poor solubility in CHCl$_3$, a couple of drops of DMSO-d6 were added to the $^1$H-NMR samples, 6.034 g of 8f-1 as a pale yellow solid (46.4% yield) was obtained. MS (ESI+) m/z 261 (M+H) detected.

Step B: Compound 8f-1 (4.954 g, 19.04 mmol) was suspended in 150 mL of $CH_2Cl_2$ and Dess Martin Periodinane (9.156 g, 1.10 equivalents) was added portion wise at room temperature. After 3 hr at room temperature, the mixture was concentrated under reduced pressure, loaded to the Samplet, and eluted with 2% MeOH in $CH_2Cl_2$ to provide solid. The solid was suspended in 300 mL of $CH_2Cl_2$ and 100 mL of saturated $K_2CO_3$ solution and stirred vigorously for 2 hours. The mixture was filtered and the filtrate was extracted with $CH_2Cl_2$ (3×100 mL). Saturated NaCl solution was added to aqueous layer and the layer was extracted with $CH_2Cl_2$ (3×100 mL). The combined extracts were dried over anhydrous $MgSO_4$, filtered through Celite, and concentrated under reduced pressure to provide 9f-1 as a light brown solid (3.407 g, 69.3% yield). MS: (ESI+) m/z 259 (M+H) detected.

Step C: Compound 9f-1 (0.258 g, 1.0 mmol), $K_2CO_3$ (0.207, 1.5 mmol), and DMF (5 mL) were placed in a small Schlenk type resealable tube. Air was evacuated from the tube and the tube was precooled in dry ice bath (no acetone). A syringe and trifluoroethyl bromide (0.244 g, 1.5 mmol) was precooled in a dry ice bath. The tube was opened and trifluoroethyl bromide was injected while the whole system was cold. The tube was sealed and heated to 100° C. After 18 hr excess DMF was removed under reduced pressure. The residue was treated with water (20 mL) and $CH_2Cl_2$ (20 mL). The layers were separated and the aqueous layer was extracted with $CH_2Cl_2$ (4×10 mL). The combined extracts were washed with brine, dried over $MgSO_4$, filtered through Celite, and concentrated under reduced pressure. The residue was purified by chromatography with 1:1 ether/hexanes, providing 64.7 mg (19% yield) of compound 5f-11. MS (ESI+) m/z 341 (M+H) detected. $^1$H NMR (400 MHz, CDCl$_3$) δ 8.20 (s, 2H), 8.05 (d, 2H), 7.62 (q, 1H), 7.52 (d, 1H), 7.04, (t, 1H), 6.95 (t, 1H), 5.00 (q, 2H).

Example 75

Preparation of (1-allyl-1H-indazol-5-yl)-(2,4-difluoro-phenyl)-methanone (5f-12)

Step A: Compound 9f-1 was prepared as described in Example 74.

Step B: Into a Schlenk type tube was placed compound 9f-1 (0.516 g, 1.0 mmol), $K_2CO_3$ (0.415 g, 1.5 mmol), DMF (10 mL), and allyl bromide (0.363 g, 1.5 mmol). The tube was sealed and heated to 100° C. After 19 hr the supernatant solution was decanted and salt was washed with DMF (5 mL×3). The combined supernatant solution was concentrated under reduced pressure. The residue was dissolved in $CH_2Cl_2$ (20 mL) and washed with water. The aqueous layer was extracted with $CH_2Cl_2$ (10 mL×2). The combined extracts were dried over anhydrous $MgSO_4$, filtered through Celite, and concentrated under reduced pressure. The residue was purified by chromatography with 1:1 ether/hexanes to provide 142.1 mg (23.8% yield) of compound 5f-12. MS (ESI+) m/z 299 (M+H) detected. $^1$H NMR (400 MHz, CDCl$_3$) δ 8.17 (s, 1H), 8.12 (s, 1H), 7.98 (d, 1H), 7.60 (m, 1H), 7.48, (d, 1H), 7.04 (td, 1H), 6.95 (td, 1H), 6.05 (m, 1H), 5.28 (d, 1H), 5.17 (d, 1H), 5.06 (dt, 2H).

Examples 76–79 describe the synthesis of aniline compounds of the general Formula XI. FIG. 32 shows a synthetic reaction scheme for the synthesis of compounds having the generic structure 1j.

Example 76

Preparation of (2,4-difluoro-phenyl)-(1-isobutyl-1H-indazol-5-yl)-amine (2h-1)

In this example, the synthesis of compound 2h-1 as shown in FIG. 32, where $R^1$ is isobutyl and Ar is 2,4-difluorophenyl is described.

Step A: Ammonium tetrafluoroborate (20.97 g, 200 mmol) was dissolved in aqueous acetic acid (500 mL AcOH/250 mL water) and cooled to 0° C. 2-Methyl-4-bromoaniline (18.61 g, 100 mmol) and 42 mL of aqueous concentrated HCl (36% w/w, 12N, 500 mmol) were sequentially added. The mixture was stirred for 20 minutes at 0° C. and NaNO$_2$ (7.59 g, 110 mmol) was added. The reaction was stirred for 1 hour at 0° C. and warmed to room temperature. After 16 hours at room temperature, the mixture was concentrated under reduced pressure and the residue was azeotroped with toluene and dried under high vacuum. The solid was suspended in 500 mL of CHCl$_3$ and KOAc (12.76 g, 130 mmol) and 18-crown-6 (7.93 g, 30 mmol) were added. The reaction was stirred for 1.5 hours at room temperature. The mixture was washed with water, dried over anhydrous MgSO$_4$, filtered through Celite and concentrated under reduced pressure to provide 30 g of 5-bromo-1H-indazole (compound 2f) as a tan solid. The crude material was used without further purification.

Step B: The crude 5-bromo-1H-indazole (compound 2f, 100 mmol) was dissolved in 250 mL of DMF. K$_2$CO$_3$ (20.7 g, 150 mmol) and 1-bromo-2-methylpropane (16.3 mL, 150 mmol) were added. The mixture was heated to 120° C. under nitrogen atmosphere for 16 hours. The mixture was cooled to room temperature and concentrated under reduced pressure. Water (200 mL) and CH$_2$Cl$_2$ (200 mL) were added to the residue and stirred vigorously for 30 minutes. The layers were separated and the aqueous layer was extracted with CH$_2$Cl$_2$. The combined extracts were dried over anhydrous MgSO$_4$, filtered through Celite, and concentrated under reduced pressure to provide about 30 g of crude material. The crude material was purified by chromatography (1:9 to 1:4 ether/hexanes) to provide 12.870 g of compound 3f as a dark red oil, yielding 50.8% for steps A and B. MS ESI (+) m/z 253 and 255 (M+1) detected. $^1$H-NMR (400 MHz, CDCl$_3$) δ 7.93 (s, 1H), 7.87 (m, 1H), 7.43 (m, 1H), 7.29 (m, 1H), 7.29 (m, 1H), 4.15 (m, 2H), 2.33 (m, 1H), 0.92 (m, 6H).

Step C: Compound 3f (2.53 g, 10.0 mmol) was dissolved in 50 ml of ether and the solution was cooled to −78° C. 12.4 mL of t-BuLi (1.7 M, 21.0 mmol) was added dropwise and the mixture stirred an additional 30 minutes at −78° C. The reaction was quenched with B(OMe)$_3$ (2.4 ml, 21.0 mmol), and slowly warmed to room temperature. After 15 minutes the reaction was quenched with 6N HCl (10 ml, 60 mmol). The reaction was transferred to a separatory funnel and water (100 ml) and CH$_2$Cl$_2$ (100 ml) were added. The layers were separated and the aqueous layer was extracted with CH$_2$Cl$_2$. The combined extracts were dried over anhydrous MgSO$_4$, filtered through Celite, and concentrated under reduced pressure and purified by chromatography with 2:1 ether/hexanes to 5% MeOH in CH$_2$Cl$_2$ to provide compound 1h as a pale yellow solid (1.41 g, 64.7% yield). MS ESI (+) m/z 219 (M+1) detected.

Step D: Compound 1h (109 mg, 0.50 mmol), copper (II) acetate (50.3 mg, 0.10 mmol), myristic acid (46 mg, 0.20 mmol), and 2 mL of dry toluene were placed in a flask. 2,6-Lutidine (58 µL, 0.50 mmol) was added and the mixture was stirred for several minutes. 2,4-Difluoroaniline (0.75 mmol, 76 µL) was added and the mixture was stirred vigorously under air atmosphere for 90 hours. The mixture was diluted with 10 mL of ether, filtered through Celite, and concentrated under reduced pressure to provide a viscous dark green oil. The crude was purified by chromatography with 1:4 ether/hexanes to provide 59 mg of compound 2h-1 as a tan oil (39% yield). MS ESI (+) m/z 302 (M+1) detected. 1H-NMR (400 MHz, CDCl$_3$) δ 7.90 (s, 1H), 7.39 (m, 1H), 7.36 (m, 1H), 7.16 (m, 1H), 7.07 (m, 1H), 6.89 (m, 1H), 6.75 (m, 1H), 5.59 (br s, 1H, NH), 4.16 (m, 2H), 2.35 (m, 1H), 0.95 (m, 6H).

Example 77

Preparation of (4-fluoro-phenyl)-(1-isobutyl-1H-indazol-5-yl)-amine (2h-2)

In this example, the synthesis of compound 2h-2 as shown in FIG. 32, where $R^1$ is isobutyl and Ar is 4-fluorophenyl is described.

Steps A–C: Compound 1h was prepared as described in Example 1, steps A–C.

Step D: Compound 1h (109 mg, 0.50 mmol), copper (II) acetate (25.2 mg, 0.05 mmol), myristic acid (23 mg, 0.10 mmol) and 2 mL of dry toluene were placed in a flask. 2,6-Lutidine (58 µL, 0.50 mmol, 1.0 equivalents) was added to the mixture and it was stirred for several minutes. 4-Fluoroaniline (71 µL, 0.75 mmol, 1.5 equivalents) was added and the mixture was stirred vigorously under air (air oxidation condition for copper catalyst) for 21 hours. The mixture was diluted with 10 mL of ether, filtered through Celite, and concentrated under reduced pressure to provide very viscous dark green oil. The crude was purified by chromatography with 1:1 ether/hexanes to provide 41 mg (28.9% yield) of compound 2h-2 as a tan oil. MS ESI (+) m/z 284 (M+1) detected. $^1$H-NMR (400 MHz, CDCl$_3$) δ 7.87 (s, 1H), 7.34 (s, 1H), 7.33 (m, 1H), 7.13 (m, 1H), 6.98~6.91 (m, 4H), 4.15 (m, 2H), 2.35 (m, 1H), 0.94 (6H).

Example 78

Preparation of (2,4-dichloro-phenyl)-(1-isobutyl-1H-indazol-5-yl)-amine (2h-9)

In this example, the synthesis of compound 2h-9 as shown in FIG. 32, where R1 is isobutyl and Ar is 2,4-dichlorophenyl is described.

Steps A–C: Compound 1h was prepared as described in Example 1, steps A–C.

Step D: Compound 1h (109 mg, 0.50 mmol), copper (II) acetate (50.3 mg, 0.10 mmol,) myristic acid (46 mg, 0.20 mmol), and 2 mL of dry toluene were placed in a flask. 2,6-Lutidine (58 µL, 0.50 mmol, 1.0 equivalents) was added to the mixture and it was stirred a couple of minutes. 2,4-Dichloroaniline (122 mg, 0.75 mmol, 1.5 equivalents) was added and the mixture was stirred vigorously under air (air oxidation condition for copper catalyst) for 90 hours. The mixture was diluted with 10 mL of ether, filtered through Celite, and concentrated under reduced pressure to provide very viscous dark green oil. The crude was purified by chromatography with 1:4 ether/hexanes to provide 59 mg of compound 2h-9 as a tan oil (35% yield). MS ESI (+) m/z 334 and 336 (M+1) detected.

Example 79

Preparation of (1-isobutyl-1H-indazol-5-yl)-O-tolyl-amine (2g-10)

In this example, the synthesis of compound 2h-10 as shown in FIG. 32, where $R^1$ is isobutyl and Ar is 2-methylphenyl is described.

Steps A–C: Compound 1h was prepared as described in Example 1, steps A–C.

Step D: Compound 1h (109 mg, 0.50 mmol), copper (II) acetate (50.3 mg, 0.10 mmol), myristic acid (46 mg, 0.20 mmol), and 2 mL of dry toluene were placed in a flask. 2,6-Lutidine (58 µL, 0.50 mmol, 1.0 equivalents) was added to the mixture and it was stirred a couple of minutes. 80 µL of O-toluidine (0.75 mmol, 1.5 equivalents) was added and the mixture was stirred vigorously under air (air oxidation condition for copper catalyst) for 90 hours. The mixture was diluted with 10 mL of ether, filtered through Celite, and concentrated under reduced pressure to provide very viscous dark green oil. The crude was purified by chromatography with 1:4 ether/hexanes to provide 77 mg of compound 2h-10 as a tan oil (55% yield). MS ESI (+) m/z 280 (M+1) detected.

Examples 80–82 describe the synthesis of amino acid compounds of the general Formula XV. FIG. 33 shows a synthetic reaction scheme for the synthesis of compounds having the generic structure 2h.

Example 80

Preparation of 4-amino-2-{[5-(4-fluorophenoxy)-1-isobutyl-1H-indazole-6-carbonyl]-amino}butyric acid methyl ester (1j-2)

Step A: Compound 10g-1 was prepared as described in Example 46.

Step B: A solution of compound 10g-1 (50 mg, 0.15 mmol) in THF (0.5 mL) was treated with CDI (1.1 equivalents) at room temperature under $N_2$ atmosphere. After stirring for 18 hours, 2-amino-4-tert-butoxycarbonylamino butyric acid methyl ester (36 mg, 0.165 mmol), was added, followed by the addition of N,N-diisopropylethylamine (29 mg, 0.225 mmol). After stirring for 18 hours, the reaction was concentrated, the residue taken up in $CH_2Cl_2$ and washed with 1 N HCl. The organic layer was filtered through 1PS paper and purified in a SepPak cartridge eluting with 10:1 $CH_2Cl_2/Et_2O$. The desired fractions were concentrated to yield 72 mg of compound 1j-1 as a beige foam (99% yield). $^1$H NMR (400 MHz, DMSO-d6) δ 8.65 (br, 1H), 8.10 (s, 1H), 7.9 (s, 1H), 7.28 (1H, s), 4.21 (d, 2H), 4.42 (m, 1H), 3.6 (s, 3H), 2.95 (m, 2H).

Step C: A solution of compound 1j-1 (72 mg, 0.13 mmol) in $CH_2Cl_2$ (0.2 mL) was treated with TFA (0.1 mL) at room temperature. After 18 hours, the solvent was concentrated and co-evaporated from ether, yielding 70 mg (98% yield) of compound 1j-2 as an amber oil. $^1$H NMR (400 MHz, DMSO-d6) δ 8.85 (br, 1H), 8.01 (s, 1H), 7.98 (s, 1H), 7.70 (br, 2H), 4.60 (m, 1H), 4.22 (d, 2H), 3.80 (s, 3H), 2.85 (m, 2H).

Example 81

Preparation of 4-amino-2-{[5-(4-fluorophenoxy)-1-(2,2,2-trifluoroethyl)-1H-indazole-6-carbonyl]-amino}butyric acid methyl ester (1j-4)

Step A: Compound 10g-2 was prepared as described in Example 59.

Step B: Compound 10g-2 (0.026 g, 0.073 mmol), benzotriazole-1,3-diol (0.013 g, 0.088 mmol) and (3-dimethylaminopropyl)-ethylcarbodiimide (0.017 g, 0.088 mmol) were added to dichloroethane and mixed for 10 minutes. Next, a heterogeneous mixture of the HCl salt of 2-amino-4-t-butoxycarbonylamino butyric acid methyl ester (0.039 g, 0.147 mmol) and triethylamine (0.030, 0.29 mmol) in dichloroethane were added. The reaction mixture was stirred for 3 hours, concentrated and purified by reversed phase HPLC according to Method A of Example 86 to provide approximately 30 mg of pure compound 1j-3 (71.9% yield). MS (ESI+) m/z 569 (M+H) detected.

Step C: Compound 1j-3 (0.0012 g, 0.024 mmol) was added to 1:1 $CH_2Cl_2$/TFA for 1.5 hours, then concentrated to provide 2.3 mg (100% yield) of compound 1j-4. $^1$H NMR (400 MHz, CDCl$_3$) δ 9.21 (br, 1H), 8.40 (br, 1H), 8.04 (br, 1H), 7.44 (br, 1H), 7.18 (s, 1H), 7.03 (m, 3H), 5.05 (m, 2H), 4.80 (br, 1H), 3.75 (s, 3H), 3.36 (br, 1H), 2.97 (br, 1H), 2.51 (br, 1H), 1.92 (br, 1H).

Example 82

Preparation of 4-amino-2-{[5-(4-fluorophenoxy)-1-methyl-1H-indazole-6-carbonyl]-amino}butyric acid methyl ester (1j-6)

Step A: Compound 10g-3 was prepared as described in Example 60.

Step B: Compound 10g-3 (0.026 g, 0.090 mmol), benzotriazole-1,3-diol (0.017 g, 0.11 mmol) and (3-dimethylaminopropyl)ethylcarbodiimide (0.021 g, 0.017 mmol) were added to dichloroethane and mixed for 10 minutes. Next, a heterogeneous mixture of the HCl salt of 2-amino-4-tert-butoxycarbonylamino butyric acid methyl ester (0.05 g, 0.20 mmol) and triethylamine (0.037, 0.36 mmol) in dichloroethane were added. The reaction mixture was stirred for 3 hours and then purified by reversed phase HPLC according to Method A of Example 86 to provide 30 mg (66% yield) of compound 1j-5 as pure material. MS (ESI+) m/z 501 (M+H) detected.

Step C: Compound 1j-5 (0.0012 g, 0.024 mmol) was added to 1:1 $CH_2Cl_2$/TFA for 1.5 hours, then concentrated to provide 1.2 mg (100% yield) of compound 1j-6. $^1$H NMR (400 MHz, CDCl$_3$) δ 9.10 (br, 1H), 8.32 (br, 1H), 8.05 (br, 1H), 7.90 (s, 1H), 7.05 (s, 1H), 7.05 (m, 3H), 4.75 (br, 1H), 4.14 (s, 3H) 3.65 (s, 3H), 3.30 (br, 1H), 2.92 (br, 1H), 2.51 (br, 1H), 1.82 (br, 1H).

Examples 83–85 describe the synthesis of compound of Formula XVI as shown in FIG. 34.

Example 83

Preparation of 5-(4-fluorophenoxy)-1-isobutyl-1H-indazole-6-carboxylic acid (2-dimethylaminoethyl)-amine (1k-1)

Compound 11g-10 (0.05 g, 0.12 mmol), prepared as described in Example 59, was treated with 6 equivalents of $BH_3$ in THF (1 M solution) and stirred at 65° C. for 6 hours and then at room temperature for 14 hours. The solvent was removed by evaporation, and the residue was purified on by preparative TLC using 1:1 hexane/ethyl acetate and 5% triethylamine to provide 0.014 g (30% yield) of product. MH+ observed: 385.

Example 84

Preparation of Compound 1k-2

Compound 1k-1, prepared as in Example 83, was treated with excess acetic anhydride and triethylamine in THE at room temperature for 4 hours and then concentrated to provide 0.010 g of 1k-2. MH+ observed: 427.

Example 85

Preparation of Compound 1k-3

Compound 1k-1, prepared as in Example 83, was treated with excess methanesulfonyl chloride and triethylamine in THE at room temperature for 4 hours. The reaction mixture was concentrated and the residue purified by preparative TLC using 1:1 hexane/ethyl acetate and 5% triethylamine to provide 0.005 g (50% yield). MH+ observed: 463.

Example 86

Preparative RP-HPLC Conditions

Method A:
Column: YMC ODS-AQ, 250×20 mm i.d., s-10/20 μm, 12 nm. Solvent A: $H_2O$ with 0.1% TFA. Solvent B: acetonitrile with 0.05% TFA. Collection triggered by mass spectrometer.

|  | % A | % B | flow rate |
| --- | --- | --- | --- |
| 0.03 min | 85 | 15 | 10 ml/min |
| 1.50 min | 85 | 15 | 20 ml/min |
| 22.5 min | 15 | 85 | 20 ml/min |
| 24.0 min | 5 | 95 | 20 ml/min |
| 32.25 min | 5 | 95 | 15 ml/min |
| 32.75 min | 95 | 5 | 15 ml/min |

Method B:
Column: YMC ODS-AQ, 250×20 mm i.d., s-10/20 μm, 12 nm. Solvent A: $H_2O$ with 0.1% TFA. Solvent B: acetonitrile with 0.05% TFA. Collection triggered by mass spectrometer.

|  | % A | % B | flow rate |
| --- | --- | --- | --- |
| 0.03 min | 95 | 5 | 10 ml/min |
| 1.50 min | 95 | 5 | 20 ml/min |
| 22.5 min | 5 | 95 | 20 ml/min |
| 24.0 min | 5 | 95 | 15 ml/min |
| 30.5 min | 95 | 5 | 15 ml/min |

Method C:
Column: YMC ODS-AQ, 250×20 mm i.d., s-10/20 μm, 12 nm. Solvent A: $H_2O$ with 0.1% TFA. Solvent B: acetonitrile with 0.05% TFA. Collection triggered by mass spectrometer.

|  | % A | % B | flow rate |
| --- | --- | --- | --- |
| 0.03 min | 95 | 5 | 10 ml/min |
| 1.50 min | 95 | 5 | 15 ml/min |
| 18.5 min | 5 | 95 | 15 ml/min |
| 20.0 min | 5 | 95 | 15 ml/min |
| 20.85 min | 95 | 5 | 15 ml/min |

Example 87

Preparation of Compound 1m-1

Figure 37:
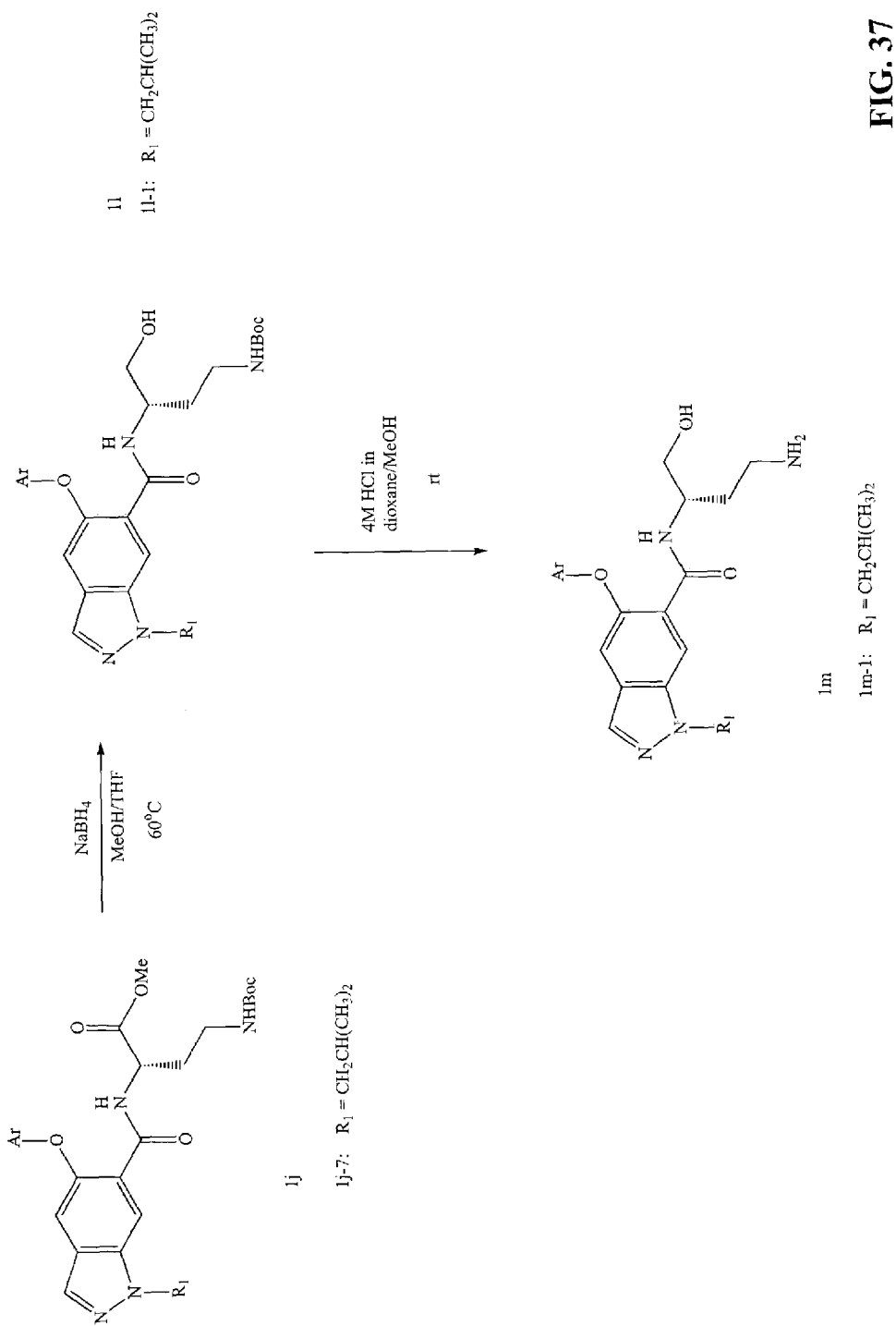
FIG. 37 shows a reaction scheme for the synthesis of compounds having the generic structure 1m.

The synthesis of compound 1m-1 is shown in FIG. 37.

Step A: Compound 1j-7 (0.07 g, 0.13 mmol), prepared in a manner similar to that described for compound 1j-3, was treated with sodium borohydride (10 equivalents, 0.049 g, 1.3 mmol) in 1:1 MeOH/THF and heated to 60° C. for 3 hours. The reaction mixture was concentrated and then coevaporated with MeOH to provide compound 1l-1.

Step B: Compound 1l-1 was places in a 1:1 mixture of MeOH/4 M HCl in dioxane for 1.5 hours, and then the reaction mixture was concentrated. The residue was taken up in chloroform, washed with a 0.6 M $Na_2CO_3$ solution (pH 7.0) and aqueous saturated NaCl, and dried over $MgSO_4$. After filtration, the filtrate was evaporated to provide compound 1m-1 (99% pure) as the free base. H-NMR (400 MHz), $CDCl_3$: δ 8.39 (d, 1H), 8.34 (s, 1H), 7.90 (s, 1H), 7.24 (s, 1H), 6.98 (M, 4H), 4.27 (m, 1H), 4.20 (d, 2H), 3.64 (m, 2H), 2.65 (m, 1H), 2.39 (m, 1H), 2.37 (m, 1H), 2.18 (m, 1H), 1.59 (m, 1H), 0.93 (d, 6H).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound including resolved enantiomers, diastereomers, solvates and pharmaceutically acceptable salts thereof, said compound having the Formula:

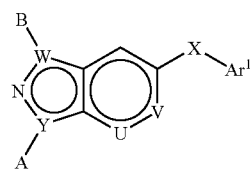

wherein
Y is C, N;
W is C or N, provided that W is N, when Y is C, and W is C when Y is N;
U is CH;
V is C-E;

X is O, S, SO, SO$_2$, or NR$^7$;

Z is alkylene having from 1 to 4 carbons, or alkenylene or alkynylene each having from 2 to 4 carbons, wherein said alkylene, alkenylene, or alkynylene may be substituted or unsubstituted;

R$^7$ is H or substituted or unsubstituted methyl;

Ar$^1$ is aryl which may be substituted or unsubstituted;

A is H, alkyl, allyl, alkenyl, or alkynyl, wherein said alkyl, allyl, alkenyl, and alkynyl, may be substituted or unsubstituted;

R$^2$ and R$^3$ are independently H, OH, an amine protecting group, alkyl, allyl, alkenyl, alkynyl, heteroalkyl, heteroallyl, heteroalkenyl, heteroalkynyl, alkoxy, heteroalkoxy, Z$_n$-cycloalkyl, or Z$_n$-Ar$^1$, wherein said alkyl, allyl, alkenyl, alkynyl, heteroalkyl, heteroallyl, heteroalkenyl, heteroalkynyl, alkoxy, heteroalkoxy, Z$_n$-cycloalkyl, or Z$_n$-Ar$^1$ may be substituted or unsubstituted, B is H, NH$_2$, or substituted or unsubstituted methyl;

E is Z$_n$-(C=O)R$^4$;

R$^4$ is NR$^2$R$^3$; and n is 0 or 1, provided that when B is H and A is CH=CH—R$^8$ where R$^8$ is a substituted or unsubstituted alkyl, alkenyl, cycloalkyl, heterocycloalkyl, aryl, or heteroaryl, then X is not O, S, SO NH, or N(C$_1$-alkyl).

2. The compound of claim 1, wherein Ar$^1$ is phenyl.

3. The compound of claim 2, wherein Ar$^1$ is 4-chlorophenyl, 4-fluorophenyl, 3-methylphenyl, 3-fluorophenyl, 3-chlorophenyl, 3-(MeS)-phenyl sulfide, 3-(MeSO$_2$)-phenyl, or 3-methyl-4-flurophenyl.

4. The compound of claim 1, wherein A is H, 4-MeO-Ph-(CH$_2$), CH$_2$CH=CH$_2$, CH$_2$CH(OH)CH$_2$OH, CH$_2$C(=O)H, CH$_2$-isoxazole, (CH$_2$)NH$_2$, (CH$_2$)NHBoc, CH=CHPh, CH$_2$OH, CH$_2$OCH$_3$, methyl, ethyl, isopropyl, or CH$_2$CF$_3$.

5. The compound of claim 1, wherein Y is N.

6. The compound of claim 1, wherein Y is C.

7. The compound of claim 1, which is selected from:
5-(4-fluorophenoxy)-1-isobutyl-1H-indazole-6-carboxylic acid amide;
5-(4-fluorophenoxy)-1-isobutyl-1H-indazole-6-carboxylic acid (2-benzylaminoethyl)-amide;
5-(4-fluorophenoxy)-1-isobutyl-1H-indazole-6-carboxylic acid (2-piperidin-yl-ethyl)-amide;
5-(4-fluorophenoxy)-1-isobutyl-1H-indazole-6-carboxylic acid (2-pyrrolidin-1-yl-ethyl)-amide;
5-(4-fluorophenoxy)-1-isobutyl-1H-indazole-6-carboxylic acid (3-morpholin-4-yl-propyl)-amide; and
5-(4-fluorophenoxy)-1-isobutyl-1H-indazole-6-carboxylic acid (3-dimethylaminopropyl)-amide.

8. The compound of claim 1, which is selected from:
5-(4-fluorophenoxy)-1-isobutyl-1H-indazole-6-carboxylic acid methyl-(1-methylpiperidin-4-yl)-amide;
5-(4-fluorophenoxy)-1-isobutyl-1H-indazole-6-carboxylic acid [3-(methylphenylamino)-propyl]-amide;
5-(4-fluorophenoxy)-1-(2,2,2-trifluoroethyl)-1H-indazole-6-carboxylic acid (2-dimethylaminoethyl)amide;
5-(4-fluorophenoxy)-1-methyl-1H-indazole-6-carboxylic acid (2-dimethylaminoethyl)amide; and
5-(4-fluorophenoxy)-1H-indazole-6-carboxylic acid (2-dimethylaminoethyl)amide.

9. The compound of claim 1, which is selected from:
4-amino-2-{[5-(4-fluorophenoxy)-1-isobutyl-1H-indazole-6-carbonyl]-amino}butyric acid methyl ester;
4-amino-2-{[5-(4-fluorophenoxy)-1-(2,2,2-trifluoroethyl)-1H-indazole-6-carbonyl]-amino}butyric acid methyl ester; and
4-amino-2-{[5-(4-fluorophenoxy)-1-methyl-1H-indazole-6-carbonyl]-amino}butyric acid methyl ester.

10. The compound of claim 1, which is (S)-N-(4-amino-1-hydroxybutan-2-yl)-5-(4-fluorophenoxy)-1-isobutyl-1H-indaziole-6-carboxamide.

11. The compound of claim 1, wherein n is 0.

12. The compound of claim 11, wherein A is alkyl, wherein said alkyl may be substituted or unsubstituted.

13. The compound of claim 11, wherein NR$^2$R$^3$ is NH$_2$,

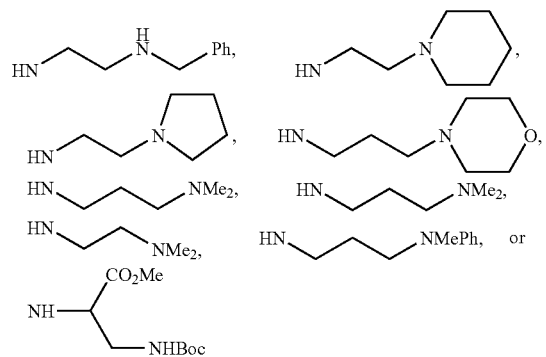

14. The compound of claim 1, wherein X is O.

15. The compound of claim 5, wherein X is O.

16. The compound of claim 6, wherein X is O.

* * * * *

UNITED STATES PATENT AND TRADEMARK OFFICE
CERTIFICATE OF CORRECTION

PATENT NO. : 7,135,575 B2 Page 1 of 1
APPLICATION NO. : 10/378164
DATED : November 14, 2006
INVENTOR(S) : Mark Munson et al.

It is certified that error appears in the above-identified patent and that said Letters Patent is hereby corrected as shown below:

In column 76, line 64, claim 1, delete the comma after the second "N".

In column 77, line 27, claim 2, add --or napthyl-- after "phenyl".

In column 77, line 31, claim 3, delete "flurophenyl" and insert --fluorophenyl--.

In column 78, line 3, claim 8, delete "methyl-(1-methylpiperidin-4-yl)-amide" and insert --(2-dimethylaminoethyl)-amide--.

In column 78, line 7, claim 8, insert a space between ")" and "amide".

In column 78, line 9, claim 8, insert a space between ")" and "amide".

In column 78, line 11, claim 8, insert a space between ")" and "amide".

In column 78, line 21, claim 10, italicize "N".

In column 78, line 24, claim 10, delete "indaziole" and insert --indazole--.

Signed and Sealed this

First Day of July, 2008

JON W. DUDAS
*Director of the United States Patent and Trademark Office*